US012171869B2

(12) United States Patent
Sawhney et al.

(10) Patent No.: US 12,171,869 B2
(45) Date of Patent: Dec. 24, 2024

(54) INTRACAMERAL DRUG DELIVERY DEPOTS

(71) Applicant: Incept, LLC., Lexington, MA (US)

(72) Inventors: Amarpreet S. Sawhney, Lexington, MA (US); Arthur Driscoll, Reading, MA (US); Charles D. Blizzard, Nashua, NH (US); Ankita D. Desai, Reading, MA (US); Peter Jarrett, Lexington, MA (US)

(73) Assignee: Incept, LLC, Lexington, MA (US)

( * ) Notice: Subject to any disclaimer, the term of this patent is extended or adjusted under 35 U.S.C. 154(b) by 0 days.

(21) Appl. No.: 15/714,633

(22) Filed: Sep. 25, 2017

(65) Prior Publication Data

US 2018/0085307 A1  Mar. 29, 2018

Related U.S. Application Data

(60) Provisional application No. 62/398,985, filed on Sep. 23, 2016.

(51) Int. Cl.

| | |
|---|---|
| A61K 9/00 | (2006.01) |
| A61F 9/00 | (2006.01) |
| A61F 9/007 | (2006.01) |
| A61K 9/16 | (2006.01) |
| A61K 47/10 | (2017.01) |
| A61K 31/382 | (2006.01) |
| A61K 31/40 | (2006.01) |
| A61K 47/34 | (2017.01) |

(52) U.S. Cl.
CPC .......... *A61K 9/0051* (2013.01); *A61F 9/0017* (2013.01); *A61F 9/00781* (2013.01); *A61K 9/1647* (2013.01); *A61K 47/10* (2013.01); *A61K 9/0092* (2013.01); *A61K 31/382* (2013.01); *A61K 31/40* (2013.01); *A61K 47/34* (2013.01)

(58) Field of Classification Search
CPC . A61F 9/0017; A61F 9/00781; A61K 9/0051; A61K 9/1647; A61K 47/10; A61K 9/0092; A61K 31/382; A61K 31/40; A61K 47/34

See application file for complete search history.

(56) References Cited

U.S. PATENT DOCUMENTS

| | | |
|---|---|---|
| 3,640,741 A | 2/1972 | Etes |
| 3,865,108 A | 2/1975 | Hartop |
| 3,992,562 A | 11/1976 | Denzinger et al. |
| 4,002,173 A | 1/1977 | Manning et al. |
| 4,014,335 A | 3/1977 | Arnold |
| 4,207,893 A | 6/1980 | Michaels |
| 4,741,872 A | 5/1988 | De Luca et al. |
| 4,826,945 A | 5/1989 | Cohn et al. |
| 4,938,763 A | 7/1990 | Dunn et al. |
| 5,100,992 A | 3/1992 | Cohn et al. |
| 5,160,745 A | 11/1992 | De Luca et al. |
| 5,304,595 A | 4/1994 | Rhee et al. |
| 5,324,775 A | 6/1994 | Rhee et al. |
| 5,326,761 A | 7/1994 | Rozier |
| 5,410,016 A | 4/1995 | Hubbell et al. |
| 6,149,931 A | 11/2000 | Schwartz et al. |
| 6,177,401 B1 | 1/2001 | Ullrich et al. |
| 6,371,975 B2 | 4/2002 | Cruise et al. |
| 6,699,493 B2 | 3/2004 | Wong |
| 6,884,890 B2 | 4/2005 | Kania et al. |
| 6,958,212 B1 | 10/2005 | Hubbell et al. |
| 7,033,605 B2 | 4/2006 | Wong |
| 7,129,210 B2 | 10/2006 | Lowinger et al. |
| 7,141,581 B2 | 11/2006 | Bender et al. |
| 7,413,752 B2 | 8/2008 | Sawhney |
| 8,383,161 B2 | 2/2013 | Campbell et al. |
| 8,409,606 B2 | 4/2013 | Sawhney et al. |
| 8,563,027 B2* | 10/2013 | Jarrett ................. A61F 9/00772 264/118 |
| 8,715,709 B2 | 5/2014 | Huang et al. |
| 8,889,193 B2 | 11/2014 | McDonnell et al. |
| 8,895,508 B2 | 11/2014 | Tabata et al. |
| 9,011,915 B2 | 4/2015 | Wong et al. |
| 9,061,065 B2 | 6/2015 | Robinson et al. |

(Continued)

FOREIGN PATENT DOCUMENTS

| | | |
|---|---|---|
| WO | 2006031358 | 3/2006 |
| WO | 2006031388 | 3/2006 |

(Continued)

OTHER PUBLICATIONS

D'Souza et al. "Development of a Dialysis In Vitro Release Method For Biodegradable Microspheres", AAPS PharmSciTech, vol. 6(2):E323-E328 (Oct. 6, 2005).

D'Souza et al., "Unstirred Water Layer Effects On Biodegradable Microspheres" Advances in Pharmaceutics, vol. 2015:12 Pages (2015).

Faulkner et al., "Aqueous Humor Concentrations of Bimatoprost Free Acid, Bimatoprost and Travoprost Free Acid in Cataract Surgical Patients Administered Multiple Topical Ocular Doses of LUMIGAN or TRAVATAN" Journal Ocul Pharmacol Ther, vol. 26(2):147-156 (Apr. 2010).

(Continued)

*Primary Examiner* — Sean M Basquill
(74) *Attorney, Agent, or Firm* — Christensen, Fonder, Dardi & Herbert PLLC; Peter S. Dardi; Diane E. Bennett

(57) ABSTRACT

Methods of treating an eye for an ocular condition such as placing a composite depot comprising a xerogel with embedded degradable particles into an anterior chamber of an eye to deliver a therapeutic agent. The xerogel is a hydrogel after exposure to intraocular fluid and is degradable. The degradable particles comprise the therapeutic agent and hydrolytically degrade in the anterior chamber to provide a controlled release of the therapeutic agent into the eye. Materials and processes for making depots are provided as well as alternative methods of their use.

26 Claims, 14 Drawing Sheets

(56) References Cited

U.S. PATENT DOCUMENTS

| | | | |
|---|---|---|---|
| 9,125,807 | B2 | 9/2015 | Sawhney et al. |
| 9,173,773 | B2 * | 11/2015 | Borgia .................. A61F 9/0017 |
| 9,205,150 | B2 | 12/2015 | Jarrett et al. |
| 9,283,231 | B2 | 3/2016 | Wong et al. |
| 9,289,413 | B2 | 3/2016 | Hughes et al. |
| 9,308,283 | B2 | 4/2016 | Campbell et al. |
| 2002/0138154 | A1 | 9/2002 | Li et al. |
| 2004/0024345 | A1 | 2/2004 | Gharib et al. |
| 2004/0086479 | A1 | 5/2004 | Grinstaff et al. |
| 2004/0086548 | A1 | 5/2004 | St. John et al. |
| 2004/0131582 | A1 | 7/2004 | Grinstaff et al. |
| 2004/0137059 | A1 | 7/2004 | Nivaggioli et al. |
| 2005/0049578 | A1 | 3/2005 | Tu et al. |
| 2009/0017097 | A1 | 1/2009 | Sawhney et al. |
| 2010/0209478 | A1 | 8/2010 | Sawhney et al. |
| 2010/0278898 | A1 | 11/2010 | Hughes et al. |
| 2011/0142936 | A1 | 6/2011 | Campbell et al. |
| 2012/0071865 | A1 | 3/2012 | Jarrett et al. |
| 2013/0017243 | A1 | 1/2013 | Shi et al. |
| 2013/0071462 | A1 * | 3/2013 | Jarrett ..................... A61P 27/02 424/422 |
| 2014/0143636 | A1 | 5/2014 | Frost et al. |
| 2016/0166504 | A1 | 6/2016 | Jarrett et al. |
| 2017/0143636 | A1 | 5/2017 | Jarrett et al. |
| 2018/0085307 | A1 | 3/2018 | Sawhney et al. |

FOREIGN PATENT DOCUMENTS

| | | | |
|---|---|---|---|
| WO | 2007001926 | | 1/2007 |
| WO | 2007005249 | | 1/2007 |
| WO | 2010111449 | | 9/2010 |
| WO | WO-2010111449 | A1 * | 9/2010 ........... A61K 9/0051 |
| WO | 2013086015 | A1 | 6/2013 |
| WO | 2014138085 | | 9/2014 |
| WO | 2014165308 | | 10/2014 |
| WO | 2015085251 | | 6/2015 |
| WO | 2016094646 | | 6/2016 |

OTHER PUBLICATIONS

Gentile et al., "An Overview of Poly(lactic-co-glycolic) Acid (PLGA)-Based Biomaterials for Bone Tissue Engineering", International Journal of Molecular Sciences, vol. 15:3640-3659 (2014).

Lee et al., "Additive Ocular Hypotensive Effects of Bimatoprost Sustained-Release Intracameral Implant on Potent Topical Therapy in Monkeys", ARVo 2016 Annual Meeting, 2 Pages (May 1-5, 2016).

Lewis et al., "Bimatoprost Sustained-Release Implants for Glaucoma Therapy: Interim Results From a 24-Month Phase 1/2 Clinical Trial", Presented at the American Academy of Ophthalmology 2015 Annual Meeting, 10 Pages, (Nov. 14-17, 2015).

Makadia et al., Poly Lactic-co-Glycolic Acid (PLGA) as Biodegradable Controlled Drug Delivery Carrier, Polymers, vol. 3(3):1377-1397 (Sep. 1, 2011).

Martinez-De-La-Casa et al, "Effects of Corneal Thickness on the Intracular Penetration of Travoprost 0.004%" Eye vol. 26:972-975 (2012).

Narayanaswamy et al. "Diagnostic Performance of Anterior Chamber Angle Measurements for Detecting Eyes With Narrow Angles", Arch Ophthalmol, vol. 128(10): 7 Pages (Oct. 2010).

Navratil et al., "Design and Development of ENV515 Intraocular Applicator for Intracameral Injections of ENV515 Glaucoma Extended Release (XR) Therapy", ARVO 2016 Annual Meeting, 2 pages (May 1-5, 2016).

Perera et al., "Bimatoprost Sustained-Release Implants for Glaucoma Therapy: 12-Month Interim Results From a Phase 1/2 Clinical Trial", ARVO 2016 Annual Meeting, 2 pages (May 1-5, 2016).

Walker et al., "A Phase 1 Pharmacokinetic Study to Assess the Relative Systemic Bimatoprost Exposure Following Placement of a Novel Bimatoprost Ocular Insert in Healthy Adults", ARVO 2016 Annual Meeting, 2 pages (May 1-5, 2016).

Walters et al., "Completed 28-Day and Ongoing 12 Month Safety and Efficancy Evaluation of ENV515 (Travoprost) Intracameral Implant in Phase 2 Study", ARVO 2016 Annual Meeting, 2 pages (May 1-5, 2016).

Wilhelmus "The Draize Eye Test", Survey of Ophthalmolgy, vol. 45(6):493-515 (2001).

Zhu et al. "Design Properties of Hydrogel Tissue-Engineering Scaffolds", Expert Review of Medical Devices, vol. 8 (5):607-626 (Sep. 2011).

Carvalho et al. "Effects Of Travoprost 0.004% Compared with Latanoprost 0.005% on the Intraocular Pressure of Normal Dogs", Veterinary Ophthalmolgy, vol. 9(2): 121-125 (2006).

Driscoll et al., "90 Day Canine Toxicity Study Demonstrating the Safety of a Sustained Release Travoprost Punctum Plug" Investigative Ophthalmology & Visual Science, vol. 55 (Apr. 2014).

Driscoll et al., "Toxicity and Pharmacokinetics of Sustained-Release Dexamethason in Beagle Dogs", Adv Ther, vol. 33(1):58-67 (Jan. 2016).

Gelatt et al., "Effect of Different Dose Schedules of Travoprost on Intraocular Pressure and Pupil Size in Glaucomatous Beagle", Veterinary Ophthalmology, vol. 7(1):53-57 (2004).

Hellberg et al., "Preclinical Efficacy of Travoprost, a Potent and Selective FP Prostaglandin Receptor Agonist", Journal of Ocular Pharmacology and Therapeutics, vol. 17:421-432 (2001). (2001).

MacKay et al., "Dose Response for Travoprost in Glaucomatous Beagles" Veterinary Ophthalmology (2011).

Strom et al., "In Vivo Evaluation of the Cornea and Conjuctiva of the Normal Laboratory Beagle Using Time- and Fourier-Domain Optical Coherence Tomography and Ultrasound Pachymetry", Veterinary Ophthalmology, vol. 19 (1):50-56 (2016).

Trevino et al., "Intracameral Conversion of Travoprost to Travoprost Acid in the Normotensive Beagle Dog Model", Investigative Ophthalmology & Visual Science, vol. 55 (Apr. 2014).

Bilzzard et al., "Pharmacokinetic Studies of Sustained-Release Depot of Dexamethasone in Beagle Dogs", Journal of Ocular Pharmacology and Therapeutics, vol. 32 (Nov. 2016).

First Examination Report from corresponding Indian Patent Application No. 201917015053, 6 pages, Dated Dec. 17, 2020.

International Search Report and Written Opinion from corresponding PCT application No. PCT/US2017/053271 dated Dec. 6, 2017, 11 pages.

Bacharach et al. "Phase 3, Randomized, 20-Month Study of the Efficacy and Safety of Bimatoprost Implant in Patients with Open-Angle Glaucoma and Ocular Hypertension (ARTEMIS 2)", Published online: Nov. 1, 2021, https://doi.org/10.1007/s40265-021-01624-9, Drugs (2021) 81:2017-2033.

Kim et al. "Persistent Remnants of Dexamethasone Intravitreal Implant (Ozurdex)", Retina, The Journal of Retinal and Vitreous Diseases 2020, vol. 00, pp. 1-6.

Pardo-Lopez et al., "Anterior Chamber Migration of Dexametasona Intravitreal Implant (Ozurdex®)", Graefes Arch Clin Exp Ophthalmol (2012) 250:1703-1704.

Walters et al. "Efficacy and Safety of Sustained Release Dexamethasone for the Treatment of Ocular Pain and Inflammation after Cataract Surgery: Results from Two Phase 3 Studies", J Clin Exp Ophthalmol 2016, 7:4, pp. 1-11.

Notice of Preliminary Rejection and English translation thereof from corresponding Korean Patent Application No. 10-2019-7011614, dated Jan. 13, 2022. 25 pages.

* cited by examiner

INTRACAMERAL DRUG DELIVERY DEPOTS

CROSS REFERENCE TO RELATED APPLICATIONS

This patent application claims priority to U.S. Provisional Patent Application No. 62/398,985, filed Sep. 23, 2016 and which is hereby incorporated by reference in its entirety.

TECHNICAL FIELD

The technical field relates to materials and methods of drug delivery to treat an ocular condition, particularly drug delivery from a composite hydrogel-microparticle depot located in an eye to treat an eye disease.

BACKGROUND

Drugs for treatment of an eye require a suitable means of delivery to be effective. Drug delivery relates to administering a pharmaceutical compound to achieve a therapeutic effect in humans or animals. Delivery mechanisms that provide release of an agent over time are useful. Drug delivery technologies can help to improve drug efficacy and safety, as well as patient convenience and compliance.

SUMMARY

The eye presents multiple challenges for sustained drug delivery devices, although such devices, if effective, have many benefits. Materials and methods are provided that provide for long-term release of other therapeutic agents.

An embodiment of the invention is a method of treating an eye for an ocular condition, the method comprising placing a composite depot comprising a xerogel with embedded hydrolytically degradable particles into an anterior chamber of an eye to deliver a therapeutic agent, with the xerogel being a hydrogel after exposure to intraocular fluid, with the hydrogel being hydrolytically degradable, wherein the hydrolytically degradable particles comprise the therapeutic agent and hydrolytically degrade in the anterior chamber to provide a controlled release of the therapeutic agent into the eye, wherein an index of depot residue retention (IRR) is from 0.5 to 2.0, with IRR being a time to full dissolution of the depot divided by a time to release of 100% of the therapeutic agent. Embodiments include processes of making the depot and its use to treat a disease or a medical condition.

Another embodiment of the invention is a depot composition comprising a xerogel with embedded hydrolytically degradable particles, with the xerogel being a biocompatible hydrogel after exposure to intraocular fluid, with the hydrogel being hydrolytically degradable, wherein the hydrolytically degradable particles comprise a therapeutic agent and hydrolytically degrade in a physiological fluid to provide a controlled release of the therapeutic agent for use in the treatment of an ocular disease.

DETAILED DESCRIPTION

Figure 1A:
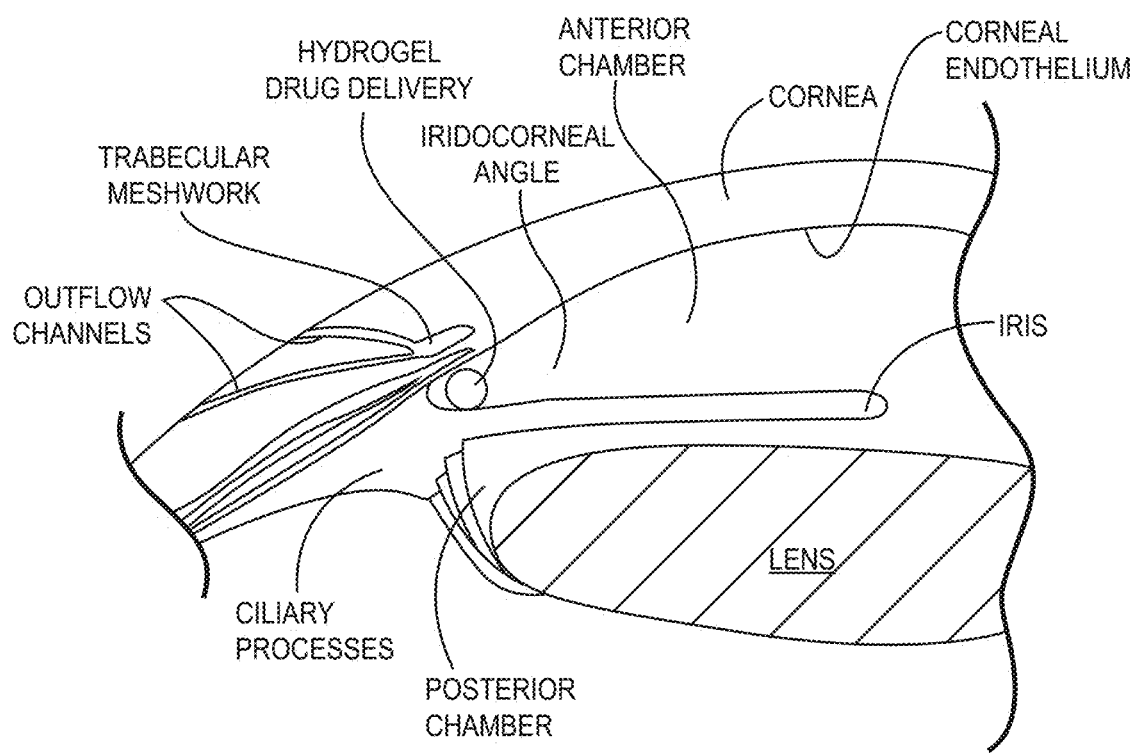
FIG. 1A depicts a hydrogel composite depot placed in an anterior chamber of the eye, in the iridocorneal angle.
Figures 1B, 1C, 1D:
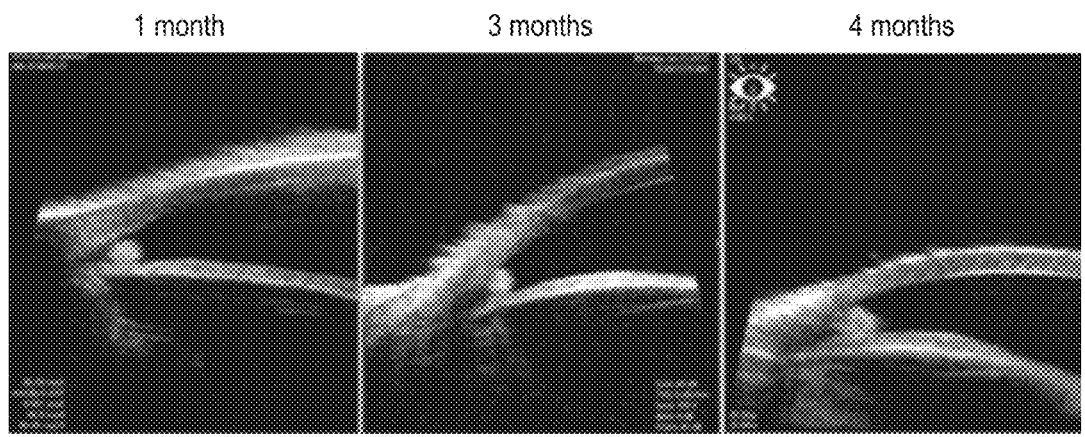
FIGS. 1B-1D are ultrasound images of a hydrogel depot in the anterior chamber of the eye, in the iridocorneal angle, in a beagle, at 1 month (1B), 3 months (1C) and 4 months (1D) post-introduction.

An embodiment of the invention is a method of treating an eye for an ocular condition, comprising placing a composite xerogel-microparticle depot in an anterior chamber of an eye to deliver a therapeutic agent, the xerogel being a hydrogel after exposure to intraocular fluid and comprising particles that controllably release a therapeutic agent into the eye after placement of the depot into the eye. Materials and compositions for the xerogel, particles, agents, and hydrogels are also aspects of the invention, as well as processes of making, use, methods of administration, and treatment of ocular conditions. FIG. 1A depicts a hydrogel depot placed in an anterior chamber of the eye, in the iridocorneal angle. Further embodiments include release of agents that are dispersed in the hydrogel without encapsulation, either in addition to, or an alternative to delivery of agents that are in particles.

The anterior chamber depicted in FIG. 1A is a fluid-filled space inside an eye between the iris and the corneal endothelium. The anterior chamber is typically about 2.5 to 3.5 mm deep in healthy eyes of adult humans. The fluid in the anterior chamber is the aqueous humor and it is drained primarily through the trabecular meshwork located in the iridocorneal angle of the eye. The trabecular meshwork is drained by outflow channels, particularly the canal of Schlemm. Aqueous humor is constantly produced in the ciliary body and flows through the anterior chamber to the trabecular meshwork; thus, creating a continuous flow field in the anterior chamber. Poor drainage of the anterior chamber can lead to ocular pathologies, with hyphema, ocular hypertension and glaucoma being the most prominent. In hyphema, blood fills the anterior chamber. In glaucoma, blockage of fluid drainage to the canal of Schlemm causes increased intraocular pressure that leads to blindness. Some conditions cause the depth of the anterior chamber to decrease, which can block drainage through the trabecular meshwork. Delivery of agents to the anterior chamber would be of interest for agents that act on the drainage pathways of the chamber. For instance, travoprost is an agent that is believed to increase drainage to the canal of Schlemm. Referring to FIG. 1A the anterior chamber is beneath the cornea and is connected to the vitreous humor of the eye by the posterior chamber located between the iris and the lens. The lens is anchored by ciliary processes. The trabecular meshwork is drained though outflow channels. A hydrogel for delivery of a therapeutic agent is located in the iridocorneal angle. FIGS. 1B-1D are ultrasound images of a hydrogel depot in the anterior chamber of the eye, in the iridocorneal angle, in a beagle, at 1 month, 3 months and 4 months post-placement.

The anterior chamber, however, is small, has sensitive tissues, and is part of the eye's mechanisms for passing light into the interior of the eye. Drug delivery anywhere in the eye is subject to multiple challenges and competing design requirements. On the one hand, the eye is a sensitive organ and the frequency of placing depots into the eye would ideally be minimized so that the patient does not have to endure repeated discomfort and inconvenience. Therefore as much of the agent as possible should be introduced at one time and the agent should be delivered in an effective amount for as long as possible; these conditions point to a depot that is large. But the eye has a limited volume and will not tolerate large devices. And trauma at the time of placement is minimized by making the depot as small as possible. And agents are therapeutic only at an appropriate concentration, with too little being ineffective and too much having a toxic effect. Further, it is challenging to design and make depots that release agents in the correct amount over the life of the depot. In the anterior chamber, the corneal endothelium is particularly sensitive to trauma. And the depot itself can elicit unwanted biological responses that confound efforts to safely deliver the agents. These responses can stem from the choice of materials, depot size, proximity or contact with certain parts of the eye, the release of the agent, the chemistry of the agent, and other factors. In addition, the flow field of aqueous humor fluid in the anterior chamber will influence drug release rates from typical sustained release depot designs, which may be variable from patient to patient, making control of drug delivery pharmacokinetics difficult. A somewhat slower flow field exists in the vitreous humor. In this respect, the anterior chamber, and to a lesser extent the vitreous humor, present a more challenging environment for sustained drug delivery than other parts of the human anatomy. Taken together, there are a number of conflicting design considerations that work against a lengthy delivery of agents from depots in the eye or the anterior chamber.

Embodiments of the invention include a composite depot that contains a xerogel component when administered to a patent that is a hydrogel in aqueous solution environments, for example, as in FIGS. 2-6. The xerogel is small relative to the hydrogel so as to minimize the size of needles or other tools used for placement. The hydrogel contains particles that hold the agent or agents that are to be delivered. The agent is disposed in biodegradable microparticles, such as PLGA, that degrade in water to release the agent. The microparticles may be chosen to create a release profile for the agent that is suited to its site of placement and required agent concentrations in the eye.

Working examples of successful in vitro and in vivo xerogel/hydrogel-microparticle therapeutic agent releasing systems release are provided. Without being bound to a particularly theory, it appears that the systems interacted with the aqueous humor (AH) in a manner that provided unexpected, surprising, and unpredicted excellence in biocompatibility and drug delivery rate control. AH fluid flows radially from the center of the iris out through the trabecular meshwork. This flow is constant, but may vary among patients.

Particles of hydrolytically degradable material erode more slowly in a quiescent physiological or other aqueous solution as compared to a moving solution (described herein as a flow field). Diffusion is a controlling factor in a quiescent solution but movement of the solution (convection) increases the rate of drug release from an unprotected particle. In a flow field, a hydrolyzable drug release matrix, such as PLGA, is expected to release drug more quickly than in a quiescent medium, due to more rapid removal of released drug from the particle-water interfacial zone coupled with more rapid particle erosion, due to removal of hydrolysis products from the interfacial zone. Such acceleration of drug release has been documented in the literature. See S. D'Souza, J. A. Faraj, P. P. DeLuca, "Unstirred Water Layer Effects on Biodegradable Microspheres," Advances in Pharmaceutics 2015, D'Souza et al., tested release of an agent from degradable particles under quiescent conditions and in a flow field (continuous agitation i.e. in a 50 mL stoppered glass cylinder, microspheres were subjected to moderate agitation using a magnetic stir bar sufficient to ensure good suspendability of the microspheres in the release media and minimal sedimentation in the release vessel) and reported that the in vitro release profiles for the static and continuous agitation conditions were "drastically different." It was therefore expected that the flowing aqueous humor would accelerate the degradation of the particles and rate of release of agents from the particles. But the rate of drug delivery from the particles was not substantially affected by the flowing trabecular fluid until the hydrogel was far advanced in degradation. Experimental results demonstrating this shielding phenomenon are presented in Example 7, below. Apparently, the hydrogels shielded the particles from the convective fluid forces in the anterior chamber, limiting the drug release to diffusion control only. The thickness of the hydrogel layer will influence the magnitude of the shielding effect. Although the flow field could be expected to accelerate release rates, this was not observed.

A hydrogel should provide an adequate thickness around entrapped particles of drug in order to provide the shielding effect. In context of a composite depot, the weight of the hydrogel matrix should be at least 20% compared to a weight of the agent-containing particles in the hydrogel plus a weight of the xerogel matrix when the depot is dry. Accordingly, concentrations of 20%, 25%, 30%, 33%, 35%, 40%, 50%, 60%, 70%, 75%, 80%, 85%, 90% w/w; artisans will immediately appreciate that all ranges and values between the explicitly stated bounds are contemplated, e.g., 21% or 20%-50% or 25%-40% w/w. The hydrogel matrix is the crosslinked network formed by crosslinking precursor molecules to make the hydrogel. Artisans can ascertain these weights, for instance the weight of the total dried depot can be calculated by knowledge of all the components used to make the depot or simply measured, and the weight of the precursors used to make the hydrogel can be known or calculated based on the precursor composition used to make the hydrogel. These measurements are to be made in distilled water for simplicity, since the products are designed for use in a physiological solution wherein salts do not make a significant contribution to weight compared to the other components. The depots should also be designed to persist for an amount of time that is suited to the application, as discussed below in the context of an index of depot residue retention (IRR). The hydrogel should also be chosen to have suitable mechanical strength, stability during a period of time intended for the delivery of the agent; hydrogel design factors are discussed below in detail. In general, the matrix content of at least 20% w/w discussed above is preferred for these purposes and having one or more precursors with at least 3 points of crosslinking is helpful, with 4 or more being preferred; these factors are further discussed below.

Hydrogels can typically allow for water to freely diffuse through a hydrogel matrix. And, in general, hydrogels that have a mesh size that is larger than the size of agents in the hydrogel can be expected to typically release agents without large effects on their rate of release, provided that the agents are soluble in the solution and do not interact with the matrix. While not being bound by a particular theory, it is believed that, in a composite depot of a hydrogel and degradable particles that contain a therapeutic agent, the agent is released from the microparticle surface and diffuses through the hydrogel to the hydrogel surface, with a consequent decrease in concentration at the surface according to Fick's law. The agent release rate is then determined by the reduced concentration at the hydrogel surface, so the hydrogel layer thickness affects the release rate. The particles are chosen to release the agent at a rate that cooperates with the hydrogel surface area. The Examples describe various working examples demonstrating the same.

Different polymer compositions and structures can be designed to meet these requirements. Typically, covalently crosslinked hydrogels with hydrolyzable linkages are preferred. Also, in most cases the hydrogel should be inert with respect to drug interactions. Therefore, nonionic hydrogels without substantial hydrophobic domains are preferred. For instance, hydrophilic precursors that are nonionic may be used. Polyethylene glycols are an example of a family of hydrophilic nonionic polymers that can be used to form the preferred hydrogel structures. Those skilled in the art know it may be possible to engineer hydrogels to interact with the eluting drug in a way that modulates the drug release rate. However, in a composite depot, there is no advantage to hydrogel modulation of drug release, since the release rate for a depot can be set for controllably degradable particles. Accordingly, embodiments include hydrogels and agents that are free of specific binding with each other and/or covalent bonding to each other. Embodiments include depots that are free of one or more of: a hydrogel mesh size that is smaller than the agent molecular weight (discussed below), precursors that have hydrophobic domains, precursors that are not water soluble, precursors that specifically bind with each other, and precursors that crosslink with each other by physical (non-covalent) bonds.

In practice, a composite depot allows hydrolytically degrading particles to be used inside a hydrogel in a convective fluid environment without being variably affected by patient to patient flow field variability, or anatomic location flow field variability. For instance, unshielded microparticles can be loaded with large amounts of an agent that would be released so quickly in a convective fluid that the amounts would be toxic. Or the particles can be preserved by the hydrogel from quick degradation such that the depot can be longer-lasting than otherwise possible. Advantageously as compared to particles made for use without a shielding hydrogel, the particles may be designed with lower amounts of degradable materials, and more therapeutic agent, without creating a weak particle that otherwise provides a too-quick release of the drug. The shielding phenomenon was used advantageously to create hydrogels to shield particles for a duration of time that allowed the particles to complete, or substantially complete, delivery of the agents. The hydrogels could then be designed to degrade at about the time that the particles had delivered their agents, or soon after complete delivery, or adjusted to degrade earlier than complete drug release, such that the amount of agents released increases after disappearance of the hydrogel.

The shielding effect can be used not only for hydrogels that allow for free diffusion of agents but also for hydrogels with a tighter meshwork relative to the agent or an agents that interact with the hydrogel.

Further, hydrogels in the anterior chamber apparently experienced surface erosion in the flow field of the anterior chamber. Synthetic absorbable polymeric materials (e.g. PLGA) are generally bulk eroding, i.e. where chemical degradation and mass loss occurs at a uniform rate throughout the bulk of the material. Before breaking up, the hydrogel is referred to as being self-cohesive or monolithic. If the hydrogel breaks-up into pieces as a result of degradation, the hydrogel will continue to erode and gradually dissolve, at which point it is not visible. In the anterior chamber, toward the end of hydrogel bulk hydrolysis, degradation of the hydrogel gradually exposed the embedded microparticles. The exposed agent-containing particles rapidly eroded and disappeared. By the time that the hydrogel had disintegrated, most of the agent had been released or essentially fully released such that any remaining release of agent provided only a low dose of drug that was not potentially harmful to the eye. In certain embodiments, the hydrogel matrix will dissolve and microparticles within the shell that carry a therapeutic agent will continue to provide sustained release of drug into the surrounding environment for continued therapy. Once drug release is completed then the microparticle matrix will continue to biodegrade for subsequent clearance from the injection site.

One of the problems in the eye and in the anterior chamber in particular is that degradable materials for release of the agents can have poor biocompatibility relative to a hydrogel. The particle-related degradable materials can be acidic and, in low concentrations, are reasonably tolerated but, in higher amounts, they can create unfavorable local conditions. Poly(glycolic acid) (PGA), poly(lactic acid) (PLA), poly(lactic acid)-co-poly(glycolic acid) (PLGA) are materials that create acidic degradation products. Others have used PLGA rods that erode but these are less biocompatible than hydrogels and have been observed to persist long after their useful drug delivery life has passed. Repeated treatment, as for chronic conditions, could lead to accumulation of empty depot matrix material in the patient's tissue. Since the rods are in direct contact with the local tissue and the PLGA has limitations as to its biocompatibility, such materials are less biocompatible than a hydrogel. Further, they may pass through a stage of fragmentation, where the left-over fragments have a high surface area and release a burst of acidic degradation products at the end of their life cycle. Returning to certain aspects of the invention, the distribution of PLGA or other particle-related degradable materials, after disappearance of the hydrogel shield, into small particles provides a high surface area that takes advantage of surface-erosion effects to degrade the particle-related degradable materials. Moreover, since microparticles of the invention do not need mechanical strength, drug loading into the microparticle can be higher than monolithic formats of the same composition, so that the total quantity of the particle-related degradable material can be much lower as compared to a large rod or monolithic structure, making degradation product concentrations lower and any end-burst degradation is lower or negligible. This is visually evident when individual PLA microparticle formulations prepared separately are weight blended together to achieve a targeted sustained release profile, e.g. FIG. 7. The microparticles prepared with lower PLA molecule weights release their drug fully and then proceed to disappear within the hydrogel matrix leaving behind a visual "swiss cheese" effect indicative of the PLA components liquefying and being release through the hydrogel matrix. PLA microparticles prepared with higher molecular weights release the drug more slowly and the microparticle remnants may or may not be present when the hydrogel has reached a liquefied state. Overall this composite structure minimizes tissue exposure to PLA or PLGA degraded materials until the hydrogel has fully degraded, whereas injection of conventional unshielded PLA or PLGA sustained release drug products or devices exposes tissues to prolonged and extensive contact with the matrix materials (PLA or PLGA, etc.) which can elicit localized tissue inflammatory response.

A residue of material that exceeds the useful drug-delivery life is problematic for chronic conditions requiring repeated serial placement of depots, for example, as in glaucoma. In a long lasting depot case, multiple emptied depots can accumulate in the eye or require removal. These depots may even lead to inflammatory conditions. It is desired that the depot residue exits the eye soon after delivering its payload of therapeutic agents. An index of depot residue retention (IRR) is defined as the time to full dissolution of the depot comprising a therapeutic agent divided by the time to release of 100% of the therapeutic agent. If a depot delivers drug for 0.5 years and then remains in the eye for 2 years, the index of depot residue retention is 4. It is generally desired that the index be close to a value of 1. For chronic conditions requiring serial depots, an index of 2 would result in the presence of two depots in the eye after the first re-introduction. An index value of 3 would result in and accumulation of three depot bodies after the second re-introduction. An increasing index of depot residue retention would then correspond to an increasing number of depot residue bodies accumulating at the depot site. If, for example, the depot site is the anterior chamber of the eye, accumulation of depot residue bodies could affect vision, damage local tissues due to impingement, damage local tissue due to an increasing output of degradation products, or other detrimental effects. To avoid accumulation of depot residue bodies, it is desired that the index of depot residue retention be less than 2 and preferably less than 1.5. Artisans will immediately appreciate that all ranges and values between the explicitly stated bounds are contemplated, with, e.g. any of the following being available as an upper or lower limit: 0.5, 0.6, 0.7, 0.8, 0.9, 1.0, 1.1, 1.2, 1.3, 1.4, 1.5, 1.6, 1.7, 1.8, 1.9, 2.0. In the case of a depot comprising a bioabsorbable hydrogel containing bioabsorbable particles that comprise a drug, the hydrogel portion, which is the majority of the depot mass when hydrated, may be designed to disappear (fully degraded) before the full drug release point. In this case the index of depot retention would be less than 1, since the bulk of the depot mass, and the monolithic form, will have been eliminated at that point, leaving only disconnected microparticles. Similarly, a degradable depot comprising a therapeutic agent that is released from the depot has an index of depot residue retention time that is a time to degradation (measurable by disappearance) divided by the time to release all of the agent.

Figure 9:
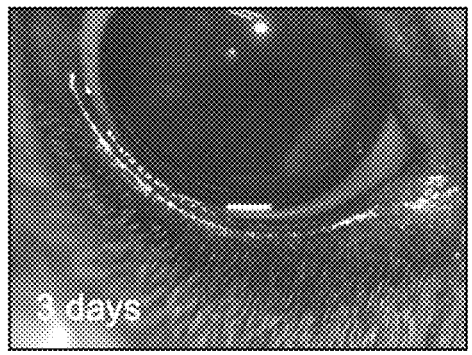
FIG. 9 is a photograph of crosslinked matrices in an anterior chamber at 3 days post-placement, under fluorescent conditions.
Figures 10A, 10B, 10C:
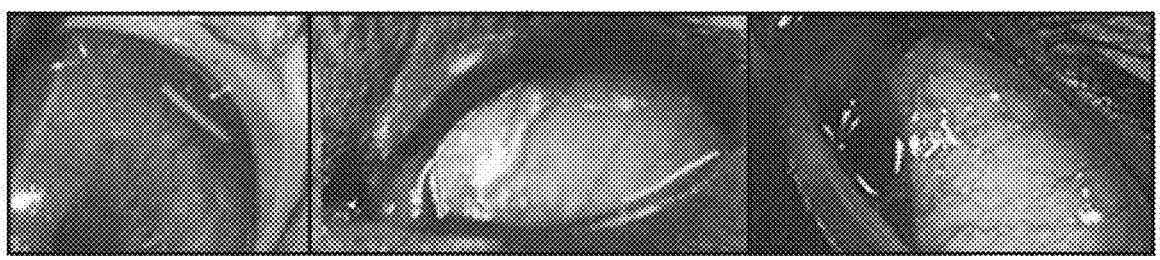
FIGS. 10A-10F are a photomontage of results from Example 4, demonstrating results indicating effective delivery of an agent to an eye, at day 0 (10A), day 3 (10B), day 7 (10C), day 28 (10D), day 70 (10E), and day 140 (10F)
Figures 10D, 10E, 10F:
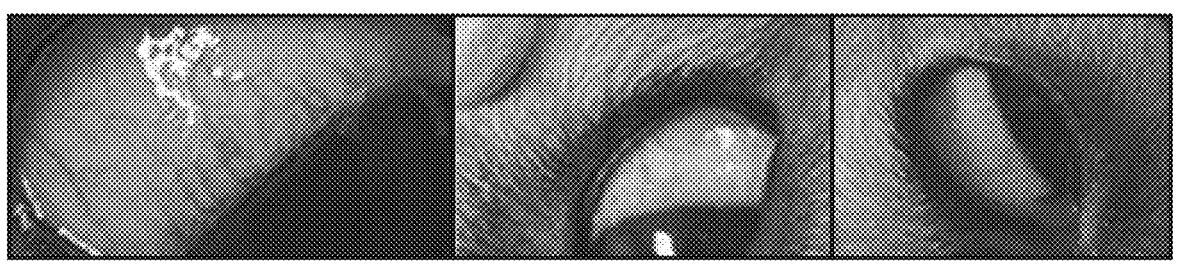
Figures 11A, 11B:
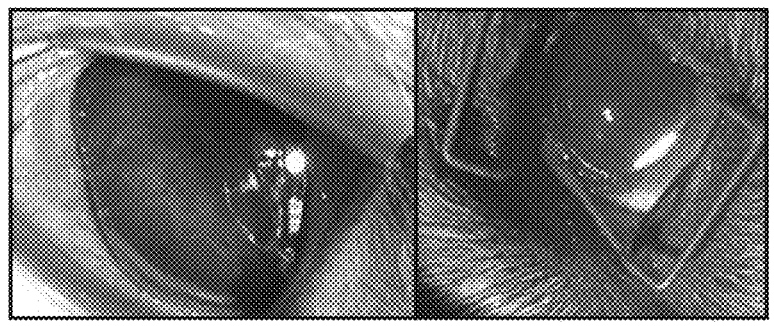
FIGS. 11A-11D are a photomontage of a composite depot in the anterior chamber photographed at Day 28 under Natural (11A, 11B) and Fluorescence (11C, 11D) conditions.
Figures 11C, 11D:
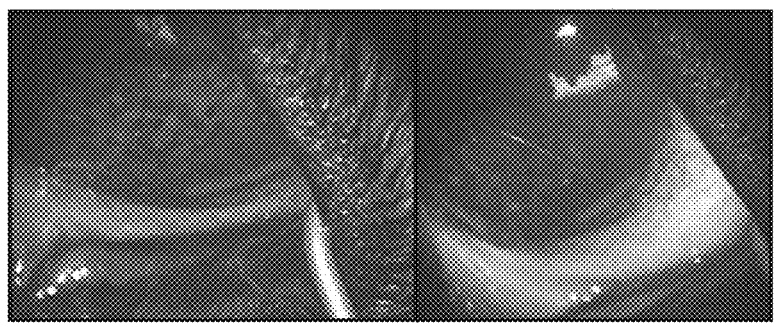

FIGS. 1A-1D depict a crosslinked matrix that is a hydrogel in an anterior chamber of the eye, in the iridocorneal angle. The hydrogel can be a xerogel before it is placed in the eye, as in FIG. 2 that depicts a xerogel can be made to by various processes so that it selectively changes shape upon exposure to aqueous media, as in FIG. 3, see also US 2017/0143636. Agents for release from the matrices can be prepared as particles, for instance particles that have a controlled-release property, and combined with the matrices, as in FIGS. 4-5. The sizes or content of the particles can be adjusted, as in FIG. 6, to make the particles release the agents at various rates and periods of time, with FIG. 7 being examples of a release profile. The hydrogel can be introduced into the anterior chamber, e.g., as in FIGS. 8A-8D and visualized at FIG. 9.

Example 1 describes preparation of a depot. The depot is a sustained release hydrogel composite depot. The depots were made with degradable microparticles comprising the therapeutic agent travoprost, which is conventionally used as an ophthalmic solution that is applied as a topical medication for controlling the progression of glaucoma or ocular hypertension, by reducing intraocular pressure. Travoprost is a synthetic prostaglandin F $2\alpha$ analogue. Its chemical name is isopropyl (Z)-7-[(1R,2R,3R,5 S)-3,5-dihydroxy-2-[(1E,3R)-3-hydroxy-4-[($\alpha,\alpha,\alpha$-trifluoro-m-tolyl)oxy]-1-butenyl]cyclopentyl]-5-heptenoate. It is a prostaglandin analogue that is enzymatically converted to a free acid form in the stroma of the human cornea. Travoprost free acid is a selective FP prostanoid receptor agonist which is believed to reduce intraocular pressure by increasing trabecular meshwork and uveoscleral outflow. The exact mechanism of action for travoprost remains unknown at this time. Travoprost is an example of an agent for use in a depot.

The depots of Example 1 comprise the active ingredient, travoprost; poly (D,L-lactide) (PLA) microparticles containing encapsulated travoprost; and the inactive delivery platform, a polyethylene glycol (PEG) covalently crosslinked matrix conjugated with fluorescein. The hydrogel was made from an 8-armed 15,000 Da polyethylene glycol terminated in succinimidyl adipate (8a15K PEG SAP) combined with trilysine. Prior to PEG hydrogel cross-linking, a small percentage portion of the amine in the trilysine precursor molecule was reacted with NHS Fluorescein. The NHS-Fluorescein reacts efficiently with primary amino groups to form stable amide bonds. The resultant fluorescent hydrogel illuminates when excited with a blue light source, such as a slit lamp, allowing an investigator the ability to confirm product presence. In Example 1, the depot was formulated to deliver travoprost in a sustained release manner for approximately 100 days (see FIG. 7). The composite depot of FIG. 7 was made according to the processes of Example 1 and is the same as the test articles, except the amount of microparticles was changed to provide a dose of 40 µg. As is evident from the guidance provided herein in regards to making hydrogels and drug delivery vehicles, e.g. particles, delivery times of up to about 2 years at a therapeutically effective dose in a human eye are practical for a single hydrogel depot; all times from 10 days to 2 years are contemplated. The PLA microparticles are bioresorbable and degrade by hydrolysis over time providing sustained release of travoprost at therapeutic levels. The 100-day sustained release profile is obtained by blending microparticles encapsulating travoprost prepared with different PLA molecular weights into the hydrogel matrix.

The depots of Example 1 had the contents indicated in Table 1. The two test articles shared the same travoprost loaded polylactide (PLA) blended microspheres and therefore are intended to have comparable release profiles of the travoprost from the drug product on a percentage basis. The difference between the two test articles is the travoprost dose and the dried diameter (Test Article 1 with 40 µg dose travoprost, 0.25 mm diameter or Test Article 2 with 26 µg dose travoprost, 0.21±0.01 mm diameter×3.02±0.02 mm length). As demonstrated in the working examples, both test articles demonstrated drug levels in the anterior chamber through 112 days coinciding with the pharmacodynamic effect of pupil constriction (miosis) in the beagle model.

The depots were sized for placement in an anterior chamber. Over time and through hydrolysis, the hydrogel and PLA components soften, liquefy, and clear through outflow pathways from the anterior chamber. Clearing the anterior chamber channels is therapeutic for ocular hypertension, glaucoma, and other conditions. The depots in the anterior chamber were easily visualized using a slit lamp or blue light with yellow filter through 56 days. By day 84 the hydrogel portion of the depot had fully degraded and no fluorescence of the depot was evident. The travoprost microparticles remained and continued to deliver drug to the anterior chamber demonstrating pupil constriction as a pronounced pharmacodynamic affect. Example 2 shows in vitro controlled release of travoprost from depots made as in Example 1. Only low dose quantities are required for a pharmacodynamic effect with travoprost acid. Due to the higher potency of the travoprost acid for the prostaglandin receptors a low dose in the range of 10 to 100 µg may be delivered over two years from microparticles fabricated with, e.g. ester end group high molecular weight polylactides or from polycaprolactone (PCL) to deliver therapeutic quantities sufficient for efficacy and IOP reduction.

While PLGA and PLA are the most frequently employed biodegradable polymers for sustained release of therapeutic agents, they are not the only forms of biodegradable polymers. PCL can be employed to encapsulate drugs within depots s or microparticles using similar processes. PCL can also be used within a copolymer with PLA, and the copolymer has been demonstrated to be safe and is employed in approved medical products. For instance, biodegradable levonorgestrel-releasing depot made of PCL filled with dry levonorgestrel (LNG) demonstrated 2-year release in rats and dogs. Biodegradation of PCL is slow in comparison to other polymers, so it is suitable for long-term delivery extending over a period of more than 1 year.

Figure 12:
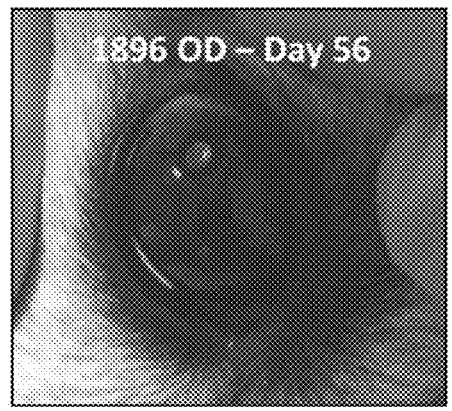
FIG. 12 is an image of a depot of the experiment of Example 4 photographed at Day 56 Under Fluorescence Conditions.

The Test Articles 1 or 2 were introduced into anterior chambers as described in Example 3. FIG. 12 is an image taken at 56 days as described in the results, shown in Example 4. A desired pharmacodynamic response to the sustained release of travoprost from OTX-TI was demonstrated by continued pupil constriction through 112 days and reduced intraocular pressure (IOP) at 28 days. Travoprost concentrations in the AH in beagles sampled at day 28 were similar to the maximum drug concentration (Cmax) reported in the literature for travoprost eye drops in humans. The results showed that the hydrogel portion of the depots was persistent at day 56 and that the travoprost was successfully delivered and had the desired effects according to a variety of measures detailed in Example 4. Over 56 days the depots remained intact and then were absent at 84 days (not shown), leaving behind the travoprost containing microparticles to release the drug into the anterior chamber. They were observed to reside in the lower portion of the anterior chamber in the iridocorneal angle. Ophthalmic examination showed excellent biocompatibility with the test articles. There was no evidence of localized inflammation proximate to the depot and the ophthalmic exams demonstrated that the eyes were considered healthy and normal with the noted exceptions of pupil constriction due the anticipated effect from the travoprost and the early hyperemia which diminished over time as shown in FIGS. 10A-10F. Note lack of blood vessel dilation at Day 0 compared to Days 3 and 7 and then the reduction over time to normal for a single animal during the study duration. Also note the pupil constriction on Day 0 shortly after administration.

Example 5 describes results of two further experiments using composite depots similar to those made in Examples 1 and 2, with certain changes as noted, including a lower travoprost dose per depot (18 µg). These showed successful delivery of effective doses of the therapeutic agent accompanied by successful treatment of the ocular condition using the drug. Example 6 presents further testing using similar composite depots with a low (14 µg) or high (41 µg) dose of agent (travoprost). The agent was released in a correspondingly low or high dose, showing further control of the rate and duration of release and control of dosage. Both doses were effective.

Example 7 demonstrated the shielding effect of the hydrogel in a hydrogel composite depot. Composites containing microparticles were tested both with (as in a flow field) and without (quiescent environment) agitation. The release profiles essentially overlapped through the duration of the test, regardless of the presence or absence of convective forces created by agitation. These tests demonstrate that the hydrogel shielded the microparticles from the convective forces of agitation. In contrast, as explained above, convection forces make particles degrade much faster than quiescent conditions. It is surprising that the hydrogel had this shielding effect, considering that water can diffuse through hydrogels. Without being bound to a particular theory, it appears that there is boundary layer effect at the hydrogel surface that resists convective mixing of the water at its surface.

Figure 16:
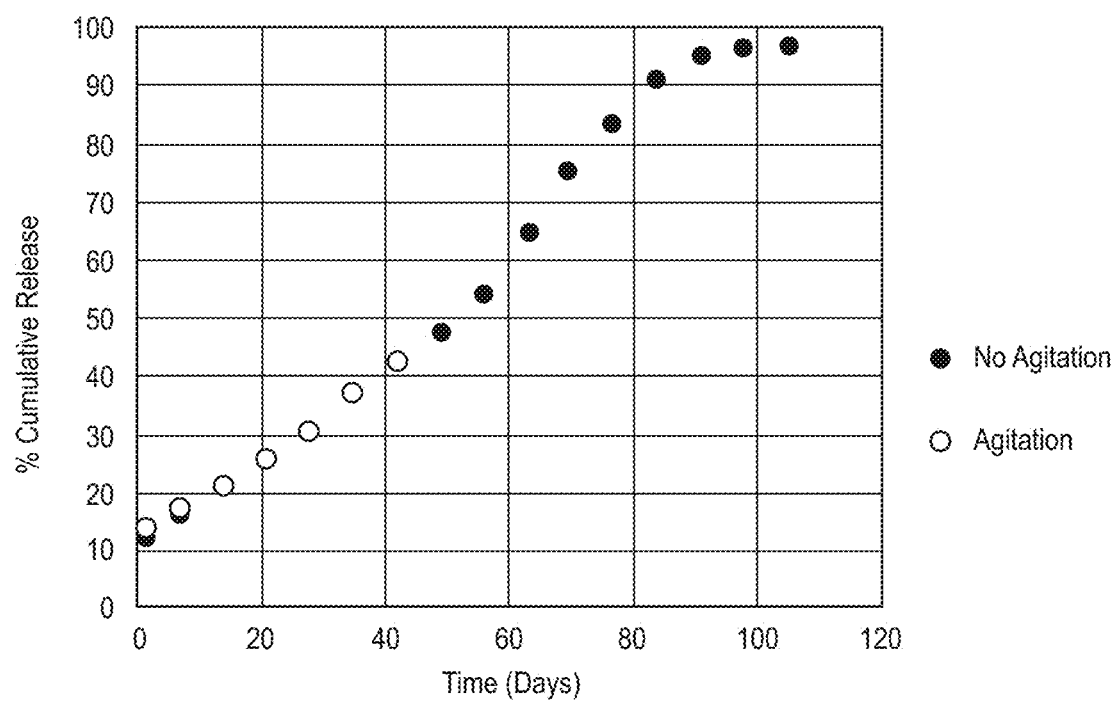

The hydrogel shielding effect can be quantified as a coefficient of increased delivery time. Referring to Example 7 and FIG. 16, and also D'Souza et al., FIG. 3 (not shown herein) it can be seen that release of an agent can be measured with a plot of cumulative percentage release of the agent over time. To calculate the coefficient of increased delivery time, a set of particles is tested under the conditions of Example 7 under the same conditions except for a presence or an absence of a hydrogel that embeds the particles. The test is run until the samples have released 100% of the agents. The coefficient of increased delivery time is the time for complete release (100%) of agents in a presence of the hydrogel divided by the time for complete release (100%) of agents without the hydrogel. For instance, a set of particles may release 100% of an agent at day 15 without a hydrogel and release the agents at day 150 with the hydrogel, in which case the coefficient of increased delivery time is 10.

Various components of the composite depots are described below; these components may be combined with each other and used according to the guidance provided herein.

Hydrogels and Xerogels

Hydrogels are materials that do not dissolve in water and retain a significant fraction (more than 20% w/w) of water within their structure. In fact, water contents in excess of 70, 80, or 90% are often known. Hydrogels may be formed by crosslinking water soluble molecules to form networks of essentially infinite molecular weight. Hydrogels with high water contents are typically soft, pliable materials. Hydrogels and drug delivery systems as described in U.S. Publication Nos. 2009/0017097, 2011/0142936, 2012/0071865, and US 2017/0143636 may be adapted for use with the materials and methods herein by following the guidance provided herein; these references are hereby incorporated herein by reference for all purposes, and in case of conflict, the instant specification is controlling.

Figure 2:
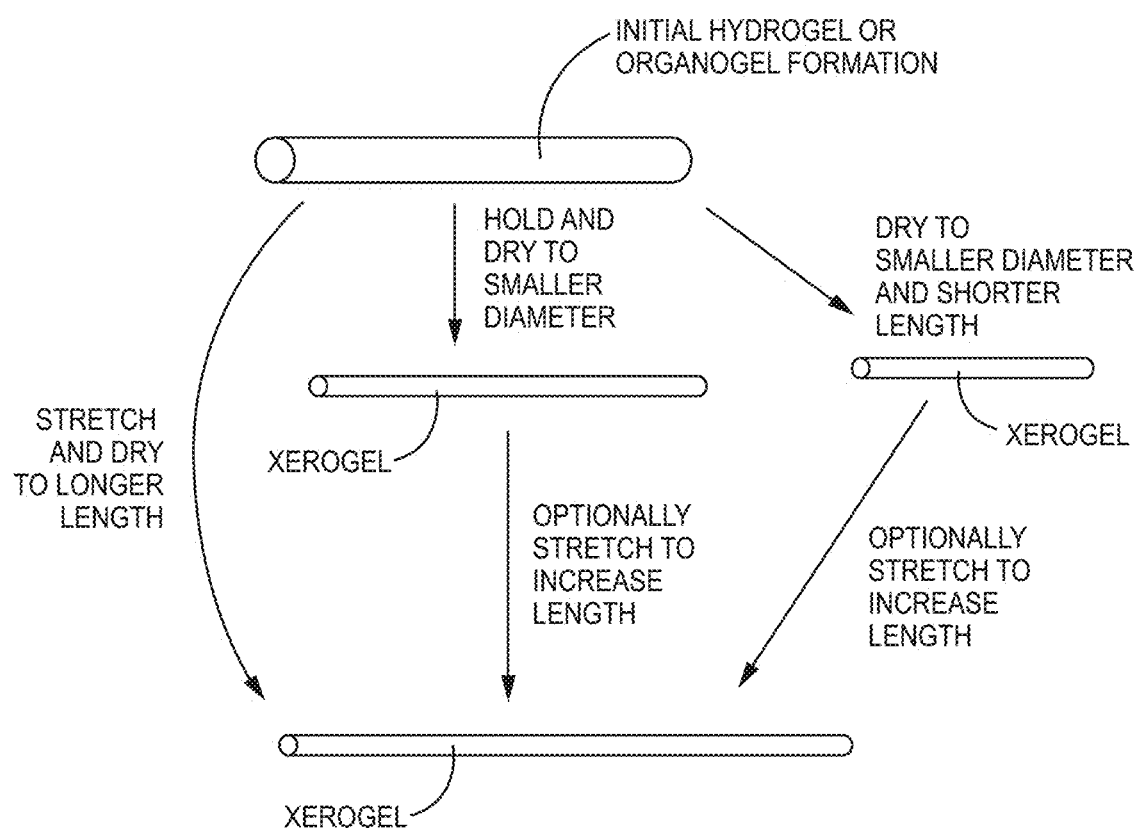
FIG. 2 depicts a hydrogel or organogel that is dried to form a xerogel.

The hydrogels can be formed as hydrogels in aqueous solution or as organogels in organic solution, e.g., as in FIG. 2. The hydrogels include an agent as provided herein in various embodiments. The term xerogel refers to a dry matrix. After formation of the matrix in a solvent, the solvent may be removed to form the xerogel. Potential processes include, e.g., precipitation or extraction with non-solvent, nitrogen sweep drying, vacuum drying, freeze-drying, a combination of heat and vacuum, and lyophilization.

In general, to form a crosslinked matrix that will provide a hydrogel in an aqueous solution, one or more precursors are reacted. The precursors form crosslinks that will prevent the dissolution of the hydrogel in water. Precursors may be crosslinked via an ionic or covalent bond, a physical force, or other attraction. A covalent crosslink, however, will typically offer stability and predictability in reactant product architecture. To form covalently crosslinked matrices, the precursors are covalently crosslinked together. In general, precursors are joined to other precursors at two or more points, with each point being a linkage to the same or different polymers. Precursors with at least two reactive centers (for example, in free radical polymerization) can serve as crosslinkers since each reactive group can participate in the formation of a different growing polymer chain. In the case of functional groups without a reactive center, among others, crosslinking requires three or more such functional groups on at least one of the precursor types. For instance, many electrophilic-nucleophilic reactions consume the electrophilic and nucleophilic functional groups so that a precursor with three or more functional groups is needed for the precursors to form crosslinks. Such precursors thus may have three or more functional groups and may be crosslinked by precursors with two or more functional groups. These are described in some detail, below.

Hydrogels allowed to hydrate in aqueous media swell as they imbibe water. When equilibrium is reached, the total hydrogel weight, including the water, is constant, and the properties of the hydrogel at its equilibrium water content (EWC) can be measured; unless otherwise indicated, measurements at EWC are taken when a hydrogel is first allowed to freely swell and reaches a constant weight in solution, typically within a few hours. EWC is the water fraction of the hydrogel when fully swollen, i.e. at steady state. The EWC of a hydrolytically degradable hydrogel will gradually increase over time as hydrolysis increases the mesh size, which can be measured by molecular weight between crosslinks ($M_c$).

Precursor Materials

The crosslinked matrices that provide the hydrogel/xerogel are made from precursors. Precursors are chosen in consideration of the properties that are desired for the resultant hydrogel and in light of the structure at the time of formation, e.g., for compatibility with organic solvents if the crosslinked matrix is initially formed as an organogel. There are various suitable precursors for use in making the crosslinked matrices. The term precursor refers to those molecules crosslinked to form crosslinked matrices, e.g., a hydrogel or organogel matrix. While other materials might be present in the hydrogel or organogel, such as therapeutic agents, particles for delivery of agents, or fillers that are not crosslinked into the matrix, they are not precursors.

Crosslinked matrices may be formed from natural, synthetic, or biosynthetic polymers. Natural polymers may include glycosminoglycans, polysaccharides, and proteins. Some examples of glycosaminoglycans include dermatan sulfate, hyaluronic acid, the chondroitin sulfates, chitin, heparin, keratan sulfate, keratosulfate, and derivatives thereof. In general, the glycosaminoglycans are extracted from a natural source and purified and derivatized. However, they also may be synthetically produced or synthesized by modified microorganisms such as bacteria. These materials may be modified synthetically from a naturally soluble state to a partially soluble or water swellable or hydrogel state. This modification may be accomplished by various well-known techniques, such as by conjugation or replacement of ionizable or hydrogen bondable functional groups such as carboxyl and/or hydroxyl or amine groups with other more hydrophobic groups.

For example, carboxyl groups on hyaluronic acid may be esterified by alcohols to decrease the solubility of the hyaluronic acid. Such processes are used by various manufacturers of hyaluronic acid products to create hyaluronic acid based sheets, fibers, and fabrics that form hydrogels. Other natural polysaccharides, such as carboxymethyl cellulose or oxidized regenerated cellulose, natural gum, agar, agrose, sodium alginate, carrageenan, fucoidan, furcellaran, laminaran, hypnea, eucheuma, gum arabic, gum ghatti, gum karaya, gum tragacanth, locust beam gum, arbinoglactan, pectin, amylopectin, gelatin, hydrophilic colloids such as carboxymethyl cellulose gum or alginate gum crosslinked with a polyol such as propylene glycol, and the like, also form hydrogels upon contact with aqueous surroundings.

Synthetic gels or hydrogels may be biostable or biodegradable. Examples of biostable hydrophilic polymeric materials are poly(hydroxyalkyl methacrylate), poly(electrolyte complexes), poly(vinylacetate) cross-linked with hydrolysable or otherwise degradable bonds, and water-swellable N-vinyl lactams. Other hydrogels include hydrophilic hydrogels known as CARBOPOL®, an acidic carboxy polymer (Carbomer resins are high molecular weight, allylpentaerythritol-crosslinked, acrylic acid-based polymers, modified with C10-C30 alkyl acrylates), polyacrylamides, polyacrylic acid, starch graft copolymers, acrylate polymer, ester cross-linked polyglucan. Such hydrogels are described, for example, in U.S. Pat. No. 3,640,741 to Etes, U.S. Pat. No. 3,865,108 to Hartop, U.S. Pat. No. 3,992,562 to Denzinger et al., U.S. Pat. No. 4,002,173 to Manning et al., U.S. Pat. No. 4,014,335 to Arnold and U.S. Pat. No.

4,207,893 to Michaels, all of which are incorporated herein by reference, with the present specification controlling in case of conflict.

Crosslinked matrices may be made from precursors. The precursors are crosslinked with each other. Crosslinks can be formed by covalent bonds or physical bonds. Examples of physical bonds are ionic bonds, hydrophobic association of precursor molecule segments, and crystallization of precursor molecule segments. The precursors can be triggered to react to form a crosslinked hydrogel. The precursors can be polymerizable and include crosslinkers that are often, but not always, polymerizable precursors. Polymerizable precursors are thus precursors that have functional groups that react with each other to form matrices and/or polymers made of repeating units. Precursors may be polymers.

Some precursors thus react by chain-growth polymerization, also referred to as addition polymerization, and involve the linking together of monomers incorporating double or triple chemical bonds. These unsaturated monomers have extra internal bonds which are able to break and link up with other monomers to form the repeating chain. Monomers are polymerizable molecules with at least one group that reacts with other groups to form a polymer. A macromonomer (or macromer) is a polymer or oligomer that has at least one reactive group, often at the end, which enables it to act as a monomer; each macromonomer molecule is attached to the polymer by reaction the reactive group. Thus, macromonomers with two or more monomers or other functional groups tend to form covalent crosslinks. Addition polymerization is involved in the manufacture of, e.g., polypropylene or polyvinyl chloride. One type of addition polymerization is living polymerization.

Some precursors thus react by condensation polymerization that occurs when monomers bond together through condensation reactions. Typically, these reactions can be achieved through reacting molecules incorporating alcohol, amine or carboxylic acid (or other carboxyl derivative) functional groups. When an amine reacts with a carboxylic acid an amide or peptide bond is formed, with the release of water. Some condensation reactions follow a nucleophilic acyl substitution, e.g., as in U.S. Pat. No. 6,958,212, which is hereby incorporated by reference herein in its entirety to the extent it does not contradict what is explicitly disclosed herein. Some precursors react by a chain growth mechanism. Chain growth polymers are defined as polymers formed by the reaction of monomers or macromonomers with a reactive center. A reactive center is a particular location within a chemical compound that is the initiator of a reaction in which the chemical is involved. In chain-growth polymer chemistry, this is also the point of propagation for a growing chain. The reactive center is commonly radical, anionic, or cationic in nature, but can also take other forms. Chain growth systems include free radical polymerization, which involves a process of initiation, propagation and termination. Initiation is the creation of free radicals necessary for propagation, as created from radical initiators, e.g. organic peroxide molecules. Termination occurs when a radical reacts in a way that prevents further propagation. The most common method of termination is by coupling where two radical species react with each other forming a single molecule. Some precursors react by a step growth mechanism, and are polymers formed by the stepwise reaction between functional groups of monomers. Most step growth polymers are also classified as condensation polymers, but not all step growth polymers release condensates. Monomers may be polymers or small molecules. A polymer is a high molecular weight molecule formed by combining many smaller molecules (monomers) in a regular pattern. Oligomers are polymers having less than about 20 monomeric repeat units. A small molecule precursor generally refers to a precursor that is less than about 2000 Daltons. The precursors may thus be small molecules, such as acrylic acid or vinyl caprolactam, larger molecules containing polymerizable groups, such as acrylate-capped polyethylene glycol (PEG-diacrylate), or other polymers containing ethylenically-unsaturated groups. For example, see U.S. Pat. Nos. 4,938,763, 5,100,992 4,826,945, 4,741,872, 5,160,745, 5,410,016, 8,409,606, 8,383,161, 9,125,807, 9,205,150, US Pub. No. 2017/0143636, each of which is hereby incorporated by reference herein in its entirety to the extent it does not contradict what is explicitly disclosed herein.

In some embodiments, each precursor is multifunctional, meaning that it comprises two or more electrophilic or nucleophilic functional groups, such that a nucleophilic functional group on one precursor may react with an electrophilic functional group on another precursor to form a covalent bond. At least one of the precursors comprises more than two functional groups, so that, as a result of electrophilic-nucleophilic reactions, the precursors combine to form crosslinked polymeric products.

The precursors may have biologically inert and hydrophilic portions, e.g., a core. In the case of a branched polymer, a core refers to a contiguous portion of a molecule joined to arms that extend from the core, with the arms having a functional group, which is often at the terminus of the branch. A hydrophilic molecule, e.g., a precursor or precursor portion, has a solubility of at least 1 g/100 mL in an aqueous solution. A hydrophilic portion may be, for instance, a polyether, for example, polyalkylene oxides such as polyethylene glycol (PEG), polyethylene oxide (PEO), polyethylene oxide-co-polypropylene oxide (PPO), co-polyethylene oxide block or random copolymers, and polyvinyl alcohol (PVA), poly (vinyl pyrrolidinone) (PVP), poly (amino acids, dextran, or a protein. The precursors may have a polyalkylene glycol portion and may be polyethylene glycol based, with at least about 80% or 90% by weight of the polymer comprising polyethylene oxide repeats. The polyethers and more particularly poly (oxyalkylenes) or poly (ethylene glycol) or polyethylene glycol are generally hydrophilic. As is customary in these arts, the term PEG is used to refer to PEO with or without hydroxyl end groups.

A precursor may also be a macromolecule (or macromer), which is a molecule having a molecular weight in the range of a thousand to many millions. The hydrogel or organogel however, may be made with at least one of the precursors as a small molecule of about 1000 Da or less (alternatively: 2000 Da or less). The macromolecule, when reacted in combination with a small molecule (of about 1000 Da or less/2000 Da or less), e.g., is at least five to fifty times greater in molecular weight than the small molecule and is preferably less than about 60,000 Da; artisans will immediately appreciate that all the ranges and values within the explicitly stated ranges are contemplated. Examples of a precursor molecular weight is e.g., 500 to 500,000 Da; Artisans will immediately appreciate that all ranges and values between the explicitly stated bounds are contemplated, with, e.g., any of the following being available as an upper or lower limit: 500, 1000, 10,000, 20,000, 50,000, 80,000, 100,000, 200,000, 300,000, 400,000, 500,000 Da.

Synthetic precursors may be used. Synthetic refers to a molecule not found in nature or not normally found in a human. Some synthetic precursors are free of amino acids or free of amino acid sequences that occur in nature. Some synthetic precursors are polypeptides that are not found in nature or are not normally found in a human body, e.g., di-, tri-, or tetra-lysine. Some synthetic molecules have amino acid residues but only have one, two, or three that are contiguous, with the amino acids or clusters thereof being separated by non-natural polymers or groups. Polysaccharides or their derivatives are thus not synthetic. Synthetic polymers include polymers made from, or comprising, for example: poly(ethylene) oxide, polyethylene glycol, polyvinyl pyrrolidinone, polyacrylate, polymethylacrylate, polyalkylene oxide, methacrylic acid or other vinylic monomers, an acyl chloride, for example methacryloyl chloride, an isocyanate, or 2-isocyanatoethyl methacrylate an electrophilic poly(ethylene glycol) methacrylate (PEGMA). Free radical polymerization is, in general, accomplished with a vinylic or allylic group, including acrylates and methacrylates. A monomer may be polymerized by itself or with co-monomers that also undergo free radical polymerization. Examples of co-monomers include one or more of: acrylates, methacrylates, 2-hydroxyethyl methacrylate, hydroxypropyl methacrylate, n-butyl methacrylate, tert-butyl methacrylate, n-hexyl methacrylate, 2-methoxyethyl methacrylate, poly(hexanide) methacrylate, poly(hexanide) polyethylene oxide methacrylate, or alkyl derivatized poly(hexanide) methacrylate, heparin derivatized polyethylene oxide macromer, vinyl sulfonic acid monomer, monomers comprising poly(ethylene glycol), N-vinyl pyrrolidone monomers, 4-benzoylphenyl methacrylate allyl methyl carbonate, allyl alcohol, allyl isocyanate, methacryloyloxyethyl phosphorylcholine, glycerol monomethacrylate, and polymers containing phosphate and amine moieties. Various polymers include, for instance: hydrophilic polymers, hydrophobic polymers, polyalkylene oxides, polyethylene oxide, polyethers, and polyvinylpyrrolidone.

Alternatively, natural proteins or polysaccharides may be adapted to make crosslinked matrices for use as gels, hydrogels, or other materials for use with these methods, e.g., collagens, fibrin(ogen)s, albumins, alginates, hyaluronic acid, and heparins. These natural molecules may further include chemical derivitization, e.g., synthetic polymer decorations. The natural molecule may be crosslinked via its native nucleophiles or after it is derivitized with functional groups, e.g., as in U.S. Pat. Nos. 5,304,595, 5,324,775, 6,371,975, and 7,129,210, each of which is hereby incorporated by reference to the extent it does not contradict what is explicitly disclosed herein. Natural refers to a molecule found in nature. Natural polymers, for example proteins or glycosaminoglycans, e.g., collagen, fibrinogen, albumin, and fibrin, may be crosslinked using reactive precursor species with electrophilic functional groups. Natural polymers normally found in the body are proteolytically degraded by proteases present in the body. Such polymers may be reacted via functional groups such as amines, thiols, or carboxyls on their amino acids or derivitized to have activatable functional groups. While natural polymers may be used in hydrogels, their time to gelation and ultimate mechanical properties must be controlled by appropriate introduction of additional functional groups and selection of suitable reaction conditions, e.g., pH.

Precursors may be made with a hydrophobic portion provided that the resultant hydrogel retains the requisite amount of water, e.g., at least about 20%. In some cases, the precursor is nonetheless soluble in water because it also has a hydrophilic portion. In other cases, the precursor makes dispersion in the water (a suspension) but is nonetheless reactable to from a crosslinked material. Some hydrophobic portions may include a plurality of alkyls, polypropylenes, alkyl chains, or other groups. Some precursors with hydrophobic portions are sold under the trade names PLURONIC F68, JEFFAMINE, or TECTRONIC. A hydrophobic molecule or a hydrophobic portion of a copolymer or the like is one that is sufficiently hydrophobic to cause the molecule (e.g., polymer or copolymer) to aggregate to form micelles or microphases involving the hydrophobic domains in an aqueous continuous phase or one that, when tested by itself, is sufficiently hydrophobic to precipitate from, or otherwise change phase while within, an aqueous solution of water at pH from about 7 to about 7.5 at temperatures from about 30 to about 50° C.

Precursors may have, e.g., 2-100 arms, with each arm having a terminus, bearing in mind that some precursors may be dendrimers or other highly branched materials. An arm on a hydrogel precursor refers to a linear chain of chemical groups that connect a crosslinkable functional group to a polymer core. Some embodiments are precursors with between 3 and 300 arms; artisans will immediately appreciate that all the ranges and values within the explicitly stated ranges are contemplated, e.g., 4, 6, 8, 10, 12, 4 to 16, 8 to 100, 6, 8, 10, 12, or at least 6 arms.

Thus crosslinked matrices can be made, e.g., from a multi-armed precursor with a first set of functional groups and a low molecular-weight precursor having a second set of functional groups. For example, a six-armed or eight-armed precursor may have hydrophilic arms, e.g., polyethylene glycol, terminated with primary amines, with the molecular weight of the arms being about 1,000 to about 40,000; artisans will immediately appreciate that all ranges and values within the explicitly stated bounds are contemplated. Such precursors may be mixed with relatively smaller precursors, for example, molecules with a molecular weight of between about 100 and about 5000, or no more than about 800, 1000, 2000, or 5000 having at least about three functional groups, or, e.g., between about 3 to about 30 functional groups; ordinary artisans will appreciate that all ranges and values between these explicitly articulated values are contemplated, e.g., 3, 4, 5, 6, 7, 8, 9, 10, 11, 12, 13, 14, 15, 16, 20, 25, 30.

Precursors that are not dendrimers may be used. Dendritic molecules are highly branched radially symmetrical polymers in which the atoms are arranged in many arms and subarms radiating out from a central core. Dendrimers are characterized by their degree of structural perfection as based on the evaluation of both symmetry and polydispersity and require particular chemical processes to synthesize. Accordingly, an artisan can readily distinguish dendrimer precursors from non-dendrimer precursors. Dendrimers have a shape that is typically dependent on the solubility of its component polymers in a given environment, and can change substantially according to the solvent or solutes around it, e.g., changes in temperature, pH, or ion content.

Precursors may be dendrimers, e.g., as in U.S. Publication Nos. 2004/0086479 and 2004/0131582 and PCT Publication Nos. WO07005249, WO07001926 and WO06031358, or the U.S. counterparts thereof; dendrimers may also be useful as multifunctional precursors, e.g., as in U.S. Publication Nos. 2004/0131582 and 2004/0086479 and PCT Publication Nos. WO06031388 and WO06031388; each of which US and PCT applications are hereby incorporated by reference herein in its entirety to the extent they do not contradict what is explicitly disclosed herein. Dendrimers are highly ordered possess high surface area to volume ratios, and exhibit numerous end groups for potential functionalization. Embodiments include multifunctional precursors that are not dendrimers.

Some embodiments include a precursor that consists essentially of an oligopeptide sequence of no more than five residues, e.g., amino acids comprising at least one amine, thiol, carboxyl, or hydroxyl side chain. A residue is an amino acid, either as occurring in nature or derivatized thereof. The backbone of such an oligopeptide may be natural or synthetic. In some embodiments, peptides of two or more amino acids are combined with a synthetic backbone to make a precursor; certain embodiments of such precursors have a molecular weight in the range of about 100 to about 10,000 or about 300 to about 500 Artisans will immediately appreciate that all ranges and values between these explicitly articulated bounds are contemplated.

Precursors may be prepared to be free of amino acid sequences cleavable by enzymes present at the site of introduction, including free of sequences susceptible to attach by metalloproteinases and/or collagenases. Further, precursors may be made to be free of all amino acids, or free of amino acid sequences of more than about 50, 30, 20, 10, 9, 8, 7, 6, 5, 4, 3, 2, or 1 amino acids. Precursors may be non-proteins, meaning that they are not a naturally occurring protein and cannot be made by cleaving a naturally occurring protein and cannot be made by adding synthetic materials to a protein. Precursors may be non-collagen, non-fibrin, non-fibrinogen, and non-albumin, meaning that they are not one of these proteins and are not chemical derivatives of one of these proteins. The use of non-protein precursors and limited use of amino acid sequences can be helpful for avoiding immune reactions, avoiding unwanted cell recognition, and avoiding the hazards associated with using proteins derived from natural sources. Precursors can also be non-saccharides (free of saccharides) or essentially non-saccharides (free of more than about 5% saccharides by w/w of the precursor molecular weight. Thus a precursor may, for example, exclude hyaluronic acid, heparin, or gellan. Precursors can also be both non-proteins and non-saccharides.

Peptides may be used as precursors. In general, peptides with less than about 10 residues are preferred, although larger sequences (e.g., proteins) may be used. Artisans will immediately appreciate that every range and value within these explicit bounds is included, e.g., 1-10, 2-9, 3-10, 1, 2, 3, 4, 5, 6, or 7. Some amino acids have nucleophilic groups (e.g., primary amines or thiols) or groups that can be derivatized as needed to incorporate nucleophilic groups or electrophilic groups (e.g., carboxyls or hydroxyls). Polyamino acid polymers generated synthetically are normally considered to be synthetic if they are not found in nature and are engineered not to be identical to naturally occurring biomolecules.

Some matrices are made with a polyethylene glycol-containing precursor. Polyethylene glycol (PEG, also referred to as polyethylene oxide) refers to a polymer with a repeat group $(CH_2CH_2O)_n$, with n being at least 3. A polymeric precursor having a polyethylene glycol thus has at least three of these repeat groups connected to each other in a linear series. The polyethylene glycol content of a polymer or arm is calculated by adding up all of the polyethylene glycol groups on the polymer or arm, even if they are interrupted by other groups. Thus, an arm having at least 1000 MW polyethylene glycol has enough $CH_2CH_2O$ groups to total at least 1000 MW. As is customary terminology in these arts, a PEG polymer does not necessarily refer to a molecule that terminates in a hydroxyl group. Molecular weights are abbreviated in thousands using the symbol k, e.g., with 15K meaning 15,000 molecular weight, i.e., 15,000 Daltons. Polymeric components used herein are effectively monodisperse unless otherwise indicated; however artisans can readily adapt this disclosure to use polymers in terms of a weight average (Mw) or number average as may be convenient; in case of conflict, number average (Mn) molecular weights are to be used. NH2 refers to an amine termination. SG refers to succinimidyl glutarate. SS refers to succinimidyl succinate. SAP refers to succinimidyl adipate. SAZ refers to succinimidyl azelate. SS, SG, SAP and SAZ are succinimidyl esters that have an ester group that degrades by hydrolysis in water. Hydrolytically degradable or water-degradable thus refers to a material that would spontaneously degrade in vitro in an excess of water without any enzymes or cells present to mediate the degradation. A time for degradation refers to effective disappearance of the material as judged by the naked eye. Trilysine (also abbreviated LLL) is a synthetic tripeptide. Precursors and/or crosslinked matrices, hydrogels, organogels, gels, xerogels, as well as compositions that comprise the same, may be provided in a form that is pharmaceutically acceptable, meaning that it is highly purified and free of contaminants, e.g., pyrogens.

Material Structures

A gel's or hydrogel's crosslinked matrix structure and its constituent material composition, e.g., of the hydrogel's precursors determine its properties. Precursor factors include properties such as biocompatibility, water solubility, hydrophilicity, molecular weight, arm length, number of arms, functional groups, distance between crosslinks, degradability, and the like. The choice of reaction conditions also effects the crosslinked matrix's structure and properties, including choices of solvents, reaction schemes, reactant concentrations, solids content, and the like. There can be a variety of ways to achieve certain properties, or combination of properties. On the other hand some properties are in tension with each other, for instance brittleness may increase as a distance between crosslinks decreases or solids content increases. Strength may be increased by increasing the number of crosslinks but swelling may thereby be reduced. Artisans will appreciate that the same materials may be used to make matrices with a great range of structures that will have highly distinct mechanical properties and performance, such that the achievement of a particular property should not be merely assumed based on the general types of precursors that are involved.

Mesh size refers to the spacing between molecular strands of the hydrogel (and the crosslinked matrix), often expressed as the molecular weight between crosslinks ($M_c$). Mesh size affects several hydrogel properties, including a rate of diffusion of molecules. The mesh size is larger as the space between strands is increased. The crosslinking density can be controlled by the choice of the overall molecular weight of the precursor(s) used as crosslinker(s) and other precursor(s) and the number of functional groups available per precursor molecule. A lower molecular weight between crosslinks such as 200 will give much higher crosslinking density as compared to a higher molecular weight between crosslinks such as 500,000; artisans will immediately appreciate that all ranges and values within this range are contemplated and supported, e.g., 200 to 250,000, 500 to 400,000, 2,000 to 100,000, 10,000 to 80,000, 20,000 to 200,000 and so forth. The crosslinking density also may be controlled by the overall percent solids of the crosslinker and functional polymer solutions. Yet another method to control crosslink density is by adjusting the stoichiometry of nucleophilic functional groups to electrophilic functional groups. A one to one ratio leads to the highest crosslink density. Precursors with longer distances between crosslinkable sites form gels that are generally softer, more compliant, and more elastic. Thus an increased length of a water-soluble segment, such as a polyethylene glycol, tends to enhance elasticity to produce desirable physical properties. Thus certain embodiments are directed to precursors with water soluble segments having molecular weights in the range of 1,000 to 200,000; artisans will immediately appreciate that all the ranges and values within the explicitly stated ranges are contemplated, e.g. 5,000 to 35,000. The solids content of the hydrogel can affect its mechanical properties and biocompatibility and reflects a balance between competing requirements. A relatively low solids content is generally useful, e.g., between about 2.5% to about 20%, including all ranges and values there between, e.g., about 2.5% to about 10%, about 5% to about 15%, or less than about 15%.

Functional Groups

The precursors for covalent crosslinking have functional groups that react with each other to form the material via covalent bonds, either outside a patient, or in situ. The functional groups generally are polymerizable, a broad category that encompasses free radical, addition, and condensation polymerization and also groups for electrophile-nucleophile reactions. Various aspects of polymerization reactions are discussed in the precursors section herein.

Thus in some embodiments, precursors have a polymerizable group that is activated by photoinitiation or redox systems as used in the polymerization arts, or electrophilic functional groups, for instance: carbodiimidazole, sulfonyl chloride, chlorocarbonates, n-hydroxysuccinimidyl ester, succinimidyl ester or sulfasuccinimidyl esters, or as in U.S. Pat. No. 5,410,016 or 6,149,931, each of which are hereby incorporated by reference herein in its entirety to the extent they do not contradict what is explicitly disclosed herein. The nucleophilic functional groups may be, for example, amine, hydroxyl, carboxyl, and thiol. Another class of electrophiles are acyls, e.g., as in U.S. Pat. No. 6,958,212, which describes, among other things, Michael addition schemes for reacting polymers.

Certain functional groups, such as alcohols or carboxylic acids, do not normally react with other functional groups, such as amines, under physiological conditions (e.g., pH 7.2-11.0, 37° C.). However, such functional groups can be made more reactive by using an activating group such as N-hydroxysuccinimide. Certain activating groups include carbonyldiimidazole, sulfonyl chloride, aryl halides, sulfo-succinimidyl esters, N-hydroxysuccinimidyl ester, succinimidyl ester, epoxide, aldehyde, maleimides, imidoesters and the like. The N-hydroxysuccinimide esters or N-hydroxysulfosuccinimide (NHS) groups are useful groups for crosslinking of proteins or amine-containing polymers, e.g., amino terminated polyethylene glycol. An advantage of an NHS-amine reaction is that the reaction kinetics are favorable, but the gelation rate may be adjusted through pH or concentration. The NHS-amine crosslinking reaction leads to formation of N-hydroxysuccinimide as a side product. Sulfonated or ethoxylated forms of N-hydroxysuccinimide have a relatively increased solubility in water and hence their rapid clearance from the body. An NHS-amine crosslinking reaction may be carried out in aqueous solutions and in the presence of buffers, e.g., phosphate buffer (pH 5.0-7.5), triethanolamine buffer (pH 7.5-9.0), or borate buffer (pH 9.0-12), or sodium bicarbonate buffer (pH 9.0-10.0). Aqueous solutions of NHS based crosslinkers and functional polymers preferably are made just before the crosslinking reaction due to reaction of NHS groups with water. The reaction rate of these groups may be delayed by keeping these solutions at lower pH (pH 4-7). Buffers may also be included in the hydrogels introduced into a body.

In some embodiments, each precursor comprises only nucleophilic or only electrophilic functional groups, so long as both nucleophilic and electrophilic precursors are used in the crosslinking reaction. Thus, for example, if a crosslinker has nucleophilic functional groups such as amines, the functional polymer may have electrophilic functional groups such as N-hydroxysuccinimides. On the other hand, if a crosslinker has electrophilic functional groups such as sulfo-succinimides, then the functional polymer may have nucleophilic functional groups such as amines or thiols. Thus, functional polymers such as proteins, poly(allyl amine), or amine-terminated di- or multifunctional poly(ethylene glycol) can be used.

One embodiment has reactive precursor species with 2 to 16 nucleophilic functional groups each and reactive precursor species with 2 to 16 electrophilic functional groups each; artisans will immediately appreciate that all the ranges and values within the explicitly stated ranges are contemplated, for instance 2, 3, 4, 5, 6, 7, 8, 9, 10, 11, 12, 13, 14, 15, or 16 groups.

The functional groups may be, e.g., electrophiles reactable with nucleophiles, groups reactable with specific nucleophiles, e.g., primary amines, groups that form amide bonds with materials in the biological fluids, groups that form amide bonds with carboxyls, activated-acid functional groups, or a combination of the same. The functional groups may be, e.g., a strong electrophilic functional group, meaning an electrophilic functional group that effectively forms a covalent bond with a primary amine in aqueous solution at pH 9.0 at room temperature and pressure and/or an electrophilic group that reacts by a of Michael-type reaction. The strong electrophile may be of a type that does not participate in a Michaels-type reaction or of a type that participates in a Michaels-type reaction.

A Michael-type reaction refers to the 1, 4 addition reaction of a nucleophile on a conjugate unsaturated system. The addition mechanism could be purely polar, or proceed through a radical-like intermediate state(s); Lewis acids or appropriately designed hydrogen bonding species can act as catalysts. The term conjugation can refer both to alternation of carbon-carbon, carbon-heteroatom or heteroatom-heteroatom multiple bonds with single bonds, or to the linking of a functional group to a macromolecule, such as a synthetic polymer or a protein. Michael-type reactions are discussed in detail in U.S. Pat. No. 6,958,212, which is hereby incorporated by reference herein in its entirety for all purposes to the extent it does not contradict what is explicitly disclosed herein.

Examples of strong electrophiles that do not participate in a Michaels-type reaction are: succinimides, succinimidyl esters, or NHS-esters. Examples of Michael-type electrophiles are acrylates, methacrylates, methylmethacrylates, and other unsaturated polymerizable groups.

Initiating Systems

Some precursors react using initiators. An initiator group is a chemical group capable of initiating a free radical polymerization reaction. For instance, it may be present as a separate component, or as a pendent group on a precursor. Initiator groups include thermal initiators, photoactivatable initiators, and oxidation-reduction (redox) systems. Long wave UV and visible light photoactivatable initiators include, for example, ethyl eosin groups, 2, 2-dimethoxy-2-phenyl acetophenone groups, other acetophenone derivatives, thioxanthone groups, benzophenone groups, and camphorquinone groups. Examples of thermally reactive initiators include 4, 4' azobis (4-cyanopentanoic acid) groups, and analogs of benzoyl peroxide groups. Several commercially available low temperature free radical initiators, such as V-044, available from Wako Chemicals USA, Inc., Richmond, Va., may be used to initiate free radical crosslinking reactions at body temperatures to form hydrogel coatings with the aforementioned monomers.

Metal ions may be used either as an oxidizer or a reductant in redox initiating systems. For example, ferrous ions may be used in combination with a peroxide or hydroperoxide to initiate polymerization, or as parts of a polymerization system. In this case, the ferrous ions would serve as a reductant. Alternatively, metal ions may serve as an oxidant. For example, the ceric ion (4+ valence state of cerium) interacts with various organic groups, including carboxylic acids and urethanes, to remove an electron to the metal ion, and leave an initiating radical behind on the organic group. In such a system, the metal ion acts as an oxidizer. Potentially suitable metal ions for either role are any of the transition metal ions, lanthanides and actinides, which have at least two readily accessible oxidation states. Particularly useful metal ions have at least two states separated by only one difference in charge. Of these, the most commonly used are ferric/ferrous; cupric/cuprous; ceric/cerous; cobaltic/cobaltous; vanadate V vs. IV; permanganate; and manganic/manganous. Peroxygen containing compounds, such as peroxides and hydroperoxides, including hydrogen peroxide, t-butyl hydroperoxide, t-butyl peroxide, benzoyl peroxide, cumyl peroxide may be used.

An example of an initiating system is the combination of a peroxygen compound in one solution, and a reactive ion, such as a transition metal, in another. In this case, no external initiators of polymerization are needed and polymerization proceeds spontaneously and without application of external energy or use of an external energy source when two complementary reactive functional groups containing moieties interact at the application site.

Visualization Agents

A visualization agent may be present in the crosslinked matrix and the hydrogel; it reflects or emits light at a wavelength detectable to a human eye so that a user applying the hydrogel could observe the object without a machine aid when it contains an effective amount of the agent. Chemicals that require a machine aid for imaging are referred to as imaging agents herein, and examples include: radioopaque contrast agents and ultrasound contrast agents. Some biocompatible visualization agents are FD&C BLUE #1, FD&C BLUE #2, and methylene blue. These agents are preferably present in the final electrophilic-nucleophilic reactive precursor species mix at a concentration of more than 0.05 mg/ml and preferably in a concentration range of at least 0.1 to about 12 mg/ml, and more preferably in the range of 0.1 to 4.0 mg/ml, although greater concentrations may potentially be used, up to the limit of solubility of the visualization agent. Visualization agents may be covalently linked to the molecular network of the xerogel/hydrogel, thus preserving visualization after application to a patient until the hydrogel hydrolyzes to dissolution. Visualization agents may be selected from among any of the various non-toxic colored substances suitable for use in medical implantable medical devices, such as FD&C BLUE dyes 3 and 6, eosin, methylene blue, indocyanine green, or colored dyes normally found in synthetic surgical sutures. Reactive imaging agents such as NHS-fluorescein can be incorporated into the molecular network of the xerogel/hydrogel. Fluorescein is typically an imaging agent but may be visualized without machine aid when present in sufficient concentration. The level of fluorescein can be manipulated from none (essentially not visible) to a small quantity (visible with fluorescence) to a larger quantity (visible as yellow without a machine aid). The visualization agent may be present with either reactive precursor species, e.g., a crosslinker or functional polymer solution. The preferred colored substance may or may not become chemically bound to the hydrogel.

For instance, a fluorescent molecule that illuminates when excited with a light source, such as a slit lamp, are useful for an investigator to confirm presence of a depot containing the fluorescent molecule. For instance, fluorescein can be illuminated with a blue light source.

Biodegradation

If it is desired that a biocompatible crosslinked matrix be biodegradable, one or more precursors having biodegradable linkages (or just one biodegradable linkage, for example an ester) present in between the functional groups may be used. The biodegradable linkage optionally also may serve as the water soluble core of one or more of the precursors used to make the matrix. For each approach, biodegradable linkages may be chosen such that the resulting biodegradable biocompatible crosslinked polymer will degrade or be absorbed in a desired period of time.

A crosslinked matrix may be formed so that, upon hydration in physiological solution, a gel or hydrogel is formed that is water-degradable, as measurable by the gel or hydrogel losing its mechanical strength and eventually dissipating in vitro in an excess of water by hydrolytic degradation of water-degradable groups. This test is predictive of hydrolytically-driven dissolution in vivo, a process that is in contrast to cell or protease-driven degradation. Significantly, however, polyanhydrides or other conventionally-used degradable materials that degrade to acidic components tend to cause inflammation in tissues. The hydrogels, however, may exclude such materials, and may be free of polyanhydrides, anhydride bonds, or precursors that degrade into acid or diacids. Hydrogels, when covalently crosslinked, do not dissolve in water. As they degrade, however, the molecular network breaks down, releasing soluble subunits. Eventually the molecular network disintegrates and the hydrogel is no longer visible, at which point the hydrogel is referred to as having been dissolved. The term hydrolyzable linkages refers to linkage capable by cleavage of a water molecule under physiological conditions.

Delivery times of up to about 2 years at a therapeutically effective dose in a human eye are practical for a single hydrogel depot; all times from 10 days to 2 years are contemplated; artisans will immediately appreciate that all ranges and values between the explicitly stated bounds are contemplated, with, e.g., any of the following being available as an upper or lower limit: e.g., 10, 20, 30, 40 50, 60 70, 80, 90, 100, 120, 150 days, e.g., 1, 2, 3, 4, 5, 6, 7, 8, 9, 10, 11, 12 13, 14, 15, 16, 17, 18, 19, 20, 21, 22, 23, or 24 months. One embodiment for lengthy times is to choose biodegradable linkages for a matrix of a depot that degrade slowly. The degradation of the hydrogel matrix is controlled by several factors: 1) The hydrophobicity of the carbon chain length proximate to the ester which meters the rate of hydrolysis in the presence of water. A shorter carbon chain (such as a 4 hydrocarbon chain adipate) is more hydrophilic and will cause ester hydrolysis at a faster rate compared to a longer more hydrophobic carbon chain (e.g., a 7 carbon chain); 2) For a given precursor concentration, the arm length of the precursor chains within the hydrogel network regulates the number of biodegradable linkages. More linkages promote longer persisting hydrogel; 3) A higher precursor concentration increases the number of linkages within the hydrogel network and consequently its persistence. Therefore the matrix of a depot can be made to persist for long duration by selecting more hydrophobic groups proximate to the ester in combination with short arm length multi-arm PEGs prepared at high PEG concentrations.

For example, electrophilic groups such as SG (succinimidyl glutarate), SS (succinimidyl succinate), SC (succinimidyl carbonate), SAP (succinimidyl adipate) or SAZ (succinimidyl azelate) may be used and have esteric linkages that are hydrolytically labile. Longer linear hydrophobic linkages such as pimelate, suberate, azelate or sebacate linkages may also be used, with these linkages being less degradable than succinate, glutarate or adipate linkages. Branched, cyclic or other hydrophobic linkages may also be used. PEGs, polysaccharides, and other precursors may be prepared with these groups. The crosslinked hydrogel degradation may proceed by the water-driven hydrolysis of the biodegradable segment when water-degradable materials are used. Polymer segments that include ester linkages may also be included to provide a desired degradation rate, with groups being added or subtracted near the esters to increase or decrease the rate of degradation. Thus it is possible to construct a hydrogel with a desired degradation profile, from a few days to many months, using a degradable segment. If polyglycolide is used as the biodegradable segment, for instance, a crosslinked polymer could be made to degrade in about 1 to about 30 days depending on the crosslinking density of the network. Similarly, a polycaprolactone based crosslinked network can be made to degrade in about 1 to about 8 months. The degradation time generally varies according to the type of degradable segment used, in the following order: polyglycolide<polylactide<polytrimethylene carbonate<polycaprolactone. Some embodiments include precursors that are free of adjacent ester groups and/or have no more than one ester group per arm on one or more of the precursors: control of the number and position of the esters can assist in uniform degradation of the hydrogel.

The molecular network, also referred to as the matrix, formed by a hydrophilic polymer, for example polyethylene glycols (PEGs), can be represented by the following crosslinking reaction schematic:

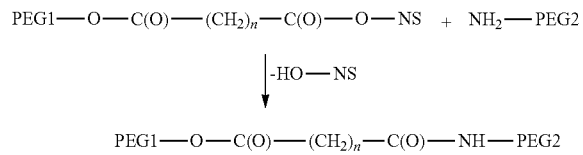

Where PEG1 and PEG2 are multi-armed polyethylene glycols with only one arm shown, but connectivity to the network is through the other arms on PEG1 and PEG2. The symbol S is a cyclic succinate group bonded to the nitrogen (N) to form a succinimide group, NS. Note that PEG2 can be substituted with any multi-functional primary amine, e.g. trilysine, which bears four primary amine groups. The crosslinking occurs when the nucleophilic primary amine supplants the N-hydroxysuccinimide (HO—NS) leaving group to form the amide crosslink bond. The length of repeating methylene $((CH_2)_n)$ groups control the rate of hydrolysis of the adjacent ester linkage when exposed to water. The hydrolysis reaction is depicted in the following schematic:

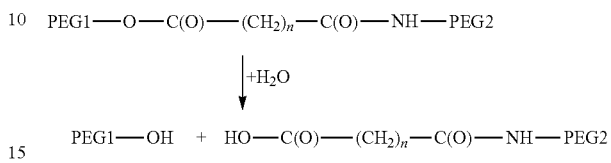

Here the crosslink is severed by addition of a water molecule at the ester to disengage the PEGs from each other. The PEG molecules themselves are not altered, other than the shift of the end groups from PEG1 to PEG2. This crosslink cleavage reaction occurs throughout the molecular network, eventually yielding the starting PEG1 and PEG2 molecules unchanged, except for the end group shift. Hydrolysis products of these reactions are non-toxic.

The length of the methylene chain $((CH_2)_n)$ controls the rate of ester hydrolysis by controlling the hydrophobicity of the domain directly connected to the ester linkage. As the hydrophobicity increases with longer methylene chains, the rate of hydrolysis decreases, due to increasing hindrance of a water accessibility to the ester. Thus, in the structure PEG1-O—C(O)—$(CH_2)_n$—C(O)—NH-PEG2, the following list exemplifies the effect of lengthening methylene chains on degradation.

| Rate | Methylene Chain Length (n) | Linkage Name | End Group Name |
|---|---|---|---|
| 1 (Fast) | 2 | succinic | SS |
| 2 | 3 | glutaric | SG |
| 3 | 4 | adipic | SAP |
| 4 (slow) | 7 | azeleic | SAZ |

Also, the rate of crosslinking for these linkages follows the same order, in this case the approach of the primary amine to the NHS ester is hindered by the longer methylene chains. In the standardized nomenclature for the precursor ester polymers, the rates of both crosslinking and hydrolysis is as follows: PEG SS>PEG SG>PEG SAP>PEG SAZ. The following table lists some example hydrogels and their degradation times.

| Hydrogel | Approximate Time to Disappearance |
|---|---|
| 8a15K PEG SS + trilysine | 5-7 days |
| 4a 20K PEG SG + trilysine | 6-8 weeks |
| 4a20K PEG SAP + 8a20K PEG $NH_2$ | 4 months |
| 4a20K PEG SAZ + 8a20K PEG $NH_2$ | 8 months |

Artisans can follow guidance herein to extend these times to accommodate delivery times for a week to two years, including times to accommodate desired IRR deign factors as described herein.

Agents may be in biodegradable vehicles, e.g., microparticles. Biodegradable vehicles in which the active agent may be present include: encapsulation vehicles, such as microparticles, microspheres, microbeads, micropellets, where the active agent is encapsulated in a degradable material, e.g. a bioerodable or biodegradable polymer such as polymers and copolymers of: poly(anhydride), poly(hydroxy acid)s, poly(lactone)s, poly(trimethylene carbonate), poly(glycolic acid), poly(lactic acid) (PLA), poly(lactic acid)-co-poly(glycolic acid) (PLGA), poly(orthocarbonate), poly(caprolactone), crosslinked biodegradable hydrogel networks like fibrin glue or fibrin sealant, caging and entrapping molecules, like cyclodextrin, molecular sieves and the like. Microspheres made from polymers and copolymers of poly (lactone)s and poly (hydroxy acid) are particularly preferred as biodegradable encapsulation vehicles. The amount of agent and degradable material may be chosen in light of the particular intended use of the particle and the agent, including a time of degradation and rate of release. A content of the particle may range from, for example, 0.5 to about 80 percent by weight or volume. Artisans reading this disclosure will understand that the therapeutic agent release from a depot described herein can be modulated by adjusting the microparticle formulation to regulate the biodegradation rates of the microparticle materials encapsulating the agent.

Figure 7:
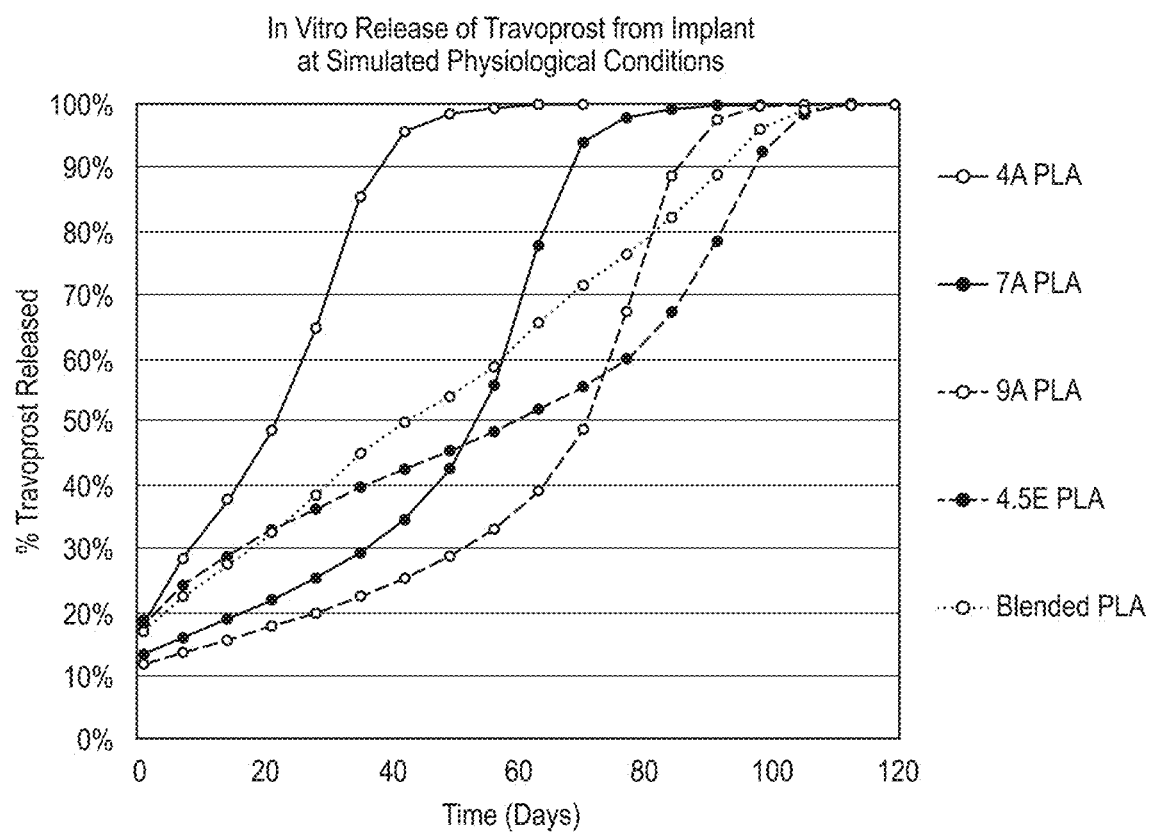
FIG. 7 is a plot of data showing release of an agent under simulated physiological conditions.
Figures 8A, 8B, 8C, 8D:
FIGS. 8A-8D is an image of a composite depot being delivered to an anterior chamber, arranged sequentially in time as indicated.

For example, in the context of PLA and PLGA formulations, this degradation modulation can occur through adjustment of: co-polymer lactide:glycolide ratios; amorphous (D,L-lactide) or crystalline (L-lactide) polymer forms; polymer molecular weights; ester or acid end group chemistries; microparticle size; and agent loading within the microparticles. Furthermore, these microparticles can be blended when necessary to achieve tailored drug release rates. FIG. 7 demonstrates a range of release of agents (travoprost) from the depots from 1.5 to 5 months for various formulations made according to the processes of Example 1. Formulations with higher glycolide contents, acid end groups, lower molecular weights, smaller microparticles, amorphous forms and higher drug loads yield faster drug release rates. Formulations with less (or none) glycolide content, ester end groups, higher molecular weights, larger microparticles, crystalline forms and lower drug loads yield slower drug release rates. Marketed sustained release formulations exist having demonstrated shorter or longer durations of drug release. For example, LUPRON DEPOT used in the treatment of prostate cancer can be formulated either at a dose of 7.5 mg for 1 month or 45 mg PLA for 6 months using the degradation-rate selection guidance described above. In vivo biodegradation persistence of crystalline, high molecular weight, ester end group polylactides have been demonstrated up to 3 years for medical devices.

A biodegradable linkage in an organogel and/or xerogel and/or hydrogel and/or gel and/or precursor may be water-degradable or enzymatically degradable. Illustrative water-degradable biodegradable linkages include polymers, copolymers and oligomers of glycolide, dl-lactide, 1-lactide, dioxanone, esters, carbonates, and trimethylene carbonate. Illustrative enzymatically biodegradable linkages include peptidic linkages cleavable by metalloproteinases and collagenases. Examples of biodegradable linkages include polymers and copolymers of poly(hydroxy acid)s, poly (orthocarbonate)s, poly(anhydride)s, poly(lactone)s, poly (aminoacid)s, poly(carbonate)s, and poly(phosphonate)s.

Particles may be chosen to degrade over long periods of time so that high doses of an agent may be introduced and slowly released. For instance, bimatoprost used in the therapy of glaucoma was delivered via intracameral administration and was demonstrated to provide IOP reduction up to 4 months in clinical studies (Charters, L. Ophthalmology Times, Aug. 1, 2016; bimatoprost has a 10 µg dose). Certain embodiments herein are directed to use of microparticles loaded with travoprost acid that is approximately 7 to 50 times more potent than bimatoprost for the human trabecular meshwork receptors. Due to the difference in potency, bimatoprost (LUMIGAN) is conventionally administered topically once a day at a strength of 0.03%, whereas travoprost (TRAVATAN) is conventionally administered at a lower strength 0.004%. Due to the higher potency of the travoprost acid for the prostaglandin receptors a low dose (10-100 µg) delivered over two years from microparticles fabricated with ester end group high molecular weight polylactides or from polycaprolactone will deliver therapeutic quantities sufficient for efficacy and IOP reduction.

Formation of Depots S

The composite depots are made by a process that includes forming a crosslinked matrix from a precursor. The term "a" means one or more. The term depot encompasses a composite depot. A hydrogel or organogel or a xerogel has a matrix that is formed by crosslinking precursors with each other to create the hydrogel or organogel, which may subsequently be changed into a xerogel. Agents, particles, or other materials can be in the hydrogels or xerogels but are not part of the matrix. The composite depots have the hydrogel and particles comprising agents that are released from the particles. The particles provide a release matrix. The release matrix refers to the materials that make the particles around the therapeutic agent; the agents are released from the release matrix. Formation of hydrogel or organogel matrices is described above. Such matrices, and the agents within them, can be made in molds, cast, made on a surface, or otherwise prepared to achieve a desired size and shape for composite depot or other depot. A depot may be made directly or from a larger material by machining, cutting, dicing, or otherwise shaping the large material into the desired size and shape.

The matrices may undergo stretching or shrinking before, during, or after formation. For instance, in FIG. 2 a matrix is initially formed as a hydrogel or organogel. In one embodiment, this original matrix is then stretched to a longer length. Original refers to the matrix at the time of formation. In this embodiment and in the other embodiments, the solvent may be removed before, during, or after stretching to form a xerogel. In another embodiment, the original matrix is held at a constant length while it is dried and allowed to shrink it other dimensions. The xerogel may subsequently be further processed, e.g., by stretching. In another embodiment, the original matrix is dried and allowed to shrink in all dimensions and a resultant xerogel is used in the resultant condition or is further processed, e.g., is stretched to increase its length.

Figure 3:
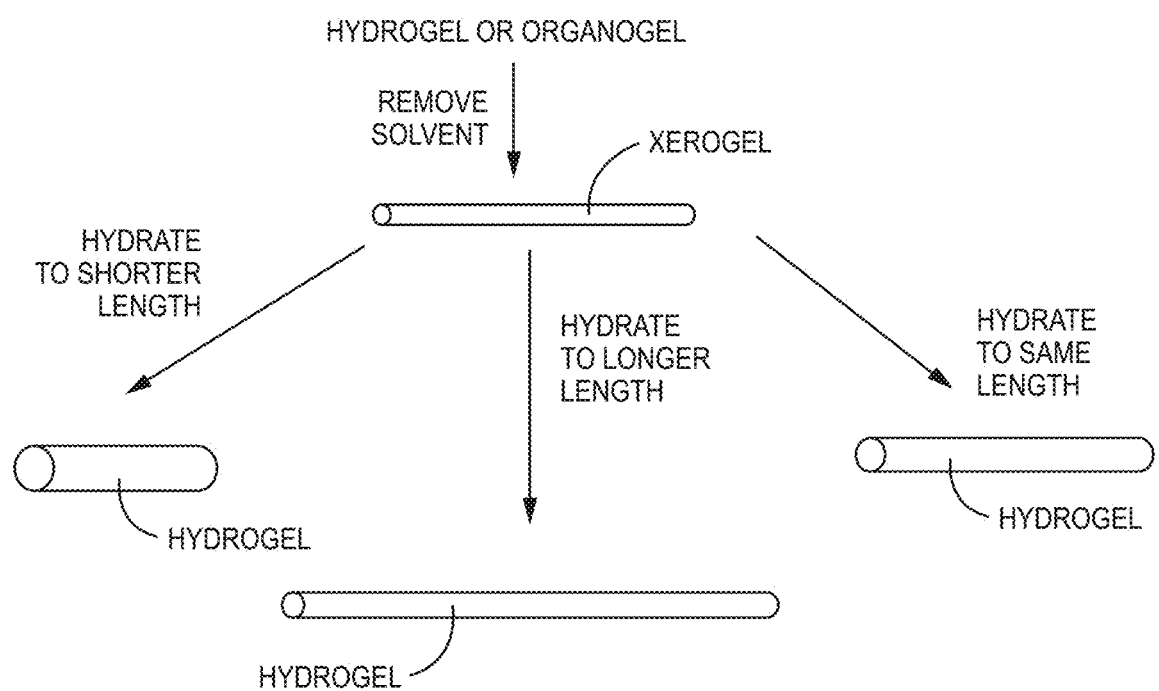
FIG. 3 depicts formation of a xerogel and its hydration in aqueous media.

In FIG. 3 a xerogel prepared from a matrix, e.g., hydrogel or organogel, undergoes a change in shape after it has been exposed to physiological fluid or other aqueous media. For example, it may decrease length and increase in other dimensions, increase length, or have the same length. Stretching of the matrix can be used to align crosslinked matrices to create a network of crosslinked precursors that will result in an alignment or other orientation that drives a change in dimensions. US Pub. No. 2017/0143636 describes various materials and methods for controlling changes in shape in response to exposure to an aqueous, e.g., physiological, fluid.

Figure 5:
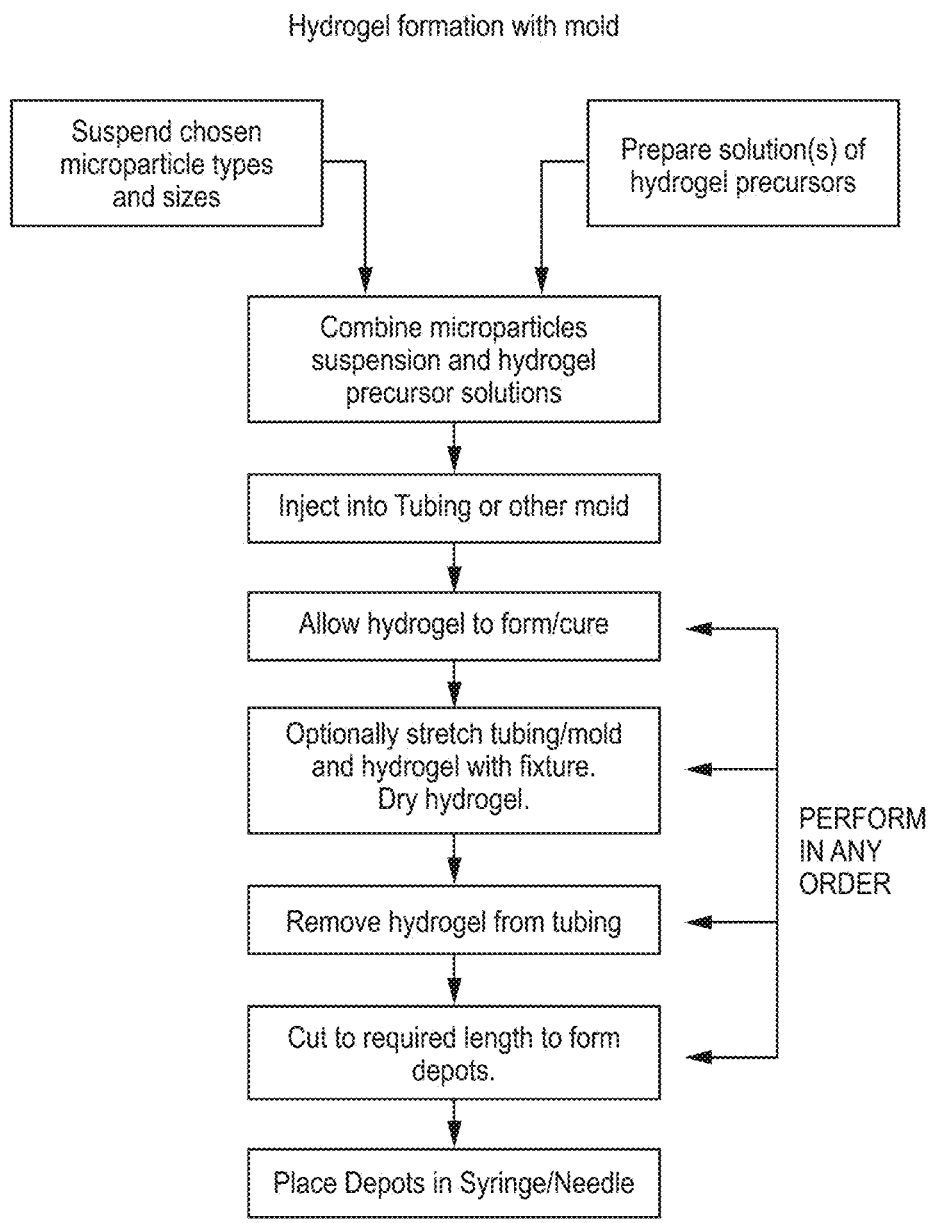
FIG. 5 depicts a process for making crosslinked matrices for use in delivery of a therapeutic agent.

FIG. 5 depicts an example of a process of making a crosslinked matrix that contains particles that have agents, forming a composite depot. Particles of desired size and characteristics are selected and combined with a hydrogel precursor; this mixture is introduced into a mold, e.g., a tube, where the precursor (or precursors) react (spontaneously or are initiated to react) to form a crosslinked matrix with embedded, drug-loaded microparticles. Stretching or other processing of the matrix is performed, the matrix is dried and cut to size, either before or after removal from the mold. The hydrogel can be stretched or otherwise processed before, during, or after drying. The resultant depotss may be further processed, e.g., packaged, packed in kits, or placed into applicators.

Figure 6:
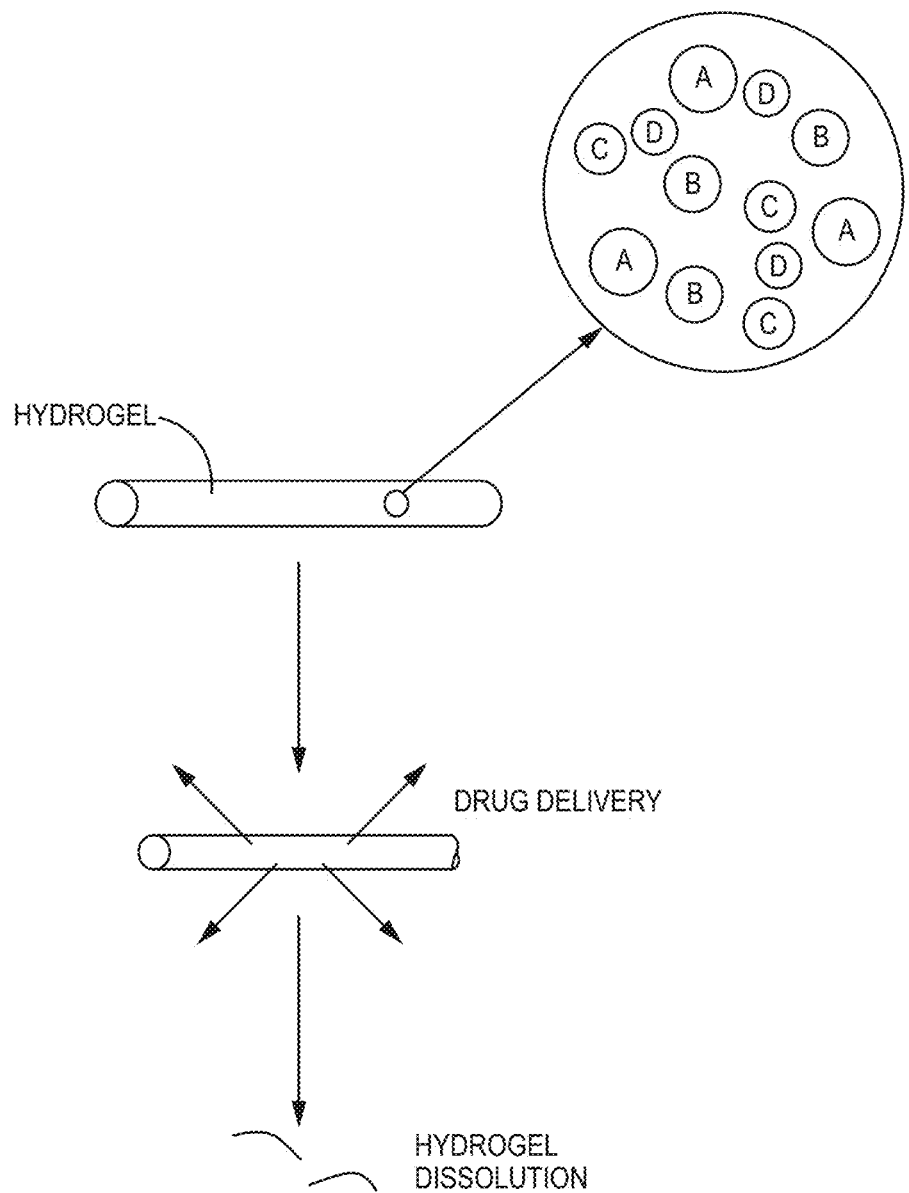
FIG. 6 depicts a crosslinked matrix with variously sized agent-containing particles.

FIG. 6 depicts a composite depot. A crosslinked matrix forms a hydrogel in aqueous solution. The hydrogel contains a plurality of particle collections. The particles are embedded in the hydrogel, which surrounds them. The collections each have properties independently chosen from size, material, and agent. Collections A, B, C, and D are depicted, with the collections having different sizes. The degradation rates of the members of the collection are different and/or the agents they release are different. The microparticles deliver the drugs and the hydrogel and microparticles dissolve.

The depots are integral to safety and efficacy of the therapeutic agent. The agent must be released at a controlled rate to avoid toxicity and to provide an effective concentration during its time of intended use. The depots are pharmaceutically acceptable, with appropriate chemistries and materials being chosen to provide for suitable degradation rates, sterilization, avoidance of unwanted side reactions, and degrade to yield non-toxic degradation products. The degradation products should themselves be nontoxic and also water soluble so that they may be cleared from the eye or other location in the body by fluid flow from the local site of administration and exposed to the body's natural processes for clearing molecules, such as the renal system. The depot is a hydrogel which provides biocompatibility to avoid undue reaction foreign body reactions or other unwanted cellular engagement. Artisans are accustomed to determining toxicity levels so as to determine that a product is non-toxic. Depots and/or matrices and/or xerogels and/or particles may be sterilized by irradiation or other suitable means.

Loading with Agents; Preparation of Particles

Crosslinked hydrogel matrices are loaded with an agent or agents that are disposed indirectly in the hydrogel. Indirect loading is preferable so that release can be controlled by degradation of a release matrix rather than the hydrogel.

An indirect loading process is, e.g., placing an agent in particulate matrices or a reservoir and forming a hydrogel or organogel matrix around them, so that the agent is inside the particle or reservoir and, at the time of formation, is not in direct contact with the hydrogel or organogel matrix. In some embodiments, the agent or agents are present in a separate phase when precursors are reacted. The separate phase could be oil (oil-in water emulsion), or an immiscible solvent, a liposome, a micelle, a biodegradable vehicle, or the like. Biodegradable materials and particles are discussed above.

The therapeutic agent or encapsulated therapeutic agent may be present in solution or suspended form, including directly in a matrix or indirectly, e.g., in a microparticle. Some agents are highly soluble while others are effectively insoluble in aqueous solution and can form their own phase when exposed to aqueous solvent. Further, a particle may be made that is free of one or more of: binders, non-peptidic polymers, surfactants, oils, fats, waxes, hydrophobic polymers, polymers comprising alkyl chains longer than 4 $CH_2$ groups, phospholipids, micelle-forming polymers, micelle-forming compositions, amphiphiles, polysaccharides, polysaccharides of three or more sugars, fatty acids, and lipids. Lyophilized, spray dried or otherwise processed proteins are often formulated with sugars such as trehalose to stabilize the protein through the lyophilization or other processes used to prepare the proteins. These sugars may be allowed to persist in the particle throughout the organogel/xerogel process. The particles may be made to comprise between about 20% and about 100% (dry w/w) agent; artisans will immediately appreciate that all the ranges and values within the explicitly stated ranges are contemplated, e.g., about 50% to about 80% or at least 90% or at least about 99%. An agent may be prepared as a powder, with the powder particle size being chosen in light of the size of the depot or hydrogel/organogel/xerogel particle. Organic solvents for the agents may be chosen so that the agents are not solvated by the organic solvents and are compatible with the protein. Another factor is oxygen, and elimination of oxygen is helpful in processing to avoid denaturation of sensitive agents. Another factor is chemical reactions. In some embodiments reactions with precursors are avoided by keeping the agents in a separate phase during formation of the original matrix, by encapsulation in a particle, or by keeping an agent in a solid phase and free of solvents that dissolve the agent until such time as the depot is used.

A gel or organogel or hydrogel may be formed and then reduced to particles that are subsequently treated to remove the organic or aqueous solvent or solvents to form a xerogel. For an injectable form, the organogel or hydrogel can be macerated, homogenized, extruded, screened, chopped, diced, or otherwise reduced to a particulate form. Alternatively, the organogel or hydrogel can be formed as a droplet or a molded article containing the suspended protein particles. One process for making such particles involves creation of a material that is broken up to make the particles. One technique involves preparing the organogel or hydrogel with protein particles and grinding it, e.g., in a ball mill or with a mortar and pestle. The matrix may be chopped or diced with knives or wires. Or the matrix may be cut-up in a blender or homogenizer. Another process involves forcing the organogel through a mesh, collecting the fragments, and passing them through the same mesh or another mesh until a desired size is reached.

The particles may be separated into collections with a desired size range and distribution of sizes by a variety of methods. Very fine control of sizing is available, with sizes ranging from 1 micron to several mm, and with a mean and range of particles sizes being controllable with a narrow distribution. Artisans will immediately appreciate that all the ranges and values within the explicitly stated ranges are contemplated, e.g., from about 1 to about 10 μm or from about 1 to about 30 μm. About 1 to about 500 microns is another such range that is useful, with sizes falling throughout the range and having a mean sizing at one value within the range, and a standard deviation centered around the mean value, e.g., from about 1% to about 100%. A simple method for sizing particles involves using custom-made or standardized sieve mesh sizes.

The term particle is used broadly herein to refer to vehicles of delivery that are small, meaning less than about 0.1 mm in the largest dimension. A particle can have any shape, e.g., spherical, oblate, ellipsoidal, rod, disc, tube, hemispherical, or irregularly shaped. A spheroidal particle refers to a particle wherein the longest central axis (a straight line passing through the particle's geometric center) is no more than about twice the length of other central axes, with the particle being a literally spherical or having an irregular shape. A rod-shaped particle refers to a particle with a longitudinal central axis more than about twice the length of the shortest central axis. Embodiments include making a plurality of collections of particles, with the collections having different rates of degradation in vivo, and mixing collections to make a biomaterial having a degradation performance as desired.

Figure 4:
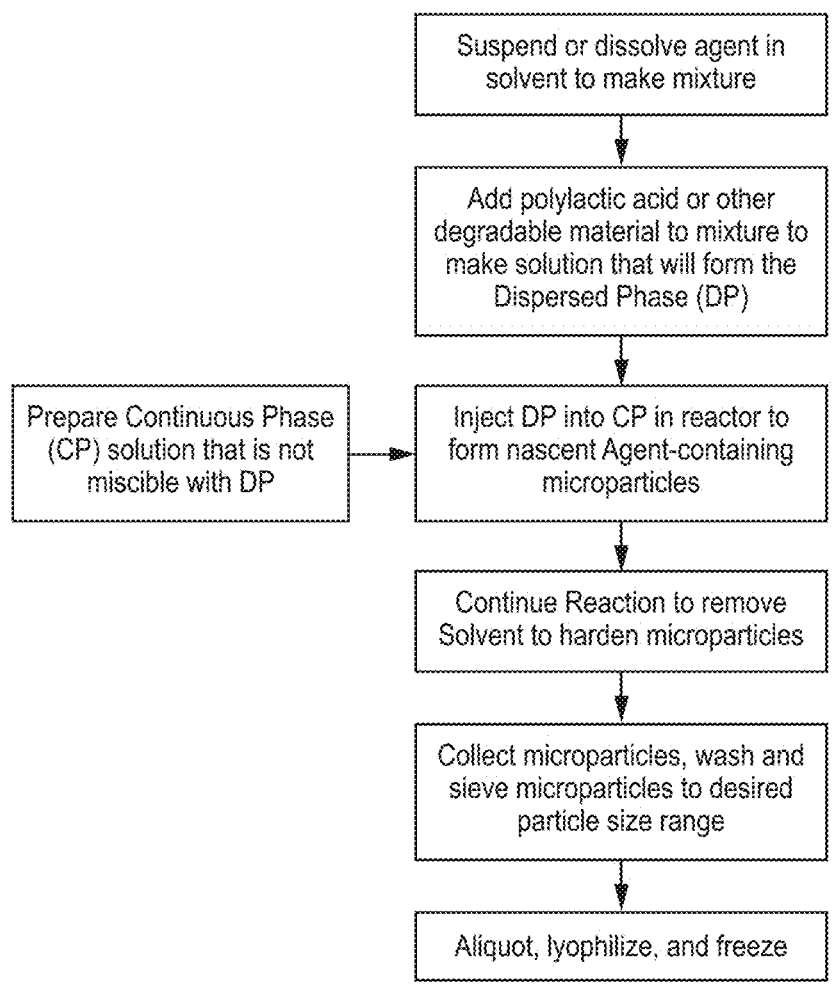
FIG. 4 depicts a process for making microparticles.

FIG. 4 depicts an example of a process of making particles. In this embodiment, an agent is suspended in a solvent to form a mixture. A degradable material is added to the mixture, which is referred to as the dispersed phase. A continuous phase mixture is prepared, and chosen so that the continuous phase is not miscible with the dispersed phase. The two mixtures are mixed and the dispersed phase forms a separate phase that contains the agent. The process may be continued to remove solvent from the dispersed phase. The resultant particles, which are the dispersed phase, are collected and processed as needed, for instance by washing them and selecting desired sizes. The particles may then be used or further processed for use or storage, e.g., by lyophilization and/or freezing.

Degradation of Depots S and Particles

Certain embodiments of composite depots are made with three essential components, 1) a hydrogel matrix, 2) polymer(s) for use in making the drug release matrix, i.e. the microparticles, that contain a therapeutic agent, and (3) the agent itself. An embodiment is a depot comprised of three major components: 1) a biodegradable hydrogel matrix; 2) a biodegradable sustained release polymers (PLGA, PLA, or the like.) and 3) the active drug substance. Each component has a different in vivo persistence which can be formulated for the desired outcome. The terms consisting essentially refers to compositions that have the indicated features and may have other factors present provided that they do not interfere with safety or efficacy; examples of such factors are salts, excipients for a therapeutic agent, and visualization agents.

Degradable materials for microparticles can be chosen to degrade at a rate suitable to deliver a desired dose of drug over a period of time. The bulk hydrogel matrix materials, in turn, can be chosen to persist for a period of time that is shorter, longer or comparable to the time that the drug is delivered. These relations are discussed in the context of the IRR, above, such that the hydrogel matrix and drug release from the microparticles may be synchronized for in vivo persistence to allow a repeat administration at the injection site absent the hydrogel matrix. This embodiment allows ample space for the repeat administration because the hydrogel matrix does not leave behind a solid residue. In contrast, many commercial solid PLGA or PLA implants leave behind a residue, reminiscent of a shell or husk long after the drug is gone. For example, in many instances for sustained release parenteral administrations, the injection location is altered between repeat administrations due to the slower in vivo biodegradation rate of the rod implant or localized microparticles relative to the drug release rate. The index of depot residue retention is a measure of the time that such a shell persists after drug delivery.

An agent may be disposed in degradable particles that provide a release matrix. The particles may be the agent itself, e.g., solid or liquid, or the particles may further comprise a degradable material. Or the agent may be directly in the depot in any form, liquid or solid. Or the agent may be in both a particle and directly dispersed in the xerogel or hydrogel matrix. The agent is released to provide an effective concentration of the agent in an anterior chamber, or other site, during a first period of time. The release is a controlled release that provides the release in the first period of time, which is a predetermined time. The particles and hydrogel matrix materials and other components can be chosen so that the hydrolysis and erosion of the hydrogel is not a rate limiting step of release of the agent. Particles, precursors, depots, degradable materials, agents, and other potential components are discussed in detail elsewhere herein.

Agents

A composite depot comprises a therapeutic agent. The agent may be for a medical use, e.g., to treat a medical condition, to treat a disease, to provide comfort for a patient, pain control, cosmesis, or other purposes. Medical condition is a term that includes a disease. Conventional processes for placing an agent in the prosthesis or coating may be used. Agents may be introduced at the time of making the prosthesis or coating or afterwards. Agents may also be for use in radiation therapies or medical imaging. For instance, radioactive implants, radiotherapy agents, brachytherapy implants, toxins, anticancer agents. And for instance, imaging agents for radiology.

Therapeutic agents include, for example, agents for treating conditions that may result from inflammatory or abnormal vascular conditions, retinal vein occlusion, geographic atrophy, retinitis pigmentosa, retinoblastoma, etc. For cancer, agents may be, e.g., anti-cancer drugs, anti-VEGFs, or drugs known for use in cancer treatment.

Therapeutic agents may be those that are, e.g., anti-VEGF, blocks VEGFR1, blocks VEGFR2, blocks VEGFR3, anti-PDGF, anti-angiogenesis, Sunitinib, E7080, Takeda-6d, Tivozanib, Regorafenib, Sorafenib, Pazopanib, Axitinib, Nintedanib, Cediranib, Vatalanib, Motesanib, macrolides, sirolimus, everolimus, tyrosine kinase inhibitors (TKIs), Imatinib (GLEEVAC) gefinitib (IRESSA), toceranib (PALLADIA), Erlotinib (TARCEVA), Lapatinib (TYKERB) Nilotinib, Bosutinib Neratinib, lapatinib, Vatalanib, dasatinib, erlotinib, gefitinib, imatinib, lapatinib, lestaurtinib, nilotinib, semaxanib, toceranib, vandetanib.

The therapeutic agent may comprise a macromolecule, for example an antibody or antibody fragment. The therapeutic macromolecule may comprise a VEGF inhibitor, for example ranibizumab, the active ingredient in the commercially available Lucentis™. The VEGF (Vascular Endothelial Growth Factor) inhibitor can cause regression of the abnormal blood vessels and improvement of vision when released into the vitreous humor of the eye. Examples of VEGF inhibitors include Lucentis™ (ranibizumab), Eylea™ (VEGF Trap), Avastin™ (bevacizumab), Macugen™ (pegaptanib). Platelet derived growth factor (PDGF) inhibitors may also be delivered, e.g. Fovista™, an anti-PGDF aptamer.

The therapeutic agent may comprise small molecules such as of a steroid or corticosteroid and analogues thereof. For example, the therapeutic corticosteroid may comprise one or more of trimacinalone, trimacinalone acetonide, dexamethasone, dexamethasone acetate, fluocinolone, fluocinolone acetate, loteprednol etabonate, or analogues thereof. Alternatively or in combination, the small molecules of therapeutic agent may comprise a tyrosine kinase inhibitor.

The therapeutic agent may comprise an anti-VEGF therapeutic agent. Anti-VEGF therapies and agents can be used in the treatment of certain cancers and in age-related macular degeneration. Examples of anti-VEGF therapeutic agents suitable for use in accordance with the embodiments described herein include one or more of monoclonal antibodies such as bevacizumab (Avastin™) or antibody derivatives such as ranibizumab (Lucentis™), or small molecules that inhibit the tyrosine kinases stimulated by VEGF such as lapatinib (Tykerb™), sunitinib (Sutent™) sorafenib (Nexavar™), axitinib, or pazopanib.

The therapeutic agent may comprise a therapeutic agent suitable for treatment of dry AMD such as one or more of Sirolimus™ (Rapamycin), Copaxone™ (Glatiramer Acetate), Othera™ Complement C5aR blocker, Ciliary Neurotrophic Factor, Fenretinide or Rheopheresis.

The therapeutic agent may comprise a therapeutic agent suitable for treatment of wet AMD such as one or more of REDD14NP (Quark), Sirolimus™ (Rapamycin), ATG003; EYELEA (VEGF Trap) or complement inhibitor (POT-4).

The therapeutic agent may comprise a kinase inhibitor such as one or more of BIBW 2992 (small molecule targeting EGFR/Erb2), imatinib (small molecule), gefitinib (small molecule), ranibizumab (monoclonal antibody), pegaptanib (small molecule), sorafenib (small molecule), dasatinib (small molecule), sunitinib (small molecule), erlotinib (small molecule), nilotinib (small molecule), lapatinib (small molecule), panitumumab (monoclonal antibody), vandetanib (small molecule) or E7080 (targeting VEGFR2/VEGFR2, small molecule commercially available from Esai, Co.). The therapeutic agent may comprises antibody drugs, e.g. bevacizumab, trastuzumab, cetuximab, and panitumumab.

Therapeutic agents may include various classes of drugs. Drugs include, for instance, steroids, non-steroidal anti-inflammatory drugs (NSAIDS), anti-cancer drugs, antibiotics, an anti-inflammatory (e.g., Diclofenac), a pain reliever (e.g., Bupivacaine), a Calcium channel blocker (e.g., Nifedipine), an Antibiotic (e.g., Ciprofloxacin), a Cell cycle inhibitor (e.g., Simvastatin), a protein (e.g., Insulin). Therapeutic agents include classes of drugs including steroids, NSAIDS, antioxidants, antibiotics, pain relievers, inhibitors of vascular endothelial growth factor (VEGF), chemotherapeutics, anti-viral drugs, for instance. Examples of NSAIDS are Ibuprofen, Meclofenamate sodium, mefanamic acid, salsalate, sulindac, tolmetin sodium, ketoprofen, diflunisal, piroxicam, naproxen, etodolac, flurbiprofen, fenoprofen calcium, Indomethacin, celoxib, ketrolac, and nepafenac. The drugs themselves may be small molecules, proteins, RNA fragments, proteins, glycosaminoglycans, carbohydrates, nucleic acid, inorganic and organic biologically active compounds where specific biologically active agents include but are not limited to: enzymes, antibiotics, antineoplastic agents, local anesthetics, hormones, angiogenic agents, anti-angiogenic agents, growth factors, antibodies, neurotransmitters, psychoactive drugs, anticancer drugs, chemotherapeutic drugs, drugs affecting reproductive organs, genes, and oligonucleotides, or other configurations.

Therapeutic agents may include a protein or other water soluble biologics. These include peptides of various molecular weights. Peptides include therapeutic proteins and peptides, antibodies, antibody fragments, short chain variable fragments (scFv), growth factors, angiogenic factors, and insulin. Other water soluble biologics are carbohydrates, polysaccharides, nucleic acids, antisense nucleic acids, RNA, DNA, small interfering RNA (siRNA), and aptamers.

The therapeutic agents may be used as part of a method of treating the indicated condition or making a composition for treating the indicated condition. For example, AZOPT (a brinzolamide opthalmic suspension) may be used for treatment of elevated intraocular pressure in patients with ocular hypertension or open-angle glaucoma. BETADINE in a Povidone-iodine ophthalmic solution may be used for prepping of the periocular region and irrigation of the ocular surface. BETOPTIC (betaxolol HCl) may be used to lower intraocular pressure, or for chronic open-angle glaucoma and/or ocular hypertension. CILOXAN (Ciprofloxacin HCl opthalmic solution) may be used to treat infections caused by susceptible strains of microorganisms. NATACYN (Natamycin opthalmic suspension) may be used for treatment of fungal blepharitis, conjunctivitis, and keratitis. NEVANAC (Nepanfenac opthalmic suspension) may be used for treatment of pain and inflammation associated with cataract surgery. TRAVATAN (Travoprost ophthalmic solution) may be used for reduction of elevated intraocular pressure-open-angle glaucoma or ocular hypertension. FML FORTE (Fluorometholone ophthalmic suspension) may be used for treatment of corticosteroid-responsive inflammation of the palperbral and bulbar conjunctiva, cornea and anterior segment of the globe. LUMIGAN (Bimatoprost ophthalmic solution) may be used for reduction of elevated intraocular pressure-open-angle glaucoma or ocular hypertension. PRED FORTE (Prednisolone acetate) may be used for treatment of steroid-responsive inflammation of the palpebral and bulbar conjunctiva, cornea and anterior segment of the globe. PROPINE (Dipivefrin hydrochloride) may be used for control of intraocular pressure in chronic open-angle glaucoma. RESTASIS (Cyclosporine ophthalmic emulsion) may be used to increases tear production in patients, e.g., those with ocular inflammation associated with keratoconjunctivitis sicca. ALREX (Loteprednol etabonate ophthalmic suspension) may be used for temporary relief of seasonal allergic conjunctivitis. LOTEMAX (Loteprednol etabonate ophthalmic suspension) may be used for treatment of steroid-responsive inflammation of the palpebral and bulbar conjunctiva, cornea and anterior segment of the globe. MACUGEN (Pegaptanib sodium injection) may be used for Treatment of neovascular (wet) age-related macular degeneration. OPTIVAR (Azelastine hydrochloride) may be used for treatment of itching of the eye associated with allergic conjunctivitis. XALATAN (Latanoprost ophthalmic solution) may be used to reduce elevated intraocular pressure in patients, e.g., with open-angle glaucoma or ocular hypertension. BETIMOL (Timolol opthalmic solution) may be used for treatment of elevated intraocular pressure in patients with ocular hypertension or open-angle glaucoma. Latanoprost is the pro-drug of the free acid form, which is a prostanoid selective FP receptor agonist. Latanoprost reduces intraocular pressure in glaucoma patients with few side effects. Latanoprost has a relatively low solubility in aqueous solutions, but is readily soluble in organic solvents typically employed for fabrication of microspheres using solvent evaporation.

Further embodiments of therapeutic agents for delivery include those that specifically bind a target peptide in vivo to prevent the interaction of the target peptide with its natural receptor or other ligands. AVASTIN, for instance, is an antibody that binds VEGF. An IL-1 trap that makes use of the extracellular domains of IL-1 receptors is also known; the trap blocks IL-1 from binding and activating receptors on the surface of cells. Embodiments of agents for delivery include nucleic acids, e.g., aptamers. Pegaptanib (MACUGEN), for example, is a pegylated anti-VEGF aptamer. An advantage of the particle-and-hydrogel delivery process is that the aptamers are protected from the in vivo environment until they are released. Further embodiments of agents for delivery include macromolecular drugs, a term that refers to drugs that are significantly larger than classical small molecule drugs, i.e., drugs such as oligonucleotides (aptamers, antisense, RNAi), ribozymes, gene therapy nucleic acids, recombinant peptides, and antibodies.

One embodiment comprises extended release of a medication for allergic conjunctivitis. For instance, ketotifen, an antihistamine and mast cell stabilizer, may be provided in particles and released to the eye as described herein in effective amounts to treat allergic conjunctivitis. Seasonal Allergic Conjunctivitis (SAC) and Perennial Allergic Conjunctivitis (PAC) are allergic conjunctival disorders. Symptoms include itching and pink to reddish eyes. These two eye conditions are mediated by mast cells. Non-specific measures to ameliorate symptoms conventionally include: cold compresses, eyewashes with tear substitutes, and avoidance of allergens. Treatment conventionally consists of antihistamine mast cell stabilizers, dual mechanism anti-allergen agents, or topical antihistamines. Corticosteroids might be effective but, because of side effects, are reserved for more severe forms of allergic conjunctivitis such as vernal keratoconjunctivitis (VKC) and atopic keratoconjunctivitis (AKC).

Oxifloxacin is the active ingredient in VIGAMOX, which is a fluoroquinolone approved for use to treat or prevent ophthalmic bacterial infections. VKC and AKC are chronic allergic diseases where eosinophils, conjunctival fibroblasts, epithelial cells, mast cells, and/or TH2 lymphocytes aggravate the biochemistry and histology of the conjunctiva. VKC and AKC can be treated by medications used to combat allergic conjunctivitis. Permeation agents are agents and may also be included in a gel, hydrogel, organogel, xerogel, and biomaterials as described herein. These are agents that assist in permeation of a drug into an intended tissue. Permeation agents may be chosen as needed for the tissue, e.g., permeation agents for skin, permeation agents for an eardrum, permeation agents for an eye.

The agent may be treatment of a back of the eye disease, e.g., wherein the back of the eye disease is age-related macular degeneration (AMD) cystoid macular edema (CME), diabetic macular edema (DME), posterior uveitis, and diabetic retinopathy, or glaucoma.

The agents may be, e.g., an agent comprises anti-VEGF, blocks VEGFR1, blocks VEGFR2, blocks VEGFR3, anti-PDGF, anti-PDGF-R blocks PDGFRβ, an anti-angiogenic agent, Sunitinib, E7080, Takeda-6d, Tivozanib, Regorafenib, Sorafenib, Pazopanib, Axitinib, Nintedanib, Cediranib, Vatalanib, Motesanib, macrolides, sirolimus, everolimus, tyrosine kinase inhibitors (TKIs), Imatinibn gefinitib, toceranib, Erlotinib, Lapatinib, Nilotinib, Bosutinib Neratinib, lapatinib, Vatalanib, comprises low-soluble prostaglandin analogues for glaucoma, nepafenac, macrolides, rapamycin, sirolimus, tacrolimus, or serves to block mTOR receptors for AMD (also known as choroidal neovascularization (CNV). mTOR refers to mammalian target of rapamycin. Agents may be, e.g, moxifloxacin, dexamethasone, travoprost, steroids, fluoroquinolones, prostaglandin analogs, prostamides.

Examples of Depots S and Loading

A composite depot may be made in a size and shape suited to its intended site of use. One embodiment of a depot, suitable for use in an AC or other site, is a crosslinked depot that, as a hydrogel, has a diameter of less than 1 mm at equilibrium water content. The depot length may be, e.g., 0.1-10 mm; Artisans will immediately appreciate that all ranges and values between the explicitly stated bounds are contemplated, with, e.g., any of the following being available as an upper or lower limit: 0.1, 0.5, 1, 2, 3, 4, 5, 6, 7, 8, 9, or 10 mm. The length is the longest dimension and the diameter refers to the second-longest dimension of a depot having a length, a width, and a thickness. In the case of a circular cylinder, a width and thickness would be the same. The term diameter refers to the longer of a width and a thickness. One or more of a length, a width, a thickness or diameter may be, e.g., from 0.1-10 mm or, for larger sites, 5-500 mm; Artisans will immediately appreciate that all ranges and values between the explicitly stated bounds are contemplated, with, e.g., any of the following being available as an upper or lower limit: 0.1, 0.5, 1, 2, 3, 4, 5, 6, 7, 8, 9, 10, 15, 20, 25, 30, 35, 40, 50, 60, 70, 80, 90, 100 mm. As is evident, one or more dimensions of length, width, thickness, and diameter may be less than 1-100 mm; Artisans will immediately appreciate that all ranges and values between the explicitly stated bounds are contemplated, with, e.g., any of the following being available as an upper limit: 1, 1.2, 1.3, 1.4, 1.5, 1.6, 1.8, 1.9, 2, 3, 4, 5, 6, 7, 8, 9, 10, 15, 20, 25, 30, 35, 40, 50, 60, 70, 80, 90, 100 mm.

The depot may comprise particles that comprise an agent or be free of particles that comprise an agent. Particles may be, e.g., microparticles and/or nanoparticles. Microparticles or nanoparticles may have, e.g., a diameter 0.001 to less than 100 microns; Artisans will immediately appreciate that all ranges and values between the explicitly stated bounds are contemplated, with, e.g., any of the following being available as an upper or lower limit: 0.001, 0.01, 0.1, 0.2, 0.5, 1, 1.5, 2, 5, 10, 15, 20, 30, 35, 38, 40, less than 40. These particle sizes may be for some of the particles, or for all of the particles, or for all of the agent-containing particles. Microparticles fall within these ranges and have diameters of 1 to 100 microns, e.g. 1 to 55, 1-20, or 10 to 53 microns diameter.

The xerogel may comprise has an amount of the agent that is from 1 to 75% w/w; Artisans will immediately appreciate that all ranges and values between the explicitly stated bounds are contemplated, with, e.g., any of the following being available as an upper or lower limit: 1, 2, 3, 4, 5, 10, 15, 20, 25, 30, 35, 40, 45, 50, 55, 60, 65, 70, 75. A xerogel may be loaded with a suitable amount of an agent, e.g., an depot that has an amount of the agent that is from 1 to 10,000 micrograms (μg); Artisans will immediately appreciate that all ranges and values between the explicitly stated bounds are contemplated, with, e.g., any of the following being available as an upper or lower limit: 1, 2, 3, 4, 5, 10, 50, 100, 200, 300, 400, 500, 1,000, 2,000, 5,000, 10,000, 50,000, or 100,000 μg.

The xerogel or hydrogel may have a suitable shape, e.g., a particle can have any shape, e.g., spherical, oblate, ellipsoidal, rod, disc, tube, hemispherical, or irregularly shaped. Volumes of depots s may be, e.g., from 0.1 microliter (μl) to 100 milliliter (ml); Artisans will immediately appreciate that all ranges and values between the explicitly stated bounds are contemplated, with, e.g., any of the following being available as an upper or lower limit: 0.1, 0.5 1, 2, 3, 4, 5, 6, 7, 8, 9, or 10 μl or 1, 2, 3, 4, 5, 6, 7, 8, 9, 10, 15, 25, 50, 60, 70, 90, 100 ml.

As is evident, combinations of the features may be mixed and matched, e.g., wherein the hydrogel is rod-shaped and has a diameter of no more than 1 mm or no more than 1.6 mm. Or wherein the hydrogel is disc-shaped, spherical, or hemispherical with a diameter of no more than 1 mm or no more than 1.5 mm or no more than 1.6 mm. Various depot s, agents, materials, and options for placing agents into depots are provided elsewhere herein.

Eye Disease States

The materials described herein may be used to make a depot to deliver drugs or other therapeutic agents (e.g., imaging agents or markers) to eyes or tissues nearby. The depot is preferably a composite depot that comprises a matrix (xerogel or hydrogel) with embedded particles.

Eye diseases include ocular pathologies, with hyphema, ocular hypertension, and glaucoma being conditions for treatment with an anterior chamber depot. Many agents are suitable for ocular delivery, e.g., NSAIDs, steroids, anti-glaucoma drugs, antivirals, antibiotics, mydriatics, and anti-fungals administered via intracameral injections.

Some of the disease states are back-of-the-eye diseases. The term back-of-the eye disease is recognized by artisans in these fields of endeavor and generally refers to any ocular disease of the posterior segment that affects the vasculature and integrity of the retina, macula or choroid leading to visual acuity disturbances, loss of sight or blindness. Disease states of the posterior segment may result from age, trauma, surgical interventions, and hereditary factors. Some back-of-the-eye disease are; age-related macular degeneration (AMD) cystoid macular edema (CME), diabetic macular edema (DME), posterior uveitis, and diabetic retinopathy. Some back-of-the-eye diseases result from unwanted angiogenesis or vascular proliferation, such as macular degeneration or diabetic retinopathy. Drug treatment options for these and other ocular conditions may be provided by delivery of agents from a depot.

After placement in the eye, embodiments include a depot that provides a concentration of the agent that is from 0.05 to 500 ng/mL in an anterior chamber of the eye. A depot for the iridocorneal angle, particularly for open angle glaucoma, could be, e.g., 0.2 to 1.5 mm diameter and 0.5-5 mm in length. In regards to these dimensions, artisans will immediately appreciate that all ranges and values between the explicitly stated bounds are contemplated, with, e.g., any of the following being available as an upper or lower limit: 0.2, 0.3, 0.5, 0.7, 0.9, 1, 1.1, 1.3, 1.5 mm (diameter) or 0.5, 0.6, 0.8, 1, 1.2, 1.5, 2, 2.5, 3, 3.5, 4, 4.5, 5 mm (length).

Kits

Kits or systems may be prepared. The kits may include materials as needed for medical personnel to use the depots. The kits are manufactured using medically acceptable conditions and contain depots that have sterility, purity and preparation that is pharmaceutically acceptable. The kit may contain an applicator as appropriate, as well as instructions. In some embodiments, the kit has at least one depot and an applicator. Kits may include, for instance, items such as a depot, aqueous medium for hydration of the depot, an applicator, a needle, an applicator or needle pre-loaded with a depot, a light or other machine for visualization of the depot, surgical tools, cutting devices, topical drugs, or topical pain relievers.

Administration

The materials described herein may be used to deliver agents. One mode of application is to pass a depot through a needle, microneedle, cannula, catheter, or hollow wire to a site. Some sites require a careful administration process, e.g., in an eye. Fine needles may be used and/or needles with a limited length. The work may be performed, if helpful, under magnification, with a stereoscope, with guided imaging, or with robots (for instance as described by Eindhoven University of Technology). Depots may be made with sizes and lubricity for manual injection through a small gauge needle, e.g., a 27 gauge needle or smaller needle, e.g., 30 gauge needle.

One or more depot (e.g., 1-10, 1, 2, 3, 4, 5 6, 7, 8, 9, 10) may be placed in an anterior chamber of an eye or at other sites. Sites for a depot include an eye, the vitreous, episcleral, in the posterior subtenon's space (Inferior fornix), subconjunctival, sub-tenon, retinal, subretinal, intracanalicular, intracameral, intravitreal, intrascleral, choroidal, suprachoroidal, a retina, subretinal, or a lens, a surface of the cornea or the conjunctiva, among others. Accordingly, embodiments include providing an effective amount or a calculated effective amount of an agent at such a site, e.g., the effective amount at an eye, the anterior chamber, the vitreous, episcleral, in the posterior subtenon's space (Inferior fornix), subconjunctival, sub-tenon, retinal, subretinal, intracanalicular, intracameral, intravitreal, intrascleral, choroidal, suprachoroidal, a retina, subretinal, or a lens, a surface of the cornea or the conjunctiva.

Sites for a depot further include a tissue, lumen, void, potential space, inside an animal (human or otherwise), or on a surface of an animal. The term tissue is broad. Sites include iatrogenic sites, sites where tissue is removed, and surgical sites. Sites include cancer tissue, at or near cancer tissue, dental tissue, gums, periodontal, sinus, brain, intravascular, aneurysm, and site of a pathology. Sites for a depot include openings in a tissue. Embodiments include depots passed into or through or across a natural or artificial lumen, e.g., a sphincter, duct, ostium, sinus or other lumen. Artificial lumens are made for medical purposes, e.g., to deliver a drug, for surgery, or other medical or cosmetic purposes. The depot is sized appropriately.

EXAMPLES

Example 1. Formation of Test Articles for Animal Testing

Travoprost was used as a model therapeutic agent for delivery and also as a test of efficacy. Test articles 1 and 2 were made with the formulations indicated in Table 1. Referring to FIGS. 4 and 5, microparticles were made by dissolving travoprost in dichloromethane (DCM) and then poly DL-lactide (either 100 DL 4A, 100 DL 7A, 100 DL 9A, or 100 DL 4.5E) in the DCM/travoprost solution to specified concentrations. A or E refers to either acid or ester end groups in the PLA. The 4, 7, 9 and 4.5 refer to the inherent viscosity at a defined concentration (usually 0.1 or 0.5%) in chloroform at a defined temperature (usually 25 or 30° C.). Method difference in inherent viscosity is supplier dependent. This inherent viscosity is directly related to the median molecular weight of the lactide polymer (however it is understood that all polymers are a range). A lower number is a shorter MW and higher number is a higher MW (4 is approximately 50 kD, 4.5 is approximately 60 kD, 7 is approximately 100 kD and 9 is approximately 135 kD). A solution of 1% polyvinyl alcohol in water for injection (WFI) was placed into a jacketed baffled reactor with stirring (the continuous phase). The DL-lactide containing mixture was injected into the reactor where it formed a separate dispersed phase. The reaction proceeded overnight with stirring, while the particles hardened due to extraction and evaporation of the DCM. The particles were removed from the reactor, washed with water and sieved into collections of particles based on size. The collections were aliquoted into vials and lyophilized. The particles were stored frozen until use. Trilysine acetate was reacted with NHS-fluorescein at basic pH at a predetermined ratio to form a fluorescein-trilysine conjugate. An aqueous solution of 8a15K PEG SAP was prepared in water. Particle collections of travoprost encapsulated in 4A, 7A, 9A and 4.5E dried microparticles (approximately 2:2:1:5 parts w/w) were added to an aqueous solution of phosphate-buffered fluorescein conjugated trilysine and mixed with the solution of 8a15K PEG SAP, and injected into small bore silicone tubing. The tubing was capped and the hydrogel precursors containing suspended microparticles were allowed to react. The tubing was stretched until taut and then dried at low temperature in an oven and underwent contraction during drying. The hydrogel was removed from the tubing and cut into sections. The concentrations and of the various components were chosen to provide either the composition of Test Article 1 (40 µg dose travoprost, 0.25±0.02 mm diameter×3.01±0.03 mm length) or Test Article 2 (26 µg dose travoprost, 0.21±0.01 mm diameter×3.02±0.02 mm length). Contents and a comparison of the formulation composition of the test articles is provided in Table 1.

TABLE 1

Product Composition of Test Articles Used in the Study

|  | Test Article 1 | | Test Article 2 | |
| --- | --- | --- | --- | --- |
| Ingredients | As Formulated (% dry basis) | Theoretical Composition (µg, dry basis) | As Formulated (% dry basis) | Theoretical Composition (µg, dry basis) |
| Travoprost | 25.5% | 40 | 25.5% | 26 |
| 8a15K PEG SAP | 34.6% | 54 | 34.6% | 36 |
| Poly (DL-lactide) 4A | 6.8% | 11 | 6.8% | 7 |
| Poly (DL-lactide) 7A | 6.8% | 11 | 6.8% | 7 |
| Poly (DL-lactide) 9A | 3.4% | 5 | 3.4% | 3 |
| Poly (DL-lactide) 4.5E | 16.9% | 27 | 16.9% | 17 |
| Sodium Phosphate | 3.3% | 5 | 3.3% | 3 |
| NHS-Fluorescein | 2.4% | 4 | 2.4% | 2 |
| Trilysine Acetate | 0.4% | 0.6 | 0.4% | 0.4 |
| Average Weight | N/A | 157 µg | N/A | 103 µg |

Example 2: Formation of Articles for In Vitro Testing

Articles for in vitro testing were made according to the process of Example 1. The in vitro release testing was performed under sink conditions using simulated physiological conditions (PBS, pH 7.4 at 37° C.) with the exception of the addition of 0.5% polyoxyl 40 hydrogenated castor oil to the dissolution media to increase travoprost solubility. This surfactant is used as a solubility enhancement agent in TRAVATAN eye drops. FIG. 7 shows the in vitro release from the microparticles (individual components and/or blended to provide a 40 µg dose) in the hydrogel matrix under simulated physiological conditions (phosphate buffered saline, pH 7.4 @ 37° C. with the addition of surfactant to aid drug solubility in the dissolution media to assure sink conditions) made, above, as per Table 1. In brief, the collections were placed in an excess of this dissolution media and sampled at defined time points and analyzed for travoprost content by reverse-phase ultra performance liquid chromatographic with ultraviolet light detection. Sample concentrations from peak areas were calculated relative to a standard curve.

Example 3: Animal Testing with Depots of Example 1

Assignment: Three female non-pregnant and nulliparous beagles, at least 6 months of age, were assigned to this study (Toxikon, Inc.) under IACUC protocol for use in ophthalmology studies. The animal assignment is provided in Table 2. The animals were identified by ear tattoo numbers as 2277, 4563 and 1896.

TABLE 2

Animal Assignment

| Animal # | Eye | Test Article | Travoprost Dose |
| --- | --- | --- | --- |
| 2277 | OS | 2 | 26 µg |
| 2277 | OD | 2 | 26 µg |
| 1896 | OS | 1 | 40 µg |
| 1896 | OD | 2 | 26 µg |
| 4563 | OS | 1 | 40 µg |
| 4563 | OD | 2 | 26 µg |

Dose Administration: The dogs were anesthetized prior to the injection procedure. Initially the dogs were sedated with dexmedetomidine and then placed on isoflurane via inhalation. Both eyes were given 1-2 drops of proparacaine hydrochloride topically prior to the procedure. The fur surrounding the eye was wiped with a povidone-iodine solution (Betadine®). The appropriate test article, see Table 2, was injected into the anterior chamber while being viewed under an operating microscope using a 27G needle affixed to a Hamilton syringe with stainless plunger to deploy the depot. A representative injection procedure is seen in FIGS. 8A-8D.

Once the injection was complete, the eye was treated with a bead of prophylactic antibiotic ointment (erythromycin ophthalmic). The dog was taken off isoflurane and oxygen gas (O2) and an equal volume of atipamezole was administered intramuscularly (IM) to reverse the effects of the sedative.

Post-Dose Assessment Plan: Animals were evaluated at the specified times following the injection procedure per the assessments listed in Table 3.

TABLE 3

Ocular Assessments Were Performed at Specified Times Post Depot Injection

| Assessment | Days |
| --- | --- |
| Eye health | 3, 7, 14, 28, 42, 56, 70, 84, 98, 112, 126, 140 |
| Sclera photographs | |
| [1]Depot location | |
| Pupil constriction (qualitative) | 3, 7, 14, 42 |
| Pupil constriction (quantitative) | 28, 56, 70, 84, 98, 112, 126, 140 |
| Ophthalmic exam | 28, 56, 84, 112, 140 |
| Tonometry (IOP) | |
| Pachymetry | |
| [2]Aqueous humor tap | |
| Depot photographs | |

[1]Record general location as hands on a clock with bottom of eye as 6:00 pm
[2]Performed with 30G insulin needle and 0.1 mL collection in microfuge tube (freeze)

Eye Health: Eyes were evaluated as healthy or normal, and any visual abnormalities were recorded.

Sclera Photographs: Photographs of the sclera were taken to qualitatively compare hyperemia over time between images.

Depot Location: The depot location was visualized using a blue light and yellow filtered goggles or a slit lamp affixed with a yellow filter to observe the location of the depot within the AC. Recordings were made using clock time to approximate visual location.

Pupil Constriction (Qualitative and Quantitative): The constriction of the pupil was either visually qualitatively assessed or quantitatively measured using a ruler. Values less than 1 mm were recorded as <1 mm.

Ophthalmic Examinations: In anesthetized animals, both eyes of each dog were examined for macroscopic findings and were scored according to the Combined Draize and McDonald-Shadduck Scoring Systems. (Wilhelmus, Kirk R. "The Draize eye test." Survey of ophthalmology 45.6 (2001): 493-515.; McDonald, T. O., and J. A. Shadduck. "Eye irritation. Advances in Modern Toxicology, IV: Dermatotoxicology and Pharmacology." (1977)). The examinations included slit lamp biomicroscopy and fluorescein staining. Specifically, the slit lamp examination looked for alterations in the cornea, conjunctiva, iris, anterior chamber, and lens. The corneal surface also was assessed using fluorescein stain. The exam included an assessment of whether any corneal edema proximate to the depot was observed. Tables used for scoring the studies are provided below.

Tonometry: In anesthetized animals, tonometry to measure intraocular pressure (IOP) was performed using a TONOVET TONOMETER (TioLAT, Helsinki, Finland).

Pachymetry: In anesthetized animals, pachymetry was performed to measure corneal thickness using an iPac® hand-held pachymeter (Reichert, Inc., Depew, NY).

Depot Photographs: In anesthetized animals, photography of the depots was performed both through an operating microscope and using a camera affixed with a yellow filter while illuminating the depot with a blue light source.

Aqueous Humor (AH) Taps: The AH was tapped using a 30G insulin needle to collect approximately 0.1 mL of AH. The material was transferred into a microfuge tube and the sample was immediately stored frozen on dry ice. Samples were shipped frozen on dry ice to Molecular MS Diagnostics (Warwick, RI) for travoprost and travoprost free acid concentration determination using an on-line solid phase extraction with HPLC-MS/MS having a validated limit of quantitation of 50 pg/mL.

Example 4: Results for Animals of Example 3

Eye Health: Eye health for all animals was recorded as normal or healthy through over the study duration Sclera Photographs: Photographs of the sclera over the study duration qualitatively indicating hyperemia are shown in the FIG. 10A-10F. Images indicate dilation of the outflow blood vessels post administration with OTX-TI and a general reduction of this hyperemia/scleral redness over time. It is known that travoprost (0.004%) administered once a day to normal healthy beagles for 5 treatment days demonstrated hyperemia for the entire treatment period (Carvalho et al., 2006). Dilation of the outflow vessels with a similar sustained release F2α prostaglandin (bimatoprost) administered by intracameral injection to beagles was observed in the sclera and reported to be bimatoprost dose dependent (Hughes et al., 2010).

Depot Location: The depot location, shown in Table 4, was generally visualized and recorded to be near the bottom of eye in the iridocorneal angle. Two of four depots were not visible at Day 70 and all six weren't visible at Day 84. This indicates that the fluoresceinated hydrogel component of this formulation (7.5% 8a20KSAP) has an approximate in vivo duration in beagle AH of approximately 2.5 to 3 months.

TABLE 4

OTX-TI Depot Location During Over the Study Duration

| Day | Animal/Eye | | | | | |
|---|---|---|---|---|---|---|
| | 2277 OS | 2277 OD | 1896 OS | 1896 OD | 4563 OS | 4563 OD |
| 3 | 5:00 | 6:30 | 7:30 | 6:00 | 6:00 | 5:30 |
| 7 | 7:00 | 6:00 | 6:00 | 5:30 | 8:30 | 7:00 |
| 14 | 7:00 | 7:00 | 6:00 | 7:00 | 6:30 | 5:30 |
| 28 | N/A[1] | 6:00 | 6:00 | 6:00 | 6:00 | 6:00 |
| 42 | 6:00 | 7:00 | 6:00 | 6:00 | 6:00 | 6:00 |
| 56 | 8:00 | 5:00 | 6:00 | 7:00 | 5:00 | 6:30 |
| 70 | 6:30 | 5:30 | not visible | 6:00 | 6:00 | not visible |
| 84 | not visible | not visible | not visible | not visible | not visible | not visible |
| 98 | N/A | N/A | N/A | N/A | N/A | N/A |
| 112 | N/A | N/A | N/A | N/A | N/A | N/A |
| 126 | N/A | N/A | N/A | N/A | N/A | N/A |
| 140 | N/A | N/A | N/A | N/A | N/A | N/A |

[1]Animal coming out of anesthesia during depot location check—location is unconfirmed Depot Photographs: Representative images of OTX-TI in the AC taken at Day 28 and photographed under natural and fluorescence lighting conditions are shown in FIGS. 11A-11D. Representative images of OTX-TI in the AC taken at Day 56 and photographed under fluorescence lighting conditions are shown in FIG. 12. Results show the depot fully intact and generally residing in the lower portion of the AC in the iridocorneal angle as denoted in Table 4.

Pupil Constriction (Qualitative and Quantitative): The pupil was constricted (<2 mm) in all animals through 112 days. At days 126 and 140 the pupil demonstrated no constriction, as shown in Table 5. Results are in good agreement with those reported in the literature for glaucomatous beagles demonstrating pupil constriction (miosis) when administered once daily 0.004% travoprost drops (Gelatt and MacKay, 2004). The pupil constriction results demonstrate a pharmacodynamic response to travoprost delivered by OTX-TI in the beagle model through 112 days.

In this example the index of depot residue retention based on hydrogel visualization was 84/112=0.75. In this case it is apparent, based on the elongated pupil constriction time, the microparticles persisted about 33% longer than the hydrogel shell. An alternative implication is that the pupil constriction effect persisted after the drug release was completed.

TABLE 5

Pupil Constriction and Pupil Diameter Over the Study Duration by Animal Identification and Eye

| Day | Animal/Eye | | | | | |
|---|---|---|---|---|---|---|
| | 2277 OS | 2277 OD | 1896 OS | 1896 OD | 4563 OS | 4563 OD |
| 3 | complete | complete | complete | complete | complete | complete |
| 7 | complete | complete | complete | complete | complete | complete |
| 14 | complete | complete | complete | complete | complete | complete |
| 28 | <1 mm | <1 mm | <1 mm | <1 mm | <1 mm | <1 mm |
| 42 | complete | complete | complete | complete | complete | complete |
| 56 | 1 mm | 1 mm | 1 mm | 1 mm | 1 mm | 1 mm |
| 70 | 1.5 mm | 1 mm | 1 mm | 1 mm | 1.5 mm | 1.5 mm |
| 84 | 1 mm | 1 mm | 1 mm | 1 mm | 1 mm | 1 mm |
| 98 | 1-2 mm | 1-2 mm | 1 mm | 1 mm | 2 mm | 2 mm |
| 112 | 1 mm | 1 mm | 1 mm | 1 mm | 1 mm | 1 mm |
| 126 | 4 mm | 5 mm | 6 mm | 5 mm | 4 mm | 6 mm |
| 140 | 6-7 mm | 6-7 mm | 7 mm | 7 mm | 7 mm | 7 mm |

Tonometry: IOP measurements recorded over the study duration are shown in Table 6. The 11 mmHg average value recorded at day 28 is in good agreement with the IOP recorded for glaucomatous beagles when administered a recurring once daily dose of 0.0033% travoprost drops (MacKay et al., 2011) or in normal dogs when administered a recurring once daily dose of 0.004% travoprost (Carvalho et al., 2006). Two of three dogs (2277 and 1896) demonstrated an average TOP of 12 mmHg at day 56. Studies of normotensive untreated beagles (n=32 eyes) measured using a TonoVet reported an average IOP of 18.1 mmHg (Driscoll and Blizzard, 2016). The IOP reduction from 18 to either 11 or 12 mmHg demonstrates a pharmacodynamic response to travoprost delivered by OTX-TI in the beagle model. No apparent difference in average IOP is noted at day 84 and beyond. It is important to note that this lack of IOP response may simply be due to the degradation of the hydrogel portion of the depot which may have influenced drug concentrations in the AH necessary for sufficient IOP reduction.

TABLE 6

Intraocular Pressure Results Over the Study Duration by Animal Identification and Eye*

| Day | Animal/Eye | | | | | | Average | Std Dev |
|---|---|---|---|---|---|---|---|---|
| | 2277 OS | 2277 OD | 1896 OS | 1896 OD | 4563 OS | 4563 OD | | |
| 28 | 11 | 12 | 9 | 9 | 13 | 12 | 11 | 2 |
| 56 | 12 | 12 | 10 | 14 | 19 | 16 | 14 | 3 |
| 84 | 16 | 14 | 17 | 14 | 15 | 14 | 15 | 1 |
| 112 | 15 | 15 | 15 | 17 | 14 | 15 | 15 | 1 |
| 140 | 16 | 18 | 13 | 15 | 15 | 11 | 15 | 2 |

*All results in table in mmHg

Figure 13:
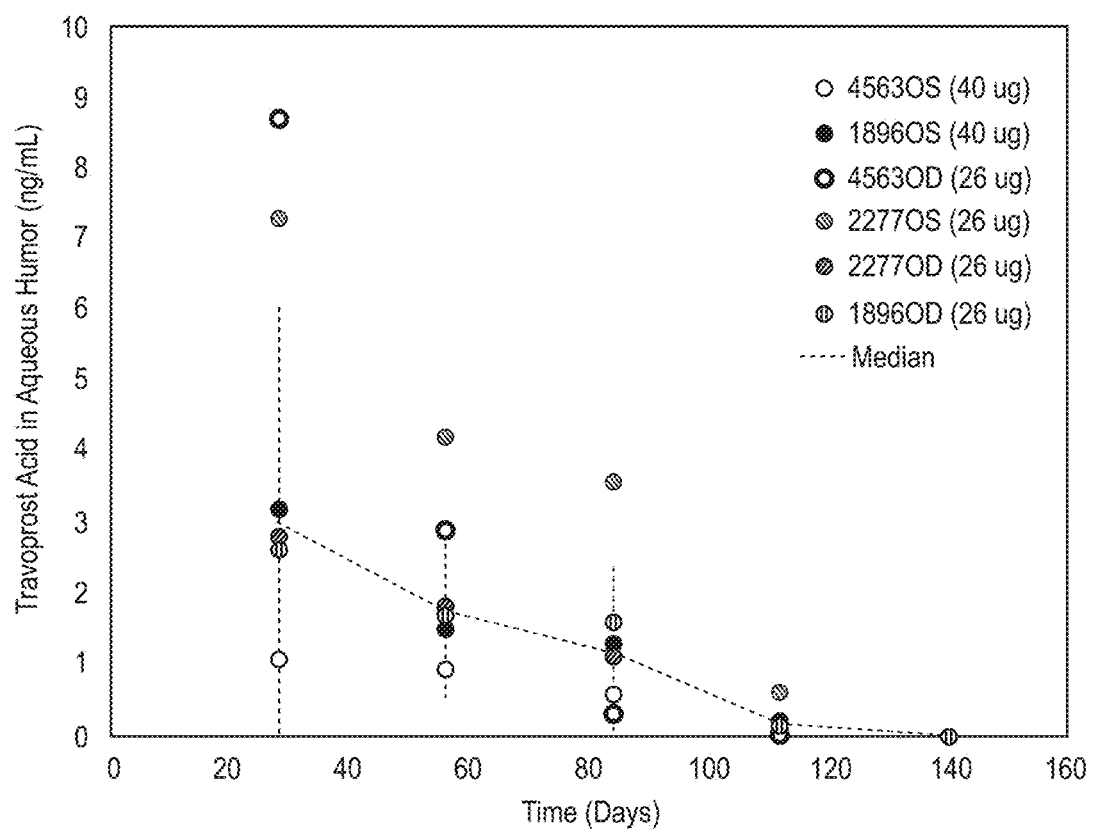
FIG. 13 is a plot of data showing drug levels in the aqueous humor from release of an agent from a composite depot into an anterior chamber.

Drug Concentration in the AH: Travoprost and Travoprost Free Acid levels in the AH sampled over the study duration at 28 day intervals were determined and summary results are listed in Table 7 and plotted in FIG. 13. Travoprost free acid in the AH is the principal drug form. The absence or minute quantities of the travoprost ester is consistent with literature showing the conversion of the ester to the acid form from similarly dosed travoprost intracameral depots in beagles (Trevino et al., 2014). The level of 4.3 ng/mL at day 28 and 2.2 ng/mL at day 56 in the AC is similar to the travoprost free acid $C_{max}$ observed from eye drop studies in humans which approximate 2 ng/mL (Faulkner et al., 2010) and 3 ng/mL (Martinez-de-la-Casa et al., 2012). The level then decreases to 1.4 ng/mL at 84 days and continues to decrease to 0 ng/mL by the study completion (day 140). As previously mentioned the results obtained at days 84 and beyond are difficult to correlate with IOP reduction since the hydrogel portion of the depot had degraded and was visually absent over that period.

TABLE 7

Travoprost and Travoprost Acid Concentrations in the Aqueous Humor Over the Study Duration by Animal Identification and Eye*

| Day | Form | Animal/Eye | | | | | | Avg. | Std Dev |
|---|---|---|---|---|---|---|---|---|---|
| | | 2277 OS | 2277 OD | 1896 OS | 1896 OD | 4563 OS | 4563 OD | | |
| 28 | Trav Acid | 7.3 | 2.8 | 3.2 | 2.6 | 1.1 | 8.7 | 4.3 | 3.0 |
| | Trav | <LOQ | <LOQ | <LOQ | <LOQ | <LOQ | <LOQ | <LOQ | N/A |
| 56 | Trav Acid | 4.2 | 1.8 | 1.5 | 1.7 | 1.0 | 2.9 | 2.2 | 1.2 |
| | Trav | <LOQ | <LOQ | <LOQ | <LOQ | <LOQ | <LOQ | <LOQ | N/A |
| 84 | Trav Acid | 3.6 | 1.1 | 1.3 | 1.6 | 0.6 | 0.3 | 1.4 | 1.2 |
| | Trav | <LOQ | <LOQ | <LOQ | <LOQ | <LOQ | <LOQ | <LOQ | N/A |

TABLE 7-continued

Travoprost and Travoprost Acid Concentrations in the Aqueous Humor Over the Study Duration by Animal Identification and Eye*

| | | Animal/Eye | | | | | | | |
|---|---|---|---|---|---|---|---|---|---|
| Day | Form | 2277 OS | 2277 OD | 1896 OS | 1896 OD | 4563 OS | 4563 OD | Avg. | Std Dev |
| 112 | Trav Acid | 0.6 | 0.1 | 0.5 | 0.1 | 0.2 | <LOQ | 0.3 | 0.2 |
| | Trav | <LOQ | <LOQ | 0.1 | <LOQ | <LOQ | 0.3 | 0.2 | 0.1 |
| 140 | Trav Acid | <LOQ | <LOQ | <LOQ | <LOQ | <LOQ | <LOQ | N/A | N/A |
| | Trav | <LOQ | <LOQ | <LOQ | <LOQ | <LOQ | <LOQ | N/A | N/A |

*All results in table in ng/mL
LOQ is 50 pg/mL

Ophthalmic Examinations: Anterior segment slit lamp examination scores over the study duration were normal with the following exceptions. The conjunctiva of 4563 OS and OD had a score of 1 for redness/congestion. A small area of opacity (score of 1) was observed at the 11 o'clock position on the cornea of 2277 OS. The cause of the opacity is unknown and the opacity location is distant from the expected injection location. The opacity cleared at subsequent time point. None or sluggish pupillary light reflex was observed bilaterally in all animals through day 112. This effect on pupil constriction and pupillary light reflex is considered to be directly related to the travoprost within the test articles. Travoprost is a potent miotic agent in beagle dogs (Hellberg et al., 2001; Gelatt and MacKay, 2004) and pupil constriction is a direct result of travoprost drug exposure within the eye. The miotic effect from travoprost is absent in humans. Because of the complete pupil constriction an evaluation of the lens with the slit lamp was not possible. A normal pupillary light reflex was observed at days 126 and 140.

Example 5: Formation of Additional Travoprost Intracameral Sustained Release Test Articles and Results in Animal Testing Test articles prepared similarly to Examples 1 and 2, but containing a modified formulation per Table 8 and containing a lower travoprost dose of 18 μg per depot were prepared. The dried dimension of the depot was 0.2 mm×2.0 mm and the hydrated dimension was 0.6 mm×2.3 mm. They were administered as dry depots via intracameral injection into beagles in two studies, Study A: 6 eyes/3 beagles; Study B: 24 eyes/12 beagles.

TABLE 8

Product Composition of Test and Control Articles Used in the Toxicity Study (dry basis to nearest μg)

| | Test Article Lot 03241603 | |
|---|---|---|
| Ingredients | As Formulated (% dry basis) | Theoretical Composition (μg, dry basis) |
| Travoprost | 18.5% | 21.9 |
| 8-arm 15K PEG SAP | 50.9% | 60.5 |
| Poly (DL-lactide) 4A[1] | 4.8% | 5.7 |
| Poly (DL-lactide) 7A[1] | 4.8% | 5.7 |
| Poly (DL-lactide) 9A[1] | 2.4% | 2.9 |
| Poly (DL-lactide) 5.5 E[1] | 12.0% | 14.3 |
| Sodium Phosphate Dibasic | 1.8% | 2.1 |
| Sodium Phosphate Monobasic | 1.0% | 1.2 |
| NHS-Fluorescein | 0.3% | 0.4 |
| Trilysine Acetate | 3.5% | 4.2 |
| Average Depot Weight* | N/A | 119 μg |

[1]The numerical value designates the target inherent viscosity (IV) of the polymer in chloroform.

Study A demonstrates an IOP reduction of 6.2 mmHg in 6 eyes through 2 months as seen in Table 9 below and then an increase in IOP at month 3 and a return to baseline by month 4. They hydrogel portion of the depot is visually present in the angle in all animals at 3 months and absent in 5 of 6 eyes by 4 months.

TABLE 9

| | IOP | Week or Month Number Relative to Start Date | | | | | | |
|---|---|---|---|---|---|---|---|---|
| Group #/Injection | (mmHg) | Pre-Dose | Week 1 | Month 1 | Month 2 | Month 3 | Month 4 | Month 5 |
| Group 1/ | Mean | 17.7 | 8.5 | 11.8 | 11.5 | 16.3 | 18.3 | 17.8 |
| Intracameral | STDEV | 3.4 | 1.5 | 1.6 | 1.8 | 1.0 | 2.7 | 2.1 |
| Injection | N | 6 | 6 | 6 | 6 | 6 | 6 | 6 |

STDEV = Standard Deviation
N = Number of Animals

Study B demonstrates an average IOP reduction of 8, 6 and 7 mmHg in 24 eyes through 1, 2, and 3 months, respectively, as seen in Table 10 below. Pupil constriction is evident in all eyes and demonstrates a reduction in average diameter through 4 months, as seen in Table 11, indicating pharmacodynamic activity of the released travoprost.

TABLE 10

| | | Month Number Relative to Start Date | | | | | | | | |
|---|---|---|---|---|---|---|---|---|---|---|
| | | Pre-Dose | | Month 1 | | Month 2 | | Month 3 | | Month 4 |
| Group # | Animal # | R | L | R | L | R | L | R | L | R | L |
| Group 1 | 1101 | 21 | 16 | 7 | 8 | 11 | 11 | 12 | 11 | 19 | 17 |
| | 1102 | 26 | 21 | 7 | 11 | 13 | 14 | 12 | 13 | 16 | 17 |
| | 1103 | 17 | 17 | 10 | 13 | 13 | 11 | 11 | 12 | 11 | 12 |
| Group 2 | 2101 | 19 | 12 | 10 | 11 | 12 | 13 | 14 | 13 | 13 | 13 |
| | 2102 | 21 | 17 | 11 | 11 | 14 | 16 | 12 | 12 | 15 | 14 |
| | 2103 | 22 | 20 | 12 | 14 | 13 | 11 | 12 | 11 | 15 | 14 |
| Group 3 | 3101 | 19 | 21 | 11 | 10 | 13 | 16 | 13 | 12 | 15 | 15 |
| | 3102 | 21 | 19 | 10 | 13 | 12 | 14 | 11 | 11 | 17 | 17 |
| | 3003 | 16 | 17 | 10 | 10 | 11 | 10 | 12 | 13 | 13 | 15 |
| Group 4 | 4101 | 21 | 18 | 11 | 11 | 12 | 10 | 11 | 10 | 14 | 12 |
| | 4102 | 21 | 18 | 12 | 14 | 12 | 17 | 12 | 15 | 13 | 13 |
| | 4004 | 21 | 19 | 12 | 9 | 14 | 11 | 14 | 12 | 17 | 14 |
| Mean | | 19 | | 11 | | 13 | | 12 | | 15 | |
| STDEV | | 3 | | 2 | | 2 | | 1 | | 2 | |

R = Right Eye
L = Left Eye
STDEV = Standard Deviation

TABLE 11

| | | Month Number Relative to Start Date | | | | | | | | |
|---|---|---|---|---|---|---|---|---|---|---|
| | | Pre-Dose | | Month 1 | | Month 2 | | Month 3 | | Month 4 |
| Group # | Animal # | R | L | R | L | R | L | R | L | R | L |
| Group 1 | 1101 | 8 | 8 | 1 | 1 | 1 | 1 | 1 | 1 | 3 | 2 |
| | 1102 | 7 | 7 | 3 | 2 | <1 | 1 | 1 | 1 | 2 | 2 |
| | 1103 | 8 | 8 | 3 | 2 | 6 | 5 | 4 | 5 | 4 | 3 |
| Group 2 | 2101 | 7 | 7 | 1 | 1 | <1 | 1 | 1 | 1 | 1 | 1 |
| | 2102 | 9 | 9 | 2 | 2 | 3 | 4 | 2 | 3 | 4 | 4 |
| | 2103 | 9 | 8 | 1 | 1 | 3 | 2 | 2 | 2 | 2 | 2 |
| Group 3 | 3101 | 7 | 8 | 3 | 2 | 3 | 4 | 3 | 3 | 2 | 2 |
| | 3102 | 8 | 7 | 5 | 3 | 5 | 3 | 4 | 3 | 1.5 | 1.5 |
| | 3003 | 9 | 9 | 4 | 3 | 3 | 3 | 3 | 3 | 1 | 1 |
| Group 4 | 4101 | 8 | 8 | 3 | 3 | 3 | 3 | 3 | 3 | 1 | 1.5 |
| | 4102 | 9 | 8 | 4 | <1 | 3 | 2 | 3 | 2 | 1 | 2 |
| | 4004 | 8 | 8 | 3 | 2 | 4 | 2 | 3 | 3 | 4 | 2 |
| Mean | | 8 | | 2 | | 3 | | 3 | | 2 | |
| STDEV | | 1 | | 1 | | 1 | | 1 | | 1 | |

R = Right Eye
L = Left Eye
STDEV = Standard Deviation

Figure 14:
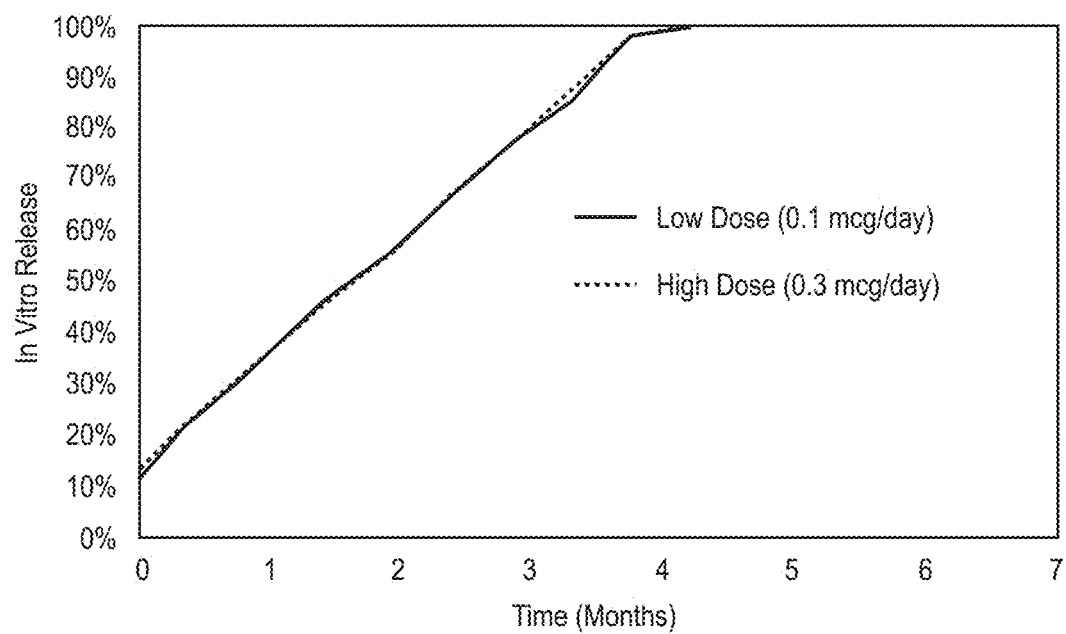
FIG. 14 is a plot of data from Example 6 showing in vitro release from low and high travoprost dose composite depots utilizing a dissolution media of 1×PBS, 0.5% polyoxyl 40 hydrogenated castor oil, 0.01% sodium fluoride, pH 7.2-7.4 performed at 37° C.
Figures 15A, 15B, 15C:
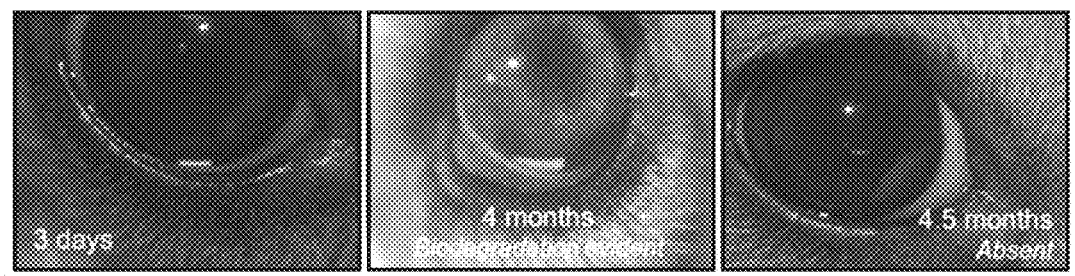
FIGS. 15A-15C are images from Example 6 showing a depot in the same beagle eye at 3 days (15A) and 4 months (15B) post placement and the absence of the depot at 4.5 months (15C); and, FIG. 16 is a plot of in vitro release of travoprost from hydrogel inserts at 37° C. in 1×PBS with 0.5% Castor Oil and 0.01% NaF, pH 7.3 under static (no agitation) and continuous (agitation) conditions.

Example 6: Formation of Additional Travoprost Intracameral Sustained Release Test Articles and Results in Animal Testing Test articles prepared similarly to Example 5, but containing modified travoprost doses of 14 (low) and 41 (high) μg per depot were prepared by controlling the amount of the microparticles present. The dried dimension of the depot was 0.2 mm×2.0 mm for the low dose and 0.3 mm×2.0 mm for the high dose. The hydrated dimension was 0.5 mm×2.3 mm for the low dose and 0.5 mm×2.3 mm for the high dose. They were administered as dry depots via intracameral injection into beagles: 24 eyes/12 beagles. The study demonstrates an average IOP reduction for the low dose of 6, 5, 6 and 6 mmHg and high dose of 6, 8, 7 and 9 mmHg in 12 eyes each through 1, 2, 3 and 4 months, respectively, as seen in the Table 12 below. Concomitant pupil constriction is evident in all eyes and demonstrates a reduction in average diameter through 4 months for both doses indicating pharmacodynamic activity of the released travoprost and then an approximate return to baseline in pupil diameter by 6 months. The 4 month duration of pharmacodynamic activity coincides with the 4 months of travoprost release demonstrated in the in vitro testing, as seen in FIG. 14, utilizing a dissolution media of 1×PBS, 0.5% polyoxyl 40 hydrogenated castor oil, 0.01% sodium fluoride, pH 7.2-7.4 performed at 37° C. The approximate travoprost release amount per day for the low dose formulation is 0.1 μg/day and for the high dose formulation is 0.3 μg/day. The duration of the pharmacodynamic responses of IOP reduction and pupil constriction correlates with the duration of in vitro release for the both the low dose and high dose formulations. FIGS. 15A-15C is a photomontage of depots from Example 6 showing a depot in the same beagle eye at 3 days and 4 months post placement, and then the absence of the depot at 4.5 months.

TABLE 12

| | IOP | | | | Pupil Diameter | | | |
|---|---|---|---|---|---|---|---|---|
| | Low (14 μg) | | High (41 μg) | | Low (14 μg) | | High (41 μg) | |
| Timepoint | Avg. | Std Dev | Avg. | Std Dev | Avg. | Std Dev | Avg. | Std Dev |
| Baseline | 20 | 2 | 21 | 3 | 6 | 1 | 7 | 1 |
| 1 month | 14 | 5 | 15 | 3 | 2 | 1 | 2 | 1 |
| 2 months | 15 | 3 | 13 | 2 | 2 | 1 | 1 | 1 |
| 3 months | 14 | 4 | 14 | 2 | 2 | 1 | 1 | 0 |
| 3.5 months | 15 | 3 | 14 | 2 | 2 | 1 | 1 | 1 |
| 4 months | 14 | 1 | 13 | 2 | 2 | 1 | 2 | 1 |
| 4.5 months | 16 | 3 | 16 | 3 | 3 | 2 | 2 | 1 |
| 5 months | 16 | 4 | 14 | 2 | 5 | 2 | 3 | 1 |
| 5.5 months | 16 | 3 | 18 | 4 | 5 | 0 | 5 | 0 |
| 6 months | 16 | 3 | 20 | 4 | 6 | 1 | 5 | 1 |
| 6.5 months | 16 | 2 | 16 | 2 | 6 | 0 | 5 | 1 |
| 7 months | 18 | 1 | 16 | 3 | 6 | 0 | 5 | 1 |

Example 7: Formation of Travoprost Sustained Release Depots and In Vitro Testing Results Under "Static" and "Agitated" Conditions Test articles were prepared as in Example 1, but contained an elevated travoprost dose of 328 μg per depot and larger size depots were prepared. The dried dimension of the depots were 0.65 mm×3.2 mm. The hydrated dimensions were 1.8 mm×2.6 mm. The amount of travoprost was controlled by the total amount of microparticles used. The particles were well-mixed within the hydrogel.

The inventors performed in vitro release testing under sink conditions using simulated physiological conditions (PBS, pH 7.4 at 37° C.) with the exception of the addition of 0.5% polyoxyl 40 hydrogenated castor oil to the dissolution media to increase travoprost solubility. This surfactant is used as a solubility enhancement agent in TRAVATAN eye drops. The study evaluated the release of a sample drug (travoprost) that is encapsulated in microparticles and subsequently enmeshed within a PEG hydrogel network and then subjected to "static" non-mixed versus "continuous" agitated dissolution in which agitation, i.e. shaking or stirring, is used to maintain the particles or depots suspended or freely moving in the release medium with minimal sedimentation in the release vessel. A condition of 175RPM in a volume of 50 mL was used. In vitro dissolution under agitated conditions at longer times is in progress at this time. The compared release profiles, seen in FIG. 16, overlap through the duration of the test, at Day 42, indicating that the hydrogel shields the microparticles from the convective forces of agitation during dissolution. The volume of the sink was 50 ml. Artisans can readily determine a suitable sink condition, which is a term of art that refers to having an excess of solution that is large enough so that accumulation of released agents in the solution essentially does not affect ongoing release of agents. The make-up of the PBS was 1 part of OMNIPUR® 10×PBS liquid concentrate (MilliporeSigma) diluted with 9 parts of deionized water and then sterile filtered through a 0.2 micron filter.

Conjunctiva

| | A. REDNESS/CONGESTION (refers to palpebral and bulbar conjunctivae excluding cornea and iris): |
|---|---|
| 0 | Vessels normal. May appear blanched to reddish pink without perilimbal injection (except at 12:00 and 6:00 o'clock positions) with vessels of the palpebral and bulbar conjunctivae easily observed. |
| 1 | Vessels definitely injected above normal. A flushed, reddish color predominately confined to the palpebral conjunctivae with some perilimbal injection but primarily confined to the lower and upper parts of the eye from, the 4:00 and 7:00 and 11:00 to 1:00 o'clock positions. |
| 2*† | More diffuse, deeper crimson red, individual vessels not easily discernible. Bright red color of the palpebral conjunctiva with accompanying perilimbar injection covering at least 75% of the circumference of the perilimbal region. |
| 3*† | Diffuse beefy red. Dark beefy red color with congestion of both the bulbar and palpebral conjunctiva along with pronounced perilimbal injection and the presence of petechia on the conjunctiva. The petechia generally predominate along the nictitating membrane and the upper palpebral conjunctivae. |
| | B. CHEMOSIS: |
| 0 | Normal. No swelling of the conjunctival tissue. |
| 1 | Any swelling above normal (includes nictitating membrane). Swelling above normal without eversion of the lids (can be easily ascertained by noting that the upper and lower eyelids are positioned as in the normal eye); swelling generally starts in the lower cul-de-sac near the inner canthus which needs slit-lamp examination. |
| 2*† | Obvious swelling with partial eversion of lids. Swelling with misalignment of the normal approximation of the lower and upper eyelids; primarily confined to the upper eyelid so that in the initial stages the misapproximation of the eyelids begins by partial eversion of the upper eyelid. In this stage, swelling is confined generally to the upper eyelid, although it exists in the lower cul-de-sac. Swelling with lids about half closed. |
| 3*† | Swelling definite with partial eversion of the upper and lower eyelids essentially equivalent. This can be easily ascertained by looking at the animal straight head on and noticing the positioning of the eyelids; if the eye margins do not meet, eversion has occurred. |
| 4*† | Swelling with lids about half closed to completely closed. Eversion of the upper eyelid is pronounced with less pronounced eversion of the lower eyelid. It is difficult to retract the lids and observe the perilimbal region. |
| | C. DISCHARGE: |
| 0 | Normal or no discharge. |
| 1 | Any amount different from normal (does not include small amounts observed in inner canthus of normal animals). Discharge above normal and present on the inner portion of the eye but not on the lids or hairs of the eyelids. One can ignore the small amount that is in the inner and outer canthus if it has not been removed prior to starting the study. |
| 2 | Discharge with moistening of lids and hairs just adjacent to lids. Discharge is abundant, easily observed, and has collected on the lids around the hairs of the eyelids. |
| 3 | Discharge with moistening of the lids and hairs, and considerable area around the eye. Discharge has been flowing over the eyelids so as to wet the hairs substantially on the skin around the eye. |

Cornea

| | A. OPACITY-degree of density (areas most dense taken for reading): |
|---|---|
| 0 | No ulceration or opacity. Normal cornea. Appears with the slit lamp as having a bright gray line on the endothelial surface and a bright gray line on the endothelial surface with a marble-like gray appearance of the stroma. |

| | |
|---|---|
| 1* | Scattered or diffuse areas of opacity (other than slight dulling of normal luster), details of iris clearly visible. Some loss of transparency. Only the anterior one-half of the stroma is involved as observed with an optical section of the slit lamp. The underlying structures are clearly visible with diffuse illumination, although some cloudiness can be readily apparent with diffuse illumination. |
| 2*† | Easily discernible translucent areas, details of iris slightly obscured. Moderate loss of transparency. In addition to involving the anterior stroma, the cloudiness extends all the way to the endothelium. The stroma has lost its marble-like appearance and is homogeneously white. With diffuse illumination, underlying structures are clearly visible. |
| 3*† | Opalescent/nacreous areas, no details of iris visible, size of pupil barely discernible. Involvement of the entire thickness of the stroma. With optical section, the endothelial surface is still visible. However, with diffuse illumination the underlying structures are just barely visible (to the extent that the observer is still able to grade flare, iritis, observe for pupillary response, and note lenticular changes. |
| 4*† | Opaque cornea, iris not discernible through opacity. Involvement of the entire thickness of the stroma. With the optical section, cannot clearly visualize the endothelium. With diffuse illumination, the underlying structures cannot be seen. Cloudiness removes the capability of judging and grading aqueous flare, iritis, lenticular changes, and pupillary response. |

B. AREAS OF CORNEA INVOLVED:

| | |
|---|---|
| 0 | Normal cornea with no area of cloudiness. |
| 1 | One-quarter (or less), but not zero. |
| 2 | Greater than one-quarter, but less than one-half. |
| 3* | Greater than one-half, but less than three-quarters. |
| 4* | Greater than three-quarters, up to whole area. |

C. FLUORESCEIN STAINING:

| | |
|---|---|
| 0 | Absence of fluorescein staining. |
| 1 | Slight fluorescein staining confined to a small focus. With diffuse illumination the underlying structures are easily visible. The outline of the papillary margin is as if there were no fluorescein staining. |
| 2 | Moderate fluorescein staining confined to a small focus. With diffuse illumination the underlying structures are clearly visible, although there is some loss of detail. |
| 3 | Marked fluorescein staining. Staining may involve a larger portion of the cornea. With diffuse illumination the underlying structures are barely visible but are not completely obliterated. |
| 4 | Extreme fluorescein staining With diffuse illumination the underlying structures cannot be observed. |

D. CORNEA PANNUS:

| | |
|---|---|
| 0 | No pannus |
| 1 | Vascularization is present but vessels have not invaded the entire corneal circumference. Where localized vessel invasion has occurred, they have not penetrated beyond 2 mm. |
| 2 | Vessels have invaded 2 mm or more around the entire corneal circumference. |

40

Iris

A. VALUES:

| | |
|---|---|
| 0 | Normal iris without any hyperemia of the iris vessels. Occasionally around the 12:00 to 1:00 position near the pupillary border and the 6:00 and 7:00 position near the pupillary border there is a small area around 1-3 mm in diameter in which both the secondary and tertiary vessels are slightly hyperemic. |
| 1*† | Folds above normal, congestion, swelling, circumcorneal injection (any or all of these or combination of any thereof), iris still reacting to light (sluggish reaction is positive). Minimal injection of secondary vessels but not tertiary. Generally, it is uniform, but may be of greater intensity at the 1:00 or 6:00 position, the tertiary vessels must be substantially hyperemic. |
| 2*† | No reaction to light, hemorrhage, gross destruction (any or all of these). Minimal injection of tertiary vessels and minimal to moderate injection of the secondary vessels. |
| 3*† | Moderate injection of the secondary and tertiary vessels with slight swelling of the iris stroma (this gives the iris surface a slightly rupose appearance which is usually most prominent near the 3:00 and 9:00 positions). |
| 4*† | Marked injection of the secondary and tertiary vessels with marked swelling of the iris stroma. The iris appears rugose; may be accompanied by hemorrhage (hyperemia) in the anterior chamber. |

AQUEOUS FLARE:

| | |
|---|---|
| 0 | Absence of visible light beam in the anterior chamber (no Tyndall effect). |
| 1 | Tyndall effect is barely discernible. The intensity of the light beam in the anterior chamber is less than the density of the slit beam as it passes through the lens. |

| | |
|---|---|
| 2 | The Tyndall effect in the anterior chamber is easily discernible and is of equal intensity as the density of the slit beam as it passes through the lens. |
| 3 | The Tyndall effect in the anterior chamber is easily discernible; its intensity is greater than the intensity of the slit beam as it passes through the lens. |

PUPILLARY LIGHT REFLEX:

| | |
|---|---|
| 0 | Normal pupillary light reflex |
| 1 | Sluggish pupillary light reflex |
| 2 | No pupillary light reflex |

LENS:
The lens should be evaluated routinely during ocular evaluations and graded as either 0 (normal) or 1 (abnormal).

| | |
|---|---|
| 0 | Normal |
| 1 | The presence of lenticular opacities should be described and the location noted as defined below:<br>Anterior capsule<br>Anterior subcapsule<br>Anterior cortical<br>Nuclear<br>Posterior cortical<br>Posterior subcapsule<br>Posterior capsule |

\*= Positive Reaction (ISO)
†= Positive Reaction (OECD)

FURTHER DISCLOSURE

This further disclosure is directed to various embodiments of the invention.

1A. A method of treating an eye for an ocular condition, the method comprising
placing a xerogel depot depot in an anterior chamber of an eye to deliver a therapeutic agent, with the xerogel depot being a hydrogel after exposure to intraocular fluid, wherein the depot provides a controlled release of a therapeutic agent into the eye after placement of the depot into the eye.

1B. A method of delivery of a therapeutic agent, the method comprising
placing a xerogel depot at a site to deliver a therapeutic agent, with the xerogel depot being a hydrogel after exposure to physiological fluid, wherein the depot provides a controlled release of a therapeutic agent.

1C. A method of delivery of a therapeutic agent, the method comprising
placing a xerogel depot at a site to deliver a therapeutic agent, with the xerogel depot being a hydrogel after exposure to physiological fluid, wherein the depot provides a controlled release of a therapeutic agent. For example, wherein the site is an eye, sub-tenons, intracameral, intravitreal, intrasceleral, choroidal, suprachoroidal, a retina, subretinal, a lens, cornea, sclera, a tissue, lumen, void, potential space, inside an animal (human or otherwise), or on a surface of an animal, iatrogenic site, site where tissue is removed, surgical site, cancer tissue, at or near cancer tissue, dental tissue, gums, periodontal, sinus, brain, intravascular, aneurysm, or site of a pathology.

1D. A method of making an depot comprising a matrix and a therapeutic agent wherein an index of depot residue retention is less than 2.

1E. A method of treating an eye for an ocular condition, the method comprising
placing a composite depot comprising a xerogel with embedded hydrolytically degradable particles into an anterior chamber of an eye to deliver a therapeutic agent, with the xerogel being a hydrogel after exposure to intraocular fluid, with the hydrogel being hydrolytically degradable, wherein the hydrolytically degradable particles comprise the therapeutic agent and hydrolytically degrade in the anterior chamber to provide a controlled release of the therapeutic agent into the eye, wherein an index of depot residue retention (IRR) is from 0.5 to 2.0, with IRR being a time to full dissolution of the depot divided by a time to release of 100% of the therapeutic agent.

2. The method of 1 (referring to 1A, 1B . . . 1n) wherein the agent is disposed in degradable particles in the depot.

3. The method of 1 wherein the hydrogel provides a coefficient of increased delivery time of at least 2, said coefficient being measured in vitro under agitation conditions sufficient to suspend the hydrolytically degradable particles in phosphate buffered saline and being a time for 100% release of the agents in a presence of the hydrogel divided by a time for 100% release of the agents from the particles in an absence of the hydrogel.

4. The method of any of 1-3 wherein a matrix of the xerogel has a dry weight that is at least 20% of a sum of the dry weight of the xerogel matrix and a dry weight of the embedded hydrolytically degradable particles.

5. The method of any of 1-4 wherein a matrix of the hydrogel is formed by covalently crosslinking one or more multiple-arm polyethylene glycol precursors that comprise hydrolytically degradable linkages on each of the multiple arms so that hydrolysis products of the hydrogel are non-toxic and the matrix formed of the polyethylene glycol precursors is hydrolytically degraded to be multiple-arm polyethylene glycol molecules with arms that terminate in hydroxyl or carboxyl end groups.

6. The method of 4 wherein at least one of the multi-arm polyethylene glycol precursors has a molecular weight that is no more than 50 kDa (Mn) and a number of the multiple arms is at least four.

7. The method of 6 wherein the xerogel and/or the at least one multi-arm polyethylene glycol precursors are sterilized by irradiation.

8. The method of any of 1-7 wherein the hydrolytic ally degradable particles are sterilized by irradiation.

9. The method any of 1-8 wherein the composite is sterilized by irradiation.

10. The method of any of 1-9 wherein the composite depot is placed into the anterior chamber using a needle smaller than, or equal to, 25 gauge.

11. The method of any of 1-10 wherein the controlled release of the agent takes place in a period of time between 10 days and 2 years.

12. The method of any of 1-11 wherein the hydrogel is formed by at least one hydrophilic precursor covalently crosslinked to form the hydrogel.

13. The method of any of 1-12 wherein the hydrophilic precursor comprises a plurality of arms that are each from 500- to 10,000 Daltons (Mn).

14. The method of any of 1-13 wherein the hydrolytically degradable particles comprise the therapeutic agent and a hydrolytically degradable material.

15. The method of any of 1-14 wherein the hydrolytically degradable material comprises one or more of polylactic acid (PLA), polyglycolic acid (PGA), and a copolymer of PLA and PGA.

16. The method of any of 1-15 wherein the agent is disposed in both particles and also in a matrix of the depot, or only in the matrix.

17. The method of any of 1-16 wherein the controlled release of the agent takes place during a first predetermined period of time. For instance, wherein the controlled release provides an effective concentration of the agent in the anterior chamber, or other site.

18. The method of 17 wherein the depot comprises a/the matrix that maintains self-cohesion during the first period of time.

19. The method of any of 1-18 wherein the first period of time is from 10 days to 2 years.

20. The method of any of 1-19 wherein the depot, after placement in the eye, provides a concentration of the agent that is from 0.05 to 50 ng/mL in an anterior chamber of the eye.

21. The method of any of 1-20 wherein the xerogel has an amount of the agent that is from 1 to 90% w/w relative to total weight of the depot in a dried condition.

22. The method of any of 1-21 wherein the xerogel has an amount of the agent that is from 1 to 500 micrograms (ug).

23. The method of any of 1-22 wherein the hydrogel is rod-shaped and has a diameter of no more than 1.6 mm.

24. The method of any of 1-23 wherein the xerogel is rod-shaped and has a diameter of no more than 1 mm.

25. The method of any of 1-24 wherein the xerogel is disc-shaped, spherical, or hemispherical.

26. The method of any of 1-25 wherein the therapeutic agent comprises travoprost, a prostaglandin analogue, dexamethasone, or moxifloxacin.

27. The method of any of 1-25 wherein the hydrogel is low swelling, as measurable by the hydrogel having a weight increasing no more than about 50% upon exposure to a physiological solution for twenty-four hours relative to a weight of the hydrogel at the time of formation.

28. The method of any of 1-27 wherein the hydrogel or depot or crosslinked matrix is formed by combining a first synthetic precursor comprising nucleophilic groups with a second synthetic precursor comprising electrophilic groups to form covalent crosslinks by reaction of the nucleophilic groups with the electrophilic groups to form the biocompatible hydrogel.

29. The method of any of 1-28 wherein the hydrogel or depot or crosslinked matrix comprises covalent bonds formed by the free radical polymerization of functional groups on the precursors.

30. The method of any of 1-29 wherein the depot is a xerogel is placed in an anterior chamber. And/or the method of any of 1-51 wherein the depot is a xerogel is located at an iridocorneal angle of an anterior chamber.

31. The method of any of 1-30 wherein an index of depot residue retention is less than 2.

32A. An anterior chamber depot comprising a xerogel that comprises a therapeutic agent disposed in particles dispersed in the xerogel, the xerogel being a monolithic hydrogel upon exposure to aqueous solution, wherein the hydrogel has a diameter of less than 1 mm at equilibrium water content (EWC).

32B. A depot to deliver a therapeutic agent comprising a xerogel depot that is a hydrogel after exposure to aqueous fluid (also to physiological fluid), wherein the depot comprises a therapeutic agent and provides a controlled release of the therapeutic agent into the eye after placement of the depot into the eye.

32C. A depot to deliver a therapeutic agent comprising a xerogel depot that is a hydrogel after exposure to physiological fluid, wherein the depot provides a controlled release of a therapeutic agent.

32D. A depot to deliver a therapeutic agent comprising a xerogel depot that comprises the therapeutic agent, with the xerogel depot being a hydrogel after exposure to physiological fluid, wherein the depot provides a controlled release of a therapeutic agent.

32E. A composite depot comprising a xerogel with embedded hydrolytically degradable particles, with the xerogel being a biocompatible hydrogel after exposure to intraocular fluid, with the hydrogel being hydrolytically degradable, wherein the hydrolytically degradable particles comprise the therapeutic agent and hydrolytically degrade in a physiological fluid to provide a controlled release of the therapeutic agent. Accordingly, degradation products of the depot are non-toxic.

33. The depot of 32 (referring to 32A, 32B . . . 32n) wherein a matrix of the xerogel has a dry weight that is at least 20% of a sum of the dry weight of the xerogel matrix and a dry weight of the embedded hydrolytic ally degradable particles.

34. The depot of 32 or 33 wherein a matrix of the hydrogel is formed by covalently crosslinking one or more multiple-arm polyethylene glycol precursors that comprise hydrolytically degradable linkages on each of the multiple arms so that hydrolysis products of the hydrogel are non-toxic and the one or more multiple-arm polyethylene glycol precursors are hydrolytically degradable to be multiple-arm polyethylene glycol molecules with arms that terminate in hydroxyl or carboxyl end groups.

35. The depot of 34 wherein at least one of the multi-arm polyethylene glycol precursors has a molecular weight that is no more than 50 kDa (Mn) and a number of the multiple arms is at least four.

36. The depot of any of 32-34 wherein the controlled release of the agent takes place in a period of time between 10 days and 2 years.

37. The depot of any of 32-36 wherein the hydrogel is formed by at least one hydrophilic precursor covalently crosslinked to form the hydrogel.

38. The depot of any of 32-37 wherein the hydrolytically degradable particles comprise the therapeutic agent and a hydrolytically degradable material.

39. The depot of 38 wherein the hydrolytically degradable material comprises one or more of polylactic acid (PLA), polyglycolic acid (PGA), and a copolymer of PLA and PGA.

40. The depot of any of 32-39 wherein the therapeutic agent comprises travoprost, a prostaglandin analogue, a low-soluble prostaglandin analogue, an anti-angiogenic agent, an intraocular pressure-lowering agent, an anti inflammatory, an anti infective, a mydriatic agent, an anti-cancer agent, anti-VEGF, blocks VEGFR1, blocks VEGFR2, blocks VEGFR3, anti-PDGF, anti-PDGF-R blocks PDGFRβ, anti-angiogenesis, sunitinib, E7080, takeda-6d, tivozanib, regorafenib, sorafenib, pazopanib, axitinib, nintedanib, cediranib, vatalanib, motesanib, macrolides, sirolimus, everolimus, a tyrosine kinase inhibitor, imatinib, gefinitib, toceranib, erlotinib, lapatinib, nilotinib bosutinib neratinib, lapatinib, vatalanib, a steroid, a nonsteroidal anti-inflammatory drug, an antibiotic, a pain killer, dexamethasone, moxifloxacin, nepafenac, a macrolide, rapamycin, sirolimus, tacrolimus, lipoic acid and derivatives, or sterols, oxysterols and related compounds.

41. The depot of any of 32-440 wherein the index of depot residue retention is less than 2. The depot may comprise a matrix and a therapeutic agent that is released from the depot, with the index being a time for complete degradation (disappearance) of the matrix divided by a time for complete release of the agent.

42. The depot of any of 32-41 wherein the depot is a xerogel is located at an eye, sub-tenons, intracameral, intravitreal, intrascleral, choroidal, suprachoroidal, a retina, subretinal, a lens, cornea, sclera, a tissue, lumen, void, potential space, inside an animal (human or otherwise), or on a surface of an animal, iatrogenic site, site where tissue is removed, surgical site, cancer tissue, at or near cancer tissue, dental tissue, gums, periodontal, sinus, brain, intravascular, aneurysm, or site of a pathology.

43. A kit made by a method of, or comprising a depot of, any of 1-42.

44. A use of a depot of any of 1-42 for one or more of: treatment on an eye condition; treatment of an ocular disease, delivery of a therapeutic agent; treatment of a disease; treatment of a tissue.

45. A process of making a medicament, a process of making a kit, a process of making a system comprising any of 1-42.

Patents, patent applications, patent publications, journal articles, and publications referenced herein are hereby incorporated by reference; in case of conflict, the present specification is controlling. Subheadings are provided herein for convenience of the reader and are not limiting in regards to substantive disclosure. Embodiments not explicitly set forth herein may be formed by mixing and matching features of the various embodiments set forth herein as guided by considerations of operability.

REFERENCES

Edward O. MacKay, Marsha McLaughlin, Caryn E. Plummer, Anna Ben-Shlomo and Kirk N. Gelatt, Dose response for travoprost in glaucomatous beagles. Veterinary Ophthalmology (2011) 1-5.

Alex B. Carvalho, José L. Laus, Vital P. Costa, Paulo S. M. Barros and Patrícia R. Silveira, Effects of travoprost 0.004% compared with latanoprost 0.005% on the intraocular pressure of normal dogs. Veterinary Ophthalmology (2006) 9, 2, 121-125

Hughes P M, Robinson M R, Burke J A, Intraocular pressure reduction with intracameral bimatoprost implants. US Patent Application 2010/0278898 A1, Nov. 4, 2010

Kirk N. Gelatt and Edward O. MacKay, Effect of different dose schedules of travoprost on intraocular pressure and pupil size in the glaucomatous Beagle Veterinary Ophthalmology (2004) 7, 1, 53-57

Ann R. Strom, Dennis E. Cortes, Carol A. Rasmussen, Sara M. Thomasy, Kim McIntyre, Shwu-Fei Lee, Philip H. Kass, Mark J. Mannis and Christopher J. Murphy, In vivo evaluation of the cornea and conjunctiva of the normal laboratory beagle using time- and Fourier-domain optical coherence tomography and ultrasound pachymetry. Veterinary Ophthalmology (2016) 19, 1, 50-56

Leo Trevino; Tomas Navratil; RiLee Robeson; Andres Garcia; Janet Tully; Michael Hunter; Daria Stoltz; Benjamin Maynor; Brian C Gilger; Benjamin R Yerxa, Intracameral Conversion of Travoprost to Travoprost Acid in the Normotensive Beagle Dog Model. Investigative Ophthalmology & Visual Science April 2014, Vol. 55, 5270

Robert Faulkner, Najam A. Sharif, Susan Orr, Kenneth Sall, Harvey DuBiner, Jess T. Whitson, Marlene Moster, E. Randy Craven, Michael Curtis, Cynthia Pailliotet, Kimberly Martens, and David Dahlin, Aqueous humor concentrations of bimatoprost free acid, bimatoprost and travoprost free acid in cataract surgical patients administered multiple topical ocular doses of LUMIGAN or TRAVATAN. J Ocul Pharmacol Ther. 2010 April: 26(2): 147-56

J M Martinez-de-la-Casa, O Rayward, F Saenz-Frances, E Santos-Bueso, C Mendez-Hernandez, R Herrero-Vanrell, J Garcia-Feijoo and J Garcia-Sanchez, Effects of corneal thickness on the intraocular penetration of travoprost 0.004%. Eye (2012) 26, 972-975

Gelatt, Kirk N., and Edward O. Mackay. "Effect of Different Dose Schedules of Travoprost on Intraocular Pressure and Pupil Size in the Glaucomatous Beagle." Veterinary Ophthalmology 7.1 (2004): 53-57.

Hellberg, Mark R., Verney L. Sallee, Marsha A. Mclaughlin, Naj A. Sharif, Louis Desantis, Tom R. Dean, and Paul W. Zinke. "Preclinical Efficacy of Travoprost, a Potent and Selective FP Prostaglandin Receptor Agonist." Journal of Ocular Pharmacology and Therapeutics 17.5 (2001): 421-32.

Driscoll A and Blizzard C, Toxicity and Pharmacokinetics of Sustained-Release Dexamethasone in Beagle Dogs. Adv Ther. 2016 January; 33(1):58-67

Arthur Driscoll; Charles D Blizzard; Michael Bassett; Monica OConnor; Steve Takach; Doug Molla; Peter K Jarrett; Amarpreet Sawhney. 90 Day Canine Toxicity Study Demonstrating the Safety of a Sustained Release Travoprost Punctum Plug. Investigative Ophthalmology & Visual Science April 2014, Vol. 55, 4885.

D'Souza, Susan, Jabar A. Faraj, and Patrick P. DeLuca. "Unstirred Water Layer Effects on Biodegradable Microspheres." Advances in Pharmaceutics 2015 (2015)

D'Souza, Susan S., and Patrick P. DeLuca. "Development of a dialysis in vitro release method for biodegradable microspheres." Aaps Pharmscitech 6.2 (2005): E323-E328,

The invention claimed is:

1. A method of treating an eye for an ocular condition, the method comprising
placing a composite depot comprising a xerogel with hydrolytically degradable particles that are embedded in the xerogel, into the anterior chamber of an eye to deliver a therapeutic agent, wherein a matrix of the xerogel has a dry weight that is at least 30% of a sum of the dry weight of the xerogel matrix and a dry weight of the hydrolytically degradable particles, with the xerogel being a hydrogel after exposure to intraocular fluid, with the hydrogel being hydrolytically degradable, wherein the-hydrolytically degradable particles have diameters less than 55 microns and comprise the therapeutic agent and a hydrolytically degradable polymer material distinct from the hydrogel, wherein the-hydrolytically degradable particles hydrolytically degrade in the anterior chamber to provide a controlled release of the therapeutic agent into the eye, and wherein an index of composite depot residue retention (IRR) is less than 1.0, with IRR being a time to full dissolution of the hydrogel divided by a time to release of 100% of the therapeutic agent from the hydrolytically degradable particles.

2. The method of claim 1 wherein the hydrogel provides a coefficient of increased delivery time of at least 2, said coefficient being measured in vitro under agitation conditions sufficient to suspend the hydrolytically degradable particles in phosphate buffered saline and being a time for 100% release of the agents in a presence of the hydrogel divided by a time for 100% release of the agents from the particles in an absence of the hydrogel.

3. The method claim 1 wherein the matrix of the xerogel has a dry weight that is from 30% to 50% of a sum of the dry weight of the xerogel matrix and a dry weight of the embedded hydrolytically degradable particles.

4. The method of claim 1 wherein the matrix of the hydrogel is formed by covalently crosslinking one or more multiple-arm polyethylene glycol precursors that comprise hydrolytically degradable linkages on each of the multiple arms so that hydrolysis products of the hydrogel are non-toxic and the matrix formed of the polyethylene glycol precursors is hydrolytically degraded to be multiple-arm polyethylene glycol molecules with arms that terminate in hydroxyl or carboxyl end groups, wherein the hydrogel is low swelling, as measurable by the hydrogel having a weight increasing no more than about 50% upon exposure to a physiological solution for twenty-four hours relative to a weight of the hydrogel at the time of formation, and wherein the hydrolytically degradable polymer material comprises polylactic acid (PLA).

5. The method of claim 4 wherein at least one of the multi-arm polyethylene glycol precursors has a molecular weight that is no more than 50 kDa (Mn) and a number of the multiple arms is at least four.

6. The method of claim 5 wherein the xerogel and/or the at least one multi-arm polyethylene glycol precursors are sterilized by irradiation.

7. The method of claim 1 wherein the hydrolytically degradable particles are sterilized by irradiation.

8. The method of claim 1 wherein the composite depot is sterilized by irradiation.

9. The method of 1 wherein the composite depot is placed into the anterior chamber using a needle smaller than, or equal to, 25 gauge.

10. The method of claim 1 wherein the controlled release of the agent at a therapeutically effective dose takes place in a period of time between 10 days and 2 years.

11. The method of claim 1 wherein the hydrolytically degradable polymer material comprises one or more of polylactic acid (PLA), polyglycolic acid (PGA), and a copolymer of PLA and PGA.

12. The method of claim 1 wherein the ocular condition comprises glaucoma, ocular hypertension, hyphema, macular degeneration, cystoid macular edema (CME), diabetic macular edema (DME), posterior uveitis, diabetic retinopathy, presbyopia, cataract, retinal vein occlusion, or uveitis.

13. The method of claim 1 wherein the therapeutic agent comprises travoprost, a prostaglandin analogue, a low-soluble prostaglandin analogue, an anti-angiogenic agent, an intraocular pressure-lowering agent, an anti inflammatory, an anti infective, a mydriatic agent, an anti-cancer agent, anti-VEGF, blocks VEGFR1, blocks VEGFR2, blocks VEGFR3, anti-PDGF, anti-PDGF-R blocks PDGFRβ, anti-angiogenesis, sunitinib, E7080, takeda-6d, tivozanib, regorafenib, sorafenib, pazopanib, axitinib, nintedanib, cediranib, vatalanib, motesanib, macrolides, sirolimus, everolimus, a tyrosine kinase inhibitor, imatinib, gefinitib, toceranib, erlotinib, lapatinib, nilotinib bosutinib neratinib, lapatinib, vatalanib, a steroid, a nonsteroidal anti-inflammatory drug, an antibiotic, a pain killer, travoprost, dexamethasone, moxifloxacin, nepafenac, a macrolide, rapamycin, sirolimus, tacrolimus, lipoic acid and derivatives, or sterols, oxysterols and related compounds.

14. The method of claim 1 wherein the composite depot has a volume from 0.1 to 1000 μl.

15. The method of claim 1 wherein the composite depot is a rod and wherein the diameter of the rod at equilibrium water content is less than 1 mm.

16. The method of claim 1 wherein the ocular condition comprises ocular hypertension or open-angle glaucoma.

17. The method of claim 16 wherein the therapeutic agent comprises travoprost.

18. The method of claim 17 wherein the therapeutic agent is released at a therapeutically effective dose for at least three months and no more than 8 months.

19. The method of claim 18 wherein an amount of the therapeutic agent in the composite depot has a dry weight from 10 to 100 μg.

20. The method of claim 1 wherein the therapeutic agent is released at a therapeutically effective dose for at least three months and no more than 8 months.

21. The method of claim 20 wherein an amount of the therapeutic agent in the composite depot has a dry weight from 10 to 100 μg.

22. The method of claim 1 wherein the IRR is from 0.5 to less than 1.0.

23. The method of claim 1 wherein the hydrolytically degradable polymer material comprises a blend of one or more polymers with different average molecular weights, wherein the polymers comprise polylactic acid (PLA), polyglycolic acid (PGA), and/or a copolymer of PLA and PGA.

24. The method of claim 1 wherein an amount of the therapeutic agent in the composite depot is from about 1 to about 50 wt % and the amount of the therapeutic agent in the particles is from about 40% to about 80%.

25. A method of treating an eye for an ocular condition, the method comprising
placing a first composite depot comprising a first xerogel with hydrolytically degradable particles that are embedded in the first xerogel, into the anterior chamber of an eye in the iridocorneal angle to deliver a therapeutic agent, wherein a matrix of the first xerogel comprises polyethylene glycol and has a dry weight that is at least 30% of a sum of the dry weight of the first xerogel matrix and a dry weight of the-hydrolytically degradable particles, with the first xerogel being a first hydrogel after exposure to intraocular fluid, with the hydrogel being hydrolytically degradable, wherein the hydrolytically degradable particles have diameters less than 55 microns and comprise the therapeutic agent and a hydrolytically degradable polymer material comprising polylactic acid (PLA), wherein the hydrolytically degradable particles hydrolytically degrade in the anterior chamber to provide a controlled release of the therapeutic agent into the eye, and wherein an index of composite depot residue retention (IRR) is less than 1.0, with IRR being a time to full dissolution of the first hydrogel divided by a time to release of 100% of the therapeutic agent from the hydrolytically degradable particles, and wherein the first composite depot remains in the iridocorneal angle until dissolution.

26. The method of claim 25 further comprising placing a second composite depot having the features of the first composite depot after the dissolution of the first hydrogel to provide a continuous controlled release of a therapeutic amount of travoprost for a period of more than 4 months.

* * * * *

UNITED STATES PATENT AND TRADEMARK OFFICE
CERTIFICATE OF CORRECTION

PATENT NO. : 12,171,869 B2
APPLICATION NO. : 15/714633
DATED : December 24, 2024
INVENTOR(S) : Sawhney et al.

It is certified that error appears in the above-identified patent and that said Letters Patent is hereby corrected as shown below:

On the Title Page

On Page 2, Column 1, Item (56), under "Other Publications", Line 16, delete "Intracular" and insert -- Intraocular --, therefor.

On Page 2, Column 2, Item (56), under "Other Publications", Line 9, delete "Efficancy" and insert -- Efficacy --, therefor.

On Page 2, Column 2, Item (56), under "Other Publications", Line 12, delete "Ophthalmolgy," and insert -- Ophthalmology, --, therefor.

On Page 2, Column 2, Item (56), under "Other Publications", Line 19, delete "Ophthalmolgy," and insert -- Ophthalmology, --, therefor.

On Page 2, Column 2, Item (56), under "Other Publications", Line 24, delete "Dexamethason" and insert -- Dexamethasone --, therefor.

On Page 2, Column 2, Item (56), under "Other Publications", Line 34, delete "Conjuctiva" and insert -- Conjunctiva --, therefor.

On Page 2, Column 2, Item (56), under "Other Publications", Line 57, delete "Dexametasona" and insert -- Dexamethasone --, therefor.

In the Claims

In Column 57, Claim 3, Line 23, after "method" insert -- of --.

In Column 57, Claim 9, Line 53, after "of" insert -- claim --.

In Column 58, Claim 13, Line 11, delete "gefinitib," and insert -- gefitinib, --, therefor.

Signed and Sealed this
Twenty-second Day of April, 2025

Coke Morgan Stewart
*Acting Director of the United States Patent and Trademark Office*

CERTIFICATE OF CORRECTION (continued)
U.S. Pat. No. 12,171,869 B2

In Column 58, Claim 13, Line 12, delete "nilotinib bosutinib neratinib" insert -- nilotinib, bosutinib, neratinib --, therefor.